US009808562B2

(12) United States Patent
Wu et al.

(10) Patent No.: US 9,808,562 B2
(45) Date of Patent: *Nov. 7, 2017

(54) METHODS AND DEVICES FOR APPLYING CLOSED INCISION NEGATIVE PRESSURE WOUND THERAPY

(71) Applicant: KCI Licensing, Inc., San Antonio, TX (US)

(72) Inventors: Kenneth Wu, Sunnyvale, CA (US); Dean Hu, Sunnyvale, CA (US); Sumona Nag, Sunnyvale, CA (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/727,733

(22) Filed: Jun. 1, 2015

(65) Prior Publication Data
US 2016/0175499 A1    Jun. 23, 2016

Related U.S. Application Data

(63) Continuation of application No. 13/783,150, filed on Mar. 1, 2013, now Pat. No. 9,044,234, which is a (Continued)

(51) Int. Cl.
*A61M 1/00*     (2006.01)
*A61M 27/00*    (2006.01)
(Continued)

(52) U.S. Cl.
CPC ......... *A61M 1/0088* (2013.01); *A61B 17/085* (2013.01); *A61M 1/009* (2014.02);
(Continued)

(58) Field of Classification Search
CPC .. A61F 5/44; A61F 7/00; A61F 13/00; A61M 35/00; A61M 1/00; A61M 5/178; A61M 5/24; A61M 25/00
See application file for complete search history.

(56) References Cited

U.S. PATENT DOCUMENTS 1,355,846 A    10/1920  Rannells
2,012,755 A  *  8/1935  De Muth ............. A61B 17/085
                                                    24/381
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.
(Continued)

*Primary Examiner* — Tatyana Zalukaeva
*Assistant Examiner* — Ilya Treyger

(57) ABSTRACT

Disclosed herein are devices, systems and methods for using such devices and systems for treating incisions and wounds. In an aspect, disclosed is a device having a generally planar tension relief module and a flexible sealant structure sized to cover the tension relief module, the flexible sealant structure comprising a lower adhesive surface. The tension relief module includes a conduit structure having a plurality of support structures on an upper surface of the conduit structure and at least one opening extending through the conduit structure from a lower surface to the upper surface. At least a portion of the conduit structure is adapted to be aligned with a longitudinal axis of the incision. The tension relief module also includes opposing adhesive structures coupled to the conduit structure. The lower adhesive surface of the flexible sealant structure and the upper surface of the conduit structure form a flow pathway.

46 Claims, 35 Drawing Sheets

Related U.S. Application Data continuation of application No. 12/890,399, filed on Sep. 24, 2010, now Pat. No. 8,444,614, which is a continuation-in-part of application No. 12/757,654, filed on Apr. 9, 2010, now Pat. No. 8,409,159.

(60) Provisional application No. 61/372,443, filed on Aug. 10, 2010, provisional application No. 61/168,507, filed on Apr. 10, 2009.

(51) Int. Cl.
| | | |
|---|---|---|
| A61B 17/08 | (2006.01) | |
| A61M 35/00 | (2006.01) | |
| A61M 5/24 | (2006.01) | |
| A61M 5/178 | (2006.01) | |
| A61F 13/00 | (2006.01) | |

(52) U.S. Cl.
CPC .......... *A61M 1/0096* (2014.02); *A61M 27/00* (2013.01); *A61F 2013/00536* (2013.01); *A61M 1/0076* (2013.01)

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A * | 6/1997 | Argenta .............. A61F 13/0216 128/897 |
| 5,645,081 A | 7/1997 | Argenta et al. |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,700,819 B2 * | 4/2010 | Ambrosio ............... A61L 27/52 602/41 |
| D618,337 S | 6/2010 | Pratt et al. |
| D624,177 S | 9/2010 | Pratt et al. |
| 8,007,257 B2 | 8/2011 | Heaton et al. |
| 8,287,507 B2 | 10/2012 | Heaton et al. |
| 8,535,283 B2 | 9/2013 | Heaton et al. |
| 8,641,692 B2 | 2/2014 | Tout et al. |
| 8,679,079 B2 | 3/2014 | Heaton et al. |
| 8,864,748 B2 | 10/2014 | Coulthard et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0148921 A1* | 7/2005 | Hsu ..................... A61F 13/0259 602/48 |
| 2007/0265586 A1 | 11/2007 | Joshi et al. |
| 2014/0100539 A1 | 4/2014 | Coulthard et al. |
| 2014/0200535 A1 | 7/2014 | Locke et al. |
| 2015/0018784 A1 | 1/2015 | Coulthard et al. |
| 2015/0094673 A1 | 4/2015 | Pratt et al. |
| 2015/0094674 A1 | 4/2015 | Pratt et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2013/078214 A1 | 5/2013 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peăka, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Partial ISR for corresponding PCT/US2017/018129, dated May 15, 2017.

* cited by examiner

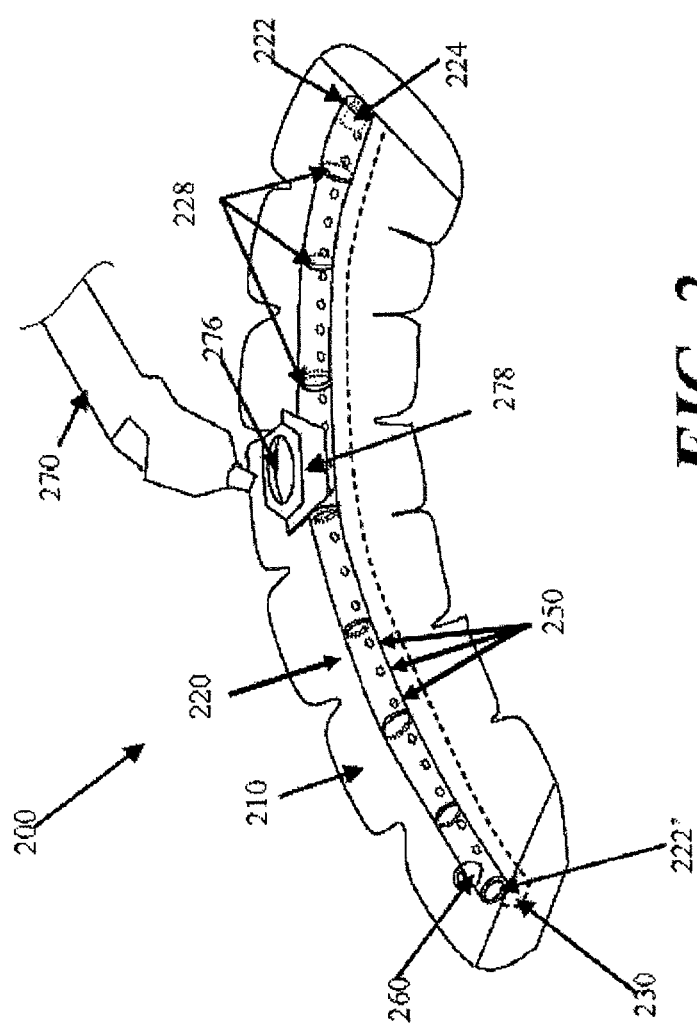

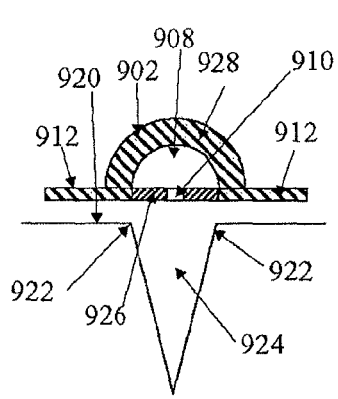
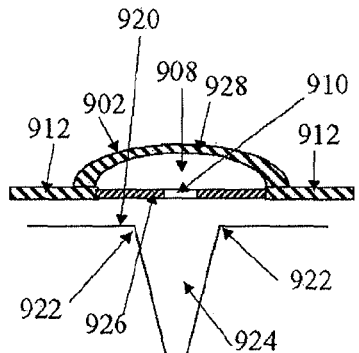
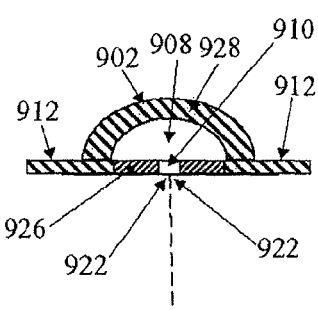
*FIG. 9B*     *FIG. 9C*     *FIG. 9D*
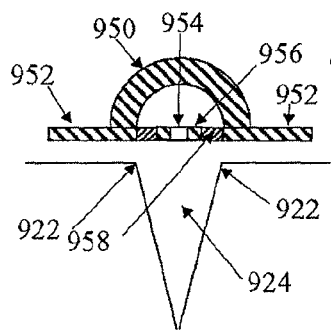
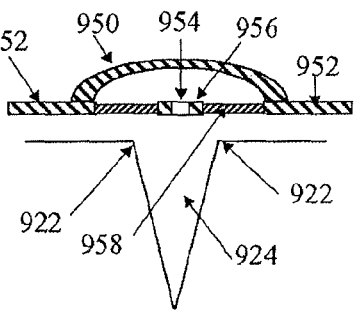
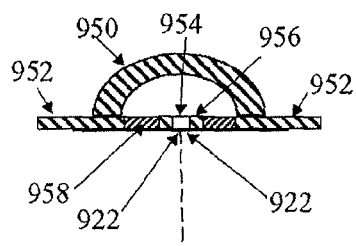
*FIG. 10A*     *FIG. 10B*     *FIG. 10C*
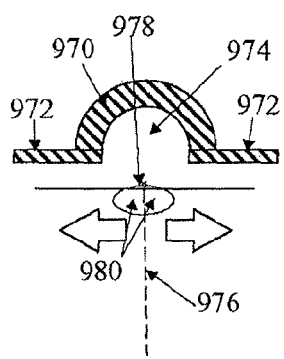
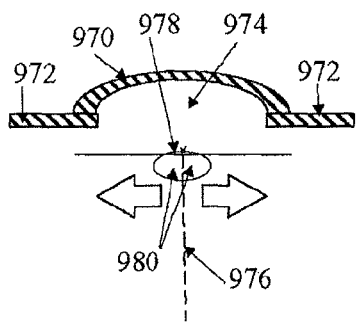
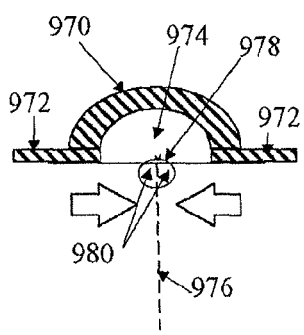
*FIG. 11A*     *FIG. 11B*     *FIG. 11C*

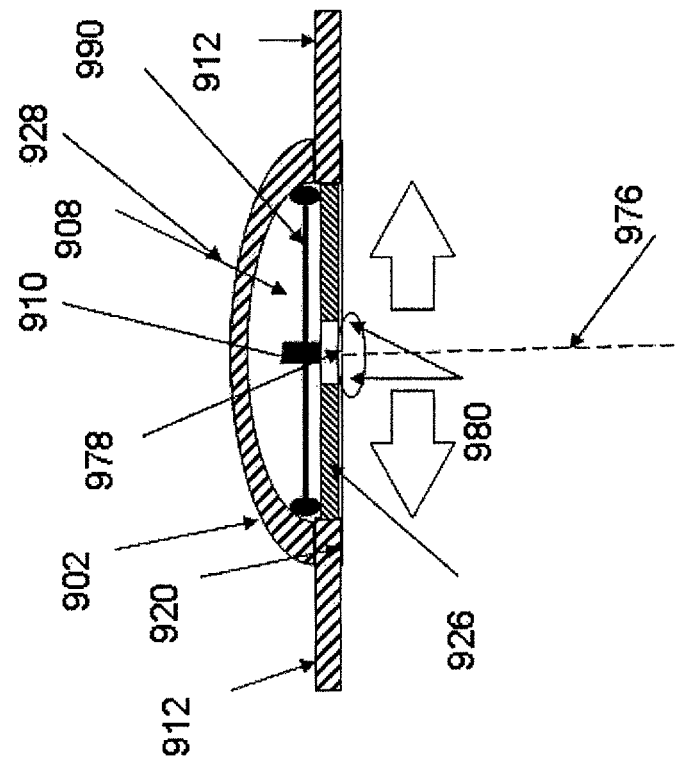
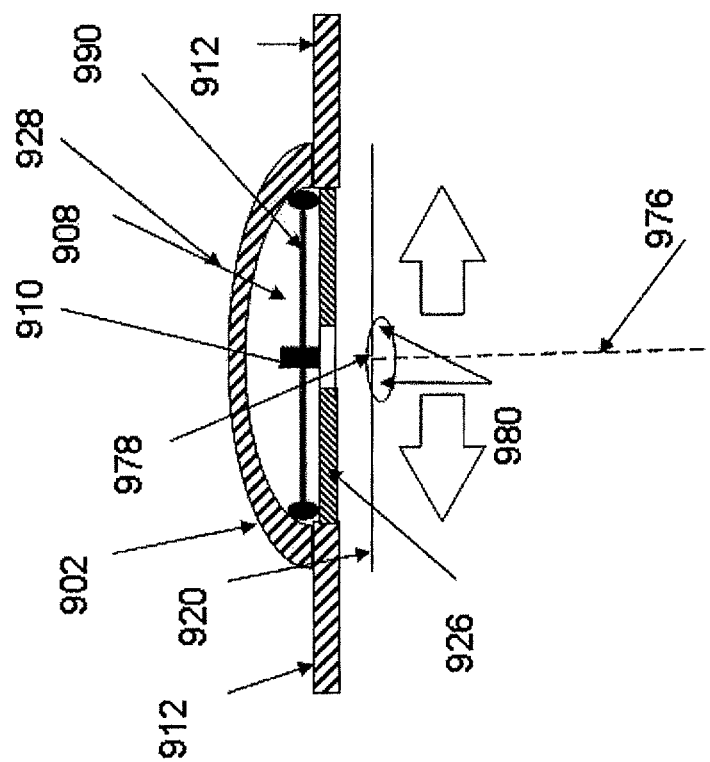

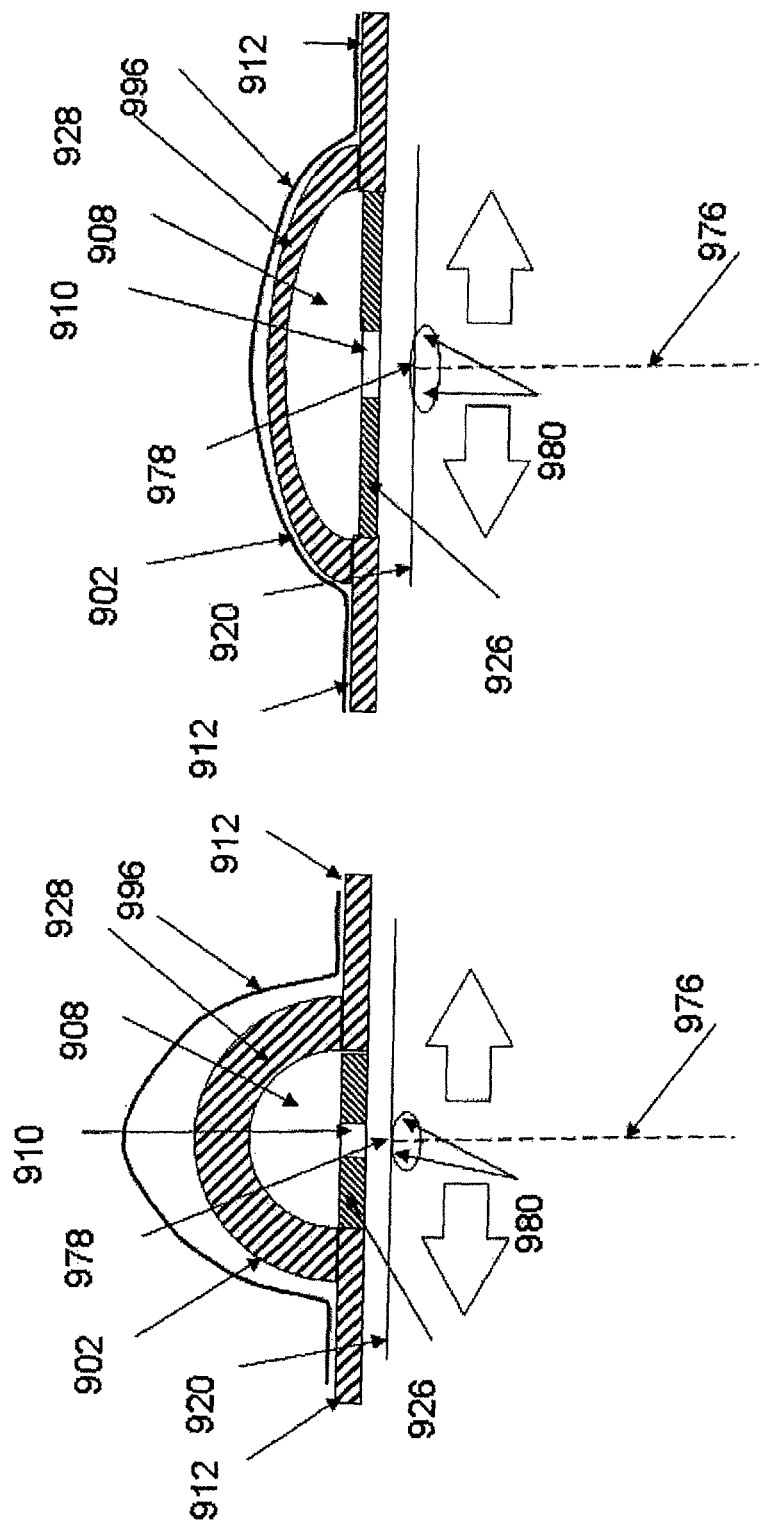

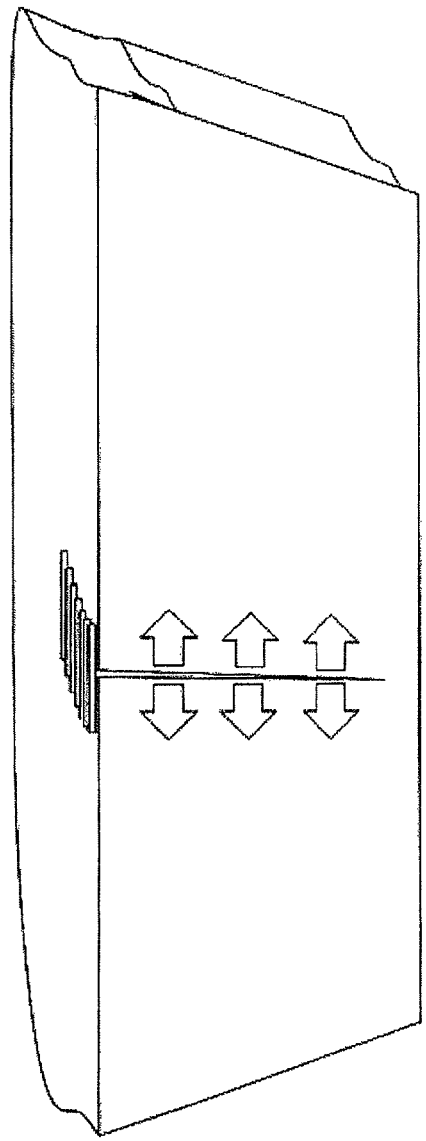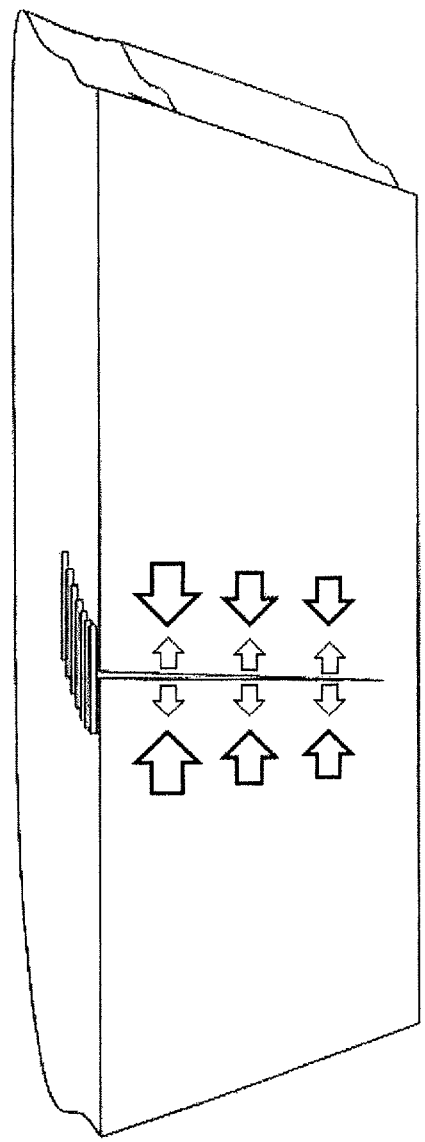

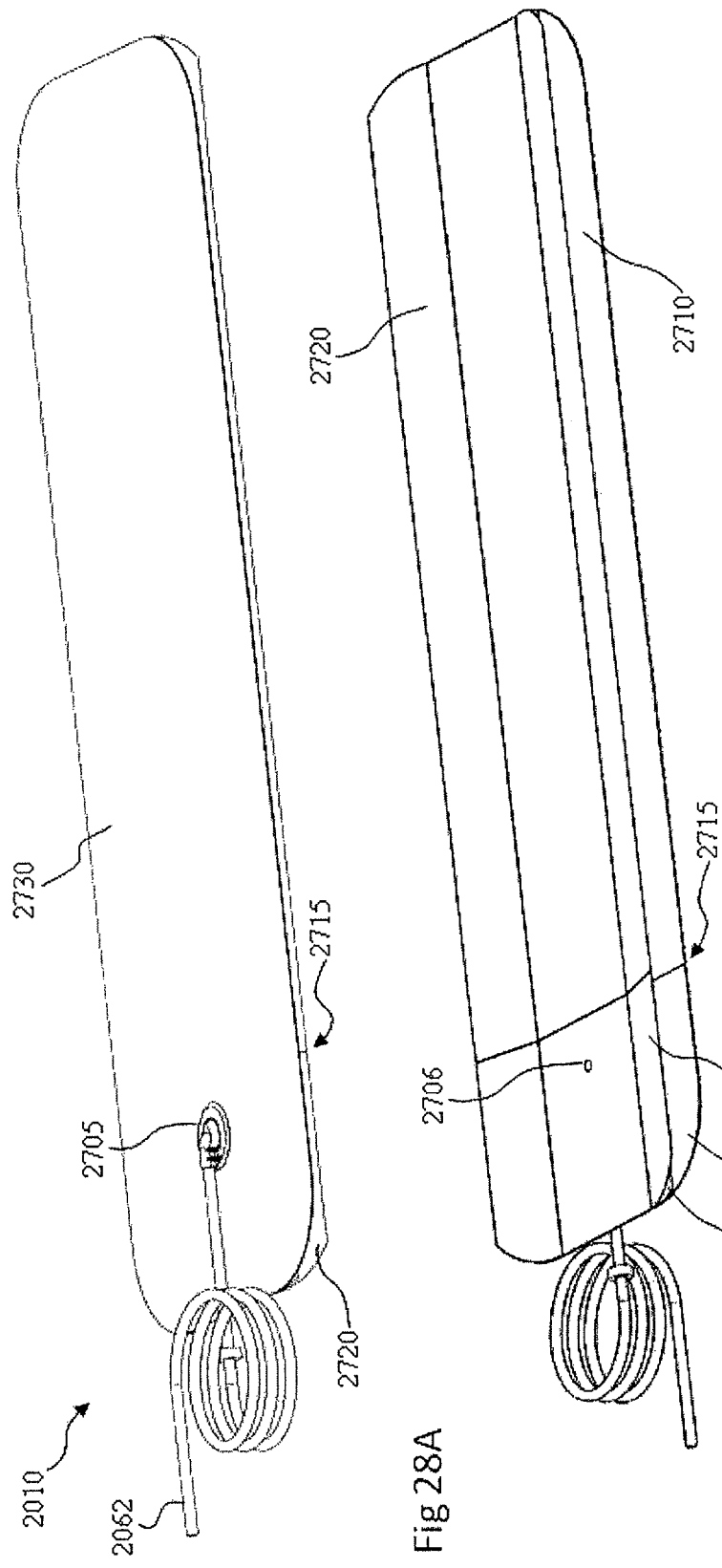

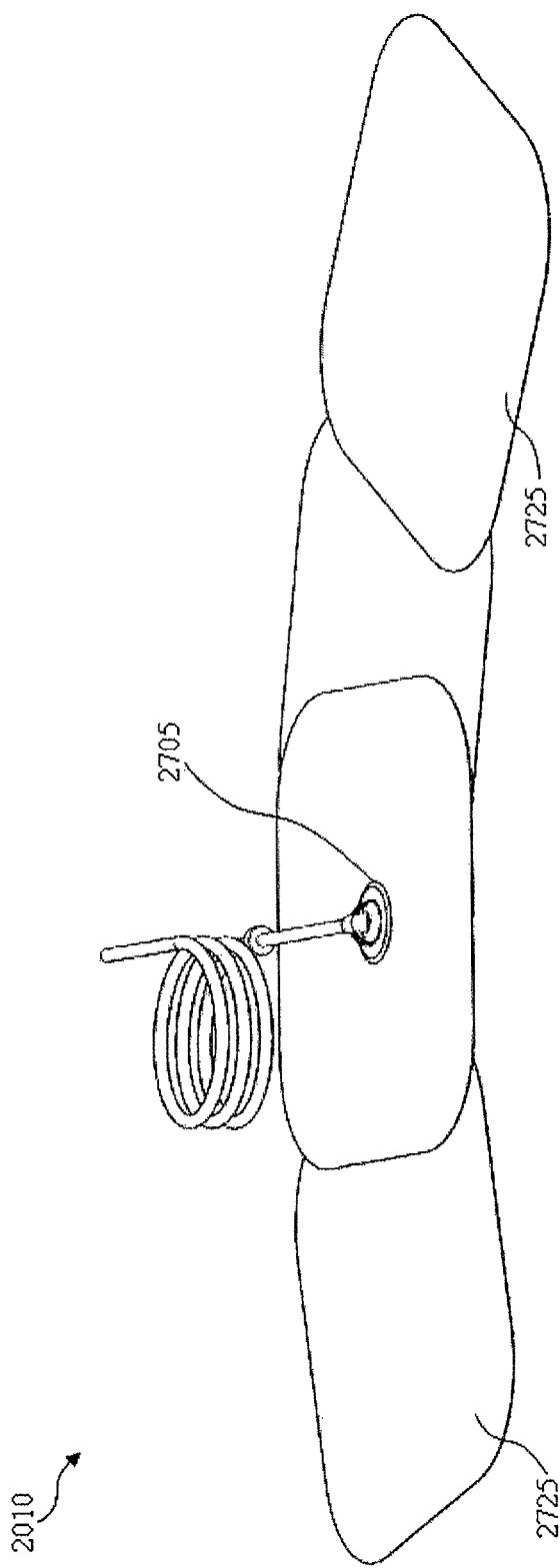

METHODS AND DEVICES FOR APPLYING CLOSED INCISION NEGATIVE PRESSURE WOUND THERAPY

REFERENCE TO PRIORITY DOCUMENT

This application is a continuation and claims priority under 35 U.S.C. §120 of co-pending U.S. patent application Ser. No. 13/783,150, entitled "Methods and Devices for Applying Closed Incision Negative Pressure Wound Therapy," filed Mar. 1, 2013, which is a continuation of U.S. patent application Ser. No. 12/890,399, entitled "Methods and Devices for Applying Closed Incision Negative Pressure Wound Therapy," filed Sep. 24, 2010, now issued as U.S. Pat. No. 8,444,614, which claims priority to U.S. Provisional Patent Application Ser. No. 61/372,443, filed Aug. 10, 2010, entitled "Methods And Devices For Applying Closed Incision Negative Pressure Wound Therapy", filed Aug. 10, 2010, and which is a continuation-in-part of U.S. patent application Ser. No. 12/757,654, entitled "Methods and Devices for Applying Closed Incision Negative Pressure Wound Therapy," filed Apr. 9, 2010, now issued as U.S. Pat. No. 8,409,159, which claims priority to U.S. Provisional Patent Application Ser. No. 61/168,507, entitled "Devices and Methods for Applying Closed Incision Reduced Pressure Therapy Systems," filed Apr. 10, 2009. Priority of the filing dates is hereby claimed and the disclosures of the patent applications are hereby incorporated by reference in their entirety.

BACKGROUND

There are millions of closed incisions (surgical or non surgical) each year, that occur in settings ranging from office-based procedures and ambulatory surgical centers to traditional, in-patient hospital settings. Post-procedural care of these incisions may vary, but can involve simple use of gauze, wraps and tapes. In addition, irrigation of the wound prior to closure and meticulous sterile technique has also been advocated. Wound infections following invasive procedures and surgeries presents a potential risk to patients that can be as high as 10% with abdominal surgeries, for example. Wound infections are a significant morbidity for patients, clinicians, and hospitals and can be costly to taxpayers and other payers. Patients with wound infections may need IV antibiotics, prolonged hospitalization, wound opening and dressing changes, and some go on to develop wound dehiscence and enterocutaneous fistulas. While pre-operative prophylactic antibiotics have been shown to decrease post-operative wound infection, post-operative antibiotics have not.

SUMMARY

Provided herein are devices for treating incisions. In one aspect, disclosed is a device for treating an incision including a generally planar tension relief module and a flexible sealant structure sized to cover the tension relief module and having a lower adhesive surface. The generally planar tension relief module includes a conduit structure having a plurality of support structures on an upper surface of the conduit structure and at least one opening extending through the conduit structure from a lower surface to the upper surface. At least a portion of the conduit structure is adapted to be aligned with a longitudinal axis of the incision. The generally planar tension relief module also includes opposing adhesive structures coupled to the conduit structure. The lower adhesive surface of the flexible sealant structure and the upper surface of the conduit structure form a flow pathway.

In another aspect, disclosed is a system for treating an incision including a device having a generally planar tension relief module and a flexible sealant structure sized to cover the tension relief module. The generally planar tension relief module includes a conduit structure having a plurality of support structures on an upper surface of the conduit structure and at least one opening extending through the conduit structure from a lower surface to the upper surface and opposing adhesive structures coupled to the conduit structure. At least a portion of the conduit structure is adapted to be aligned with a longitudinal axis of the incision. The flexible sealant structure has a lower adhesive surface and a vacuum port. The lower adhesive surface of the flexible sealant structure and the upper surface of the conduit structure form a flow pathway. The system also includes a negative pressure source configured to couple to the vacuum port, the negative pressure source having a constant force spring, a sliding seal and a fixed external profile independent of its internal pressure level.

In another aspect, disclosed is a method of treating an incision that includes applying a contact layer in direct contact with the incision; adhering a generally planar tension relief module over the contact layer and the incision; applying a flexible sealant structure over the tension relief module forming a flow pathway on the upper surface of the conduit structure; and applying a negative pressure to a vacuum port on the sealant structure to evacuate the flow pathway. The tension relief module includes a conduit structure having a plurality of support structures on an upper surface of the conduit structure and at least one opening extending through the conduit structure from a lower surface to the upper surface; and opposing adhesive structures coupled to the conduit structure. Adhering a generally planar tension relief module includes manually stretching the opposing adhesive structures from a relaxed configuration towards a tensile configuration and applying the opposing adhesive structures to a healthy skin surface on either side of the incision.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 depicts an embodiment of a negative pressure therapy device as viewed from above in which the device is designed to be emptied and re-evacuated.

FIGS. 9B to 9D are schematic cross-sectional views of the device in FIG. 9A before, during and after stretching, respectively.

FIGS. 10A to 10C are schematic cross-sectional views of another negative pressure therapy device with reinforced apertures, before, during and after stretching, respectively.

FIGS. 11A to 11C are schematic cross-sectional views of another negative pressure therapy device comprising an open longitudinal channel, before, during and after stretching, respectively.

FIGS. 20A to 20D are schematic cross-sectional views of the deployment of one example of a negative pressure therapy system.

FIGS. 21A to 21D are schematic cross-sectional view of the deployment of another example of a negative pressure therapy system.

FIGS. 22A-22B are schematic cross-sectional views of incision edges being pushed together to lessen tension across the incision.

FIGS. 28A-28B are perspective views of a sealant layer coupled to a connecting tube.

FIG. 29 is a perspective view of a modular sealant layer.

DETAILED DESCRIPTION OF THE INVENTION

Figure 1A:
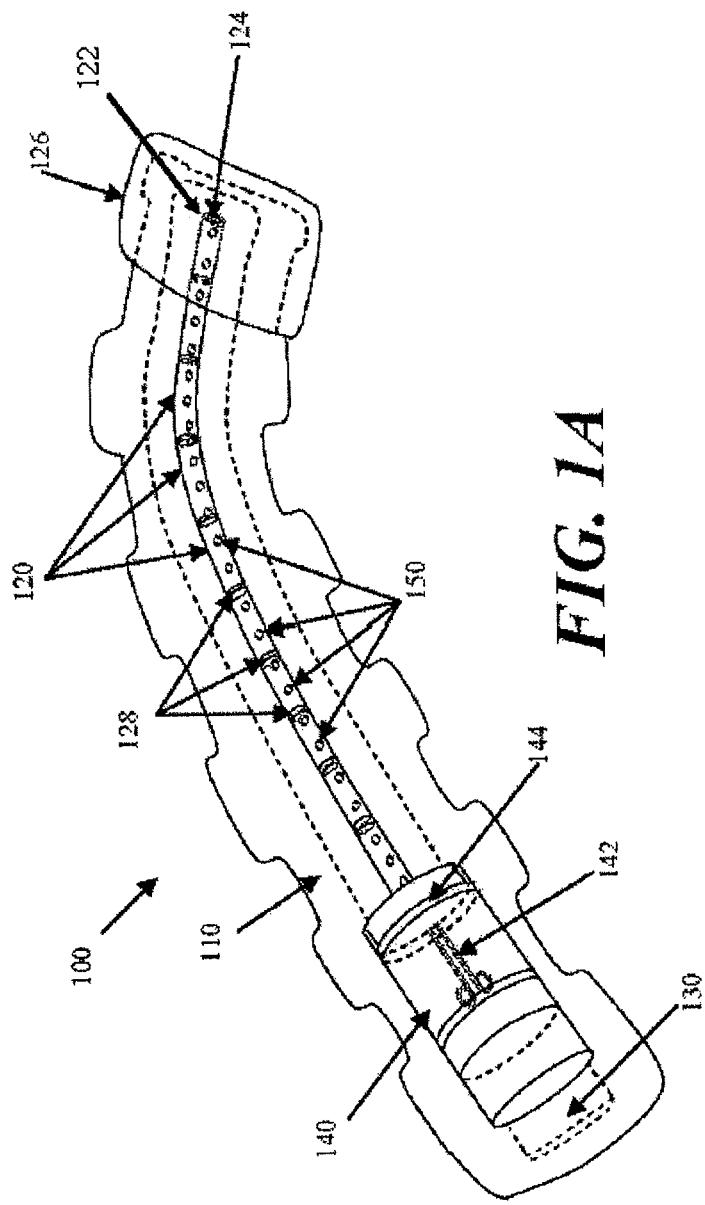
FIGS. 1A and 1B depict one embodiment of a negative pressure therapy device as viewed from the top and from the side perspective.

Infections of surgical incisions and other wounds may result from bacterial growth that occurs in small pockets of fluid collections that may form within the subcutaneous and/or cutaneous tissues. These small fluid collections lack blood flow and thus may prevent adequate immune function or antibiotic penetration to prevent or treat infection. Once contaminated with bacteria there can be unfettered growth in these areas. Thus, by reducing the formation of these fluid collections, the risk of a wound infection may be reduced. Although some closure techniques utilize dermal or deep sutures to reduce the formation of these fluid pockets, these sutures may also act as foreign bodies that may increase the risk of wound infection. Furthermore, improper suturing technique may still leave significant dead space under the skin that allows for fluid to collect and eventually become contaminated by bacteria.

In addition to wound infection, wound healing may be inhibited by excessive tension on the wound. Excessive tension may result from sutures or other wound closure devices that exert focal forces on portions of the incision or wound, and may also lead to increased scarring. Tension across a wound may also occur for other reasons, such as during post-closure movement, the force of gravity, etc.

Studies have also demonstrated that a moist wound healing environment may promote more rapid re-epithelialization of wounds by facilitating cell migration toward the wound center, in contrast to current gauze dressings that create a dry wound environment. Moreover, surgical and other wounds undergo immune cell infiltration, inflammation and subsequent edema. The immune response may be an integral process of wound healing, but the ensuing edema may also be an impediment to healing. Finally, proper healing requires oxygen and nutrients which require adequate perfusion to the incision site which may be impeded by some of the immunological processes.

In one example, a negative or reduced pressure wound therapy system may be used to treat areas of skin trauma that have been surgically closed, or other types of elongate lacerations or wounds. The negative pressure wound therapy system may comprise a sealant layer and a collection chamber. The sealant layer may be designed such that it can form a seal around a surgically closed area of skin trauma, such as the surgical incision, and form a sealed enclosure or space. It should be appreciated that the area of skin trauma need not be previously surgically closed. In some examples, the sealant layer may comprise a single piece or body, while in other examples, the sealant layer may comprise multiple pieces that may be applied together to form an enclosed space or area. The sealant layer may also comprise a single layer of material, or multiple layers of materials. The seal may be sufficiently air tight so that the pressure in the sealed enclosure or space may be reduced and maintained at a reduced level. The negative pressure therapy system may also comprise a collection chamber that is configured to distribute the reduced pressure applied to the surgically closed incision site along the length of the incision or wound. The negative pressure therapy system may also be used to treat a surgical incision left open to heal by secondary intention, or by delayed primary closure (i.e. third intention). The system may comprise a collection chamber in continuity to a surgical incision that is sealed in a closed system as created by a sealant layer. The collection chamber, when activated, may generate a negative pressure at the surgical incision site to promote healing, remove exudate, and/or reduce infection rates, for example. In some particular examples, the system provided herein may have an elongate configuration and may be sized or configured to conform to the length of the surgical incision. The collection chamber may be integrally formed or pre-attached to a sealant layer, or the collection chamber and the sealant layer may be configured to permit the collection chamber to be positioned under the sealant layer.

In some embodiments, the system further comprises a suction apparatus. When the suction apparatus is used with the system, the suction apparatus may be configured to be in communication with the sealed enclosure or space. The suction apparatus, together with the sealant layer and collection chamber, may form a closed system for treating a surgical incision or other type of wound. The suction apparatus, when engaged, may be used to reduce the level of pressure located inside the sealed enclosure by forcefully expanding the volume of air located within the sealed enclosure. The suction source may be a closed or open system. For example, the suction apparatus may be a syringe, a powered pump, a Venturi system, a forced expansion device, constant force spring device, or a static negative pressure device, or any suitable active or passive suction source. In some embodiments, the suction source may be integrally formed with the collection chamber. In some embodiments, the suction source is connected to the collection chamber through the use of an extension tube.

In some embodiments, the system further comprises a contact layer. The contact layer may be configured to permit fluid communication with the collection chamber. The contact layer may be placed in contact with the surface of the surgically closed area of skin trauma. In some embodiments, the contact layer may only be in contact with the surgically closed area of skin trauma and may not be in contact with the area surrounding the site of trauma. In other embodiments, the contact layer may be in contact with both the area of skin trauma and the area surrounding the area of skin trauma. The contact layer may facilitate the continuity of fluid communication between the collection chamber and the surgical area of skin trauma. In some examples, the contact layer may comprise a porous material or other structure comprising air spaces, including, but not limited to, foam, a stacked mesh matrix, gauze, cotton, a sponge, or any known suitable material in the art. In some embodiments where the contact layer is used, the contact layer may serve as a delivery vehicle for delivery agents. The delivery agents may include, but are not limited to, growth factors, antibiotics, antimicrobial agents, or any suitable delivery agent. In some embodiments, the agents used to improve healing are integrated with the contact layer. In some embodiments, the agents used are integrated or located with the collection chamber.

In some embodiments, the system further comprises a protective layer. A protective layer may be used to surround the surgical area of skin trauma. For example, the protective layer may be attached or adhered to the area of skin surround the area of skin trauma. A pressure sensitive adhesive on the underside of the protective layer may provide the attachment or adherence properties to the skin. A protective layer may also be used to form a seal in combination with a sealant layer. The seal is airtight, or may be semi-permeable or impermeable to water vapor. In some embodiments, the protective layer may be sized to the surgical area of skin trauma such that it fits around the area of skin trauma. In some examples, the protective layer may be cut to size, but in other embodiments, the protective layer may comprise perforations or other pre-defined separation structures to facilitate the sizing. In certain embodiments, the protective layer may have a thin central peel-away strip or layer that may be removed after the protective layer has been placed around the area of skin trauma. In such embodiments, a wider contact layer may be placed over the protective layer. The protective layer may be used to affix the contact layer to the surgical area of skin trauma, and may protect the underlying skin or tissue from trauma associated with removal of the contact layer to access the surgical site. The protective layer can be any known material suitable for protecting the skin surrounding the skin trauma from maceration. The protective layer may comprise any of a variety of foam and/or hydrocolloid materials, including Duoderm® wound care products.

The collection chamber of the static negative pressure therapy system may be configured to distribute the pressure levels applied to the incision site over the length of the surgically closed area of trauma. In some embodiments, the collection chamber may be in a pre-evacuated state prior to being placed on the surgically closed incision area of skin trauma. In such an embodiment, the collection chamber, once in communication with the area of skin trauma, can then be activated to apply reduced pressure to the area of skin trauma. In some examples, the collection chamber comprises a tubular structure. The tubular structure may comprise a rigid tube, for example, a moldable or flexible tube. The tube may comprise a deformable or elastic support that permit the tube to be bent or shaped into a particular configuration while also allowing the tube to hold or bias the tube in that configuration. For example, the support structure may comprise a wire mesh cage or frame surrounding the tube, coupled to the inner lumen of the tube, or otherwise supporting the tube. In some embodiments, the tube has a wire support structure integrally within the walls of the tube. The support structure may also comprise a moldable plastic material, or the tubing itself may comprise a moldable plastic. Moldable materials include, but are not limited to, thermoplastics, elastomeric materials, or any suitable moldable material. In some embodiments, the collection chamber may be configured for single use only, while in other embodiments, the collection chamber may be emptied and re-evacuated during use.

In some embodiments, the collection chamber is a flexible tube which comprises one or more corrugated sections. In such an embodiment, the corrugated tubing section may be flexible and can conform to the surface topology of the surgically closed area of skin trauma. The corrugated tubing sections may allow the flexible tubing to conform to the two-dimensional or three-dimension configuration of the wound or incision and allows the tubing to passively adjust in response to changes in the wound configuration as the patient moves or as the wound heals. In some embodiments, the flexible tube may be comprised entirely of corrugated tubing, while in other embodiments, the flexible tubing is corrugated tubing sections with discrete collection members or non-corrugated sections located therebetween. In one embodiment, the non-corrugated sections may be rigid, or may be semi-rigid or flexible but with less flexibility than the corrugated sections. Some embodiments may comprise at least one non-corrugated section located within the tubing, while other embodiments may comprise two or more non-corrugated sections located along the tubing. The tubular segments may be connected by corrugated tubes that provide fluid communication along a length of the tubing and/or provide flexibility to the tubing such that the entire collection chamber structure, the rigid non-corrugated sections and the flexible corrugated tubing sections overall permit conformation to the skin or surgical site as it moves. Sometimes, flexible tubing may mitigate the discomfort to the patient or reduce the localized pressure points from the treatment system. In some embodiments comprising both rigid collection sections and flexible sections along the collection chamber, both the flexible tubing segments and the rigid collection sections may be embedded into the sealant layer, coupled to the sealant layer, or integrally formed with the sealant layer. In some embodiments, only the discrete collection members are coupled or embedded into the sealant layer, while the flexible tubing segments are not.

Some embodiments of the system comprise a collection chamber and a sealant layer, where the sealant layer and the collection chamber are in fluid communication with an area of skin trauma. Fluid communication may be provided by a series of openings in the sealant layer and the collection chamber which provide fluid communication between the area of skin trauma and the collection chamber. The openings may be located longitudinally oriented along a length of the collection chamber, with corresponding openings of the sealant layer aligned with the openings in the collection chamber. Fluid, or any other suitable matter, may then be drawn up from the surgically closed area of skin trauma into the collection chamber. When an optional contact layer is employed, the fluid may pass first through the contact layer, and then through the holes connecting the sealant layer and collection chamber. In addition, the series of openings located throughout the collection chamber may allow for the distribution of pressure to the area of skin trauma and reduce or prevent areas of localized pressure or fluid build-up that may be greater in some areas and less in other areas.

In some embodiments, the collection chamber further comprises a one-way flow valve. The one-way flow valve may be used to assist in the emptying of the collection chamber. The one-way flow valve may also be used to re-create the reduced pressure, or pre-evacuated, level of pressure inside the collection chamber. In some embodiments, the one-way flow valve may be used to facilitate both empting of the collection chamber and re-evacuation of the collection chamber. The one-way flow valve may serve to facilitate the re-evacuation of the collection chamber by facilitating the attachment of a suction source to the collection chamber through the valve and allowing the suction source to remove air molecules from the collection chamber. The suction source may also be used to remove exudate or air from the collection chamber through the use of the one-way flow valve. In some embodiments, a first one-way flow valve is used to empty the collection chamber and a second one-way flow valve is used to re-evacuate the collection chamber. In some embodiments, the one-way flow valve may be integrated with the collection chamber. In some embodiments, the one-way flow valve is attached to a removable plug used to occlude one end of the collection chamber. In some embodiments, a plurality of one-way valves may be provided, with one or more valves located in or associated with the series of openings to reduce backflow of air or material out of the collection chamber or the sealant layer and back into the area of skin trauma. The one-way valves may have any of a variety of configurations, including duckbill or flap valves.

A segmented collection device or other multi-cavity device may be used in place of a single chamber collection chamber in some embodiments. A segmented collection chamber may comprise a first chamber and a second chamber which may or may not be in fluid communication with each other. In one example, the first chamber is in direct communication with the sealant layer whereas the second chamber is in communication with the first chamber. In embodiments where a dual chamber collection chamber is used, one or more of the segments or chambers may be a source of suction. The suction source may comprise a non-powered or passive actuating and regulating mechanism, including but not limited to a spring mechanism such as a constant force spring. The passive actuating and regulating mechanism may be used to apply and maintain a level of pressure inside the sealed enclosure or space between the collection chamber and the sealant layer. In some embodiments, the dual chamber collection chamber comprises a reciprocating mechanism including, but not limited to, a plunger. The plunger may be manually distracted, or may be passively distracted, such as when attached to a constant force spring. In some embodiments, the second chamber expands the volume of air located in a joint volume of space shared between the sealed enclosure and the dual chamber collection chamber. One or segments or chambers may also comprise a powered or active actuating and regulating mechanism.

In some embodiments, the system may also be sized or configured to conform to the length of the surgically closed incision. In some embodiments, the collection chamber conforms to the length of the closed incision area of skin trauma by being stretched to the length of the wound. In such an embodiment, the collection can be made from a hydrocolloid material. Such a material allows the collection chamber to be stretched to a new desired length and remain at that length after the stress causing the change in length has been removed. In such an embodiment, the system may be made from a hydrocolloid or any suitable material. In some embodiments, the system may be shortened to the length of the closed incision. In some embodiments, the system can be cut to the length of the closed area of skin trauma. In such an embodiment, the cut end of the collection chamber may be self sealing upon the application of pressure to the collection chamber. In some embodiments, the collection chamber can be sealed after it has been cut. In some embodiments, the collection chamber can be sealed with an end cap, a plug, an occlusive sealant sheet, an end cap with a one way flow valve, a constant force spring, a reduced pressure system, or any suitable means for sealing the end of the collection chamber. In one embodiment, the structure used to seal the end of the collection chamber that has been adjusted to conform to the length of the skin trauma is configured to resist removal once affixed to the collection chamber. Alternatively, the structure used to seal the end of the collection chamber that has been adjusted to conform to the length of the skin trauma may be a removable structure. In some embodiments, the system includes a series of collection chambers lined up in parallel or serially with each other. In such an embodiment, one or more collection chambers may be removed from the series of collection chambers to accommodate the width of the closed incision area of skin trauma. In other embodiments, one or more collection chambers may be replaced upon filling or clogging.

In some embodiments, the contact layer may be adjusted to conform to the length of the surgically closed area of skin trauma. For example, the contact layer may be lengthened or shortened based upon the length of the closed incision or wound. In some embodiments, the contact layer may be cut to the length of the closed incision. In some embodiments, the collection chamber, the contact layer, and/or the sealant layer may be adjusted to conform to the length of the surgically closed incision. In some embodiments, only the collection chamber is adjusted to conform to the length of the incision before the system is placed on the patient, while in other embodiments, only the contact layer or the sealant layer is adjusted to conform to the length of the surgical incision before the system is placed on the patient. In some embodiments, the collection chamber, the contact layer, and the sealant layer may each be individually adjusted to conform to the length of the incision or wound before being placed on the patient. In some embodiments, the collection chamber, the contact layer, and the sealant layer are integrated together, such that the system is adjusted to conform to the length of the surgically closed incision or wound as a unit.

The system provided herein includes a sealant layer for creating a seal with the surface of the patient. In some embodiments, the seal is air tight. In some embodiments, the sealant layer comprises a flexible impermeable material. In some embodiments the sealant layer is a semi-rigid material. In an embodiment where the sealant layer is a semi-rigid material, the sealant layer may provide tensile support to the surgically closed area of skin trauma. A semi-rigid sealant layer would further alleviate mechanical tension on the surgically closed area of skin trauma as the trauma heals.

In some embodiments, the system provided for herein further includes absorbent beads. The absorbent beads are located in the incision or wound, and/or the collection chamber. In some embodiments, the system may comprise antimicrobial agents. Antimicrobial agents include, but are not limited to, silver, iodine, chlorhexidine or any other suitable antimicrobial agent.

Some of the examples provided herein are configured to create a level of pressure within the sealed enclosure encompassing the surgically closed area of skin trauma. In some embodiments, the level of pressure created is between about 0.001 and about 1 atm. When in fluid communication with the enclosed space under the sealant layer, the level of atmospheric pressure underneath the sealant layer may be reduced to no lower than about 0.001 atm, about 0.005 atm, about 0.01 atm, about 0.05 atm, about 0.1 atm, about 0.2 atm, about 0.5 atm, about 0.7 atm, or about 0.9 atm. In other embodiments, the atmospheric pressure underneath the sealant layer may be reduced to about 0.8 atm or less, but in other embodiments, may be reduced to less than about 0.7 atm, 0.6 atm, about 0.4 atm, about 0.3 atm, about 0.2 atm, about 0.1 atm, about 0.07 atm, about 0.03 atm, about 0.007 atm, or to about 0.003 atm or less.

In some embodiments, the contact layer, the sealant layer and/or the collection chamber may be made from transparent materials. The transparency of the materials may facilitate more accurate placement of the system over the surgical incision or wound by the clinician to more accurately place the system, and/or may permit visualization of the incision or wound with breaking the seal.

Also provided for herein is a method for applying a reduced pressure therapy system to a surgically closed area of skin trauma. The method comprises (a) sizing a collection chamber, a protective layer and a sealant layer to a surgically closed area of skin trauma; (b) forming a seal around the surgically closed area of skin trauma; (c) activating the collection chamber to deliver reduced pressure evenly distributed to the surgically closed area of skin trauma; and (d) removing the system after re-epithelialization of the surgically closed area of skin trauma. Wound re-epithelialization occurs between 2 days and 5 days after the skin trauma has been surgically closed. In some embodiments wound re-epithelialization occurs 3 days after closure. In some embodiments wound re-epithelialization occurs 4 days after closure. In some embodiments wound re-epithelialization occurs 5 days or more after closure. In some embodiments, wound re-epithelialization occurs earlier than 5 days after wound closure. In some embodiments, wound re-epithelialization occurs earlier than 4 days after wound closure. In some embodiments, wound re-epithelialization occurs earlier than 3 days following wound closure.

Further provided is a method for treating an area of skin trauma using a reduced pressure therapy system, comprising: (a) cutting a protective layer to the shape of an area of skin trauma; (b) attaching the cut protective layer to an area of intact skin surrounding the area of skin trauma; (c) cutting a flexible adhesive dressing with an integrated layer of foam to a desired size, said flexible adhesive dressing integrated with said layer of foam in fluid communication with a flexible tubing; (d) placing the dressing over said surgically closed area of skin trauma to form a sealed enclosure; (e) configuring the tubing with an end piece; (f) charging the device; (g) recharging the device as necessary to remove exudates and to restore reduced pressure inside said enclosure; and (h) removing the device after wound re-epithelialization. In some embodiments the skin trauma is selected from a cut, puncture wound, surgically created incision, or any other wound which is suitable for being closed surgically.

Devices

Figure 1B:
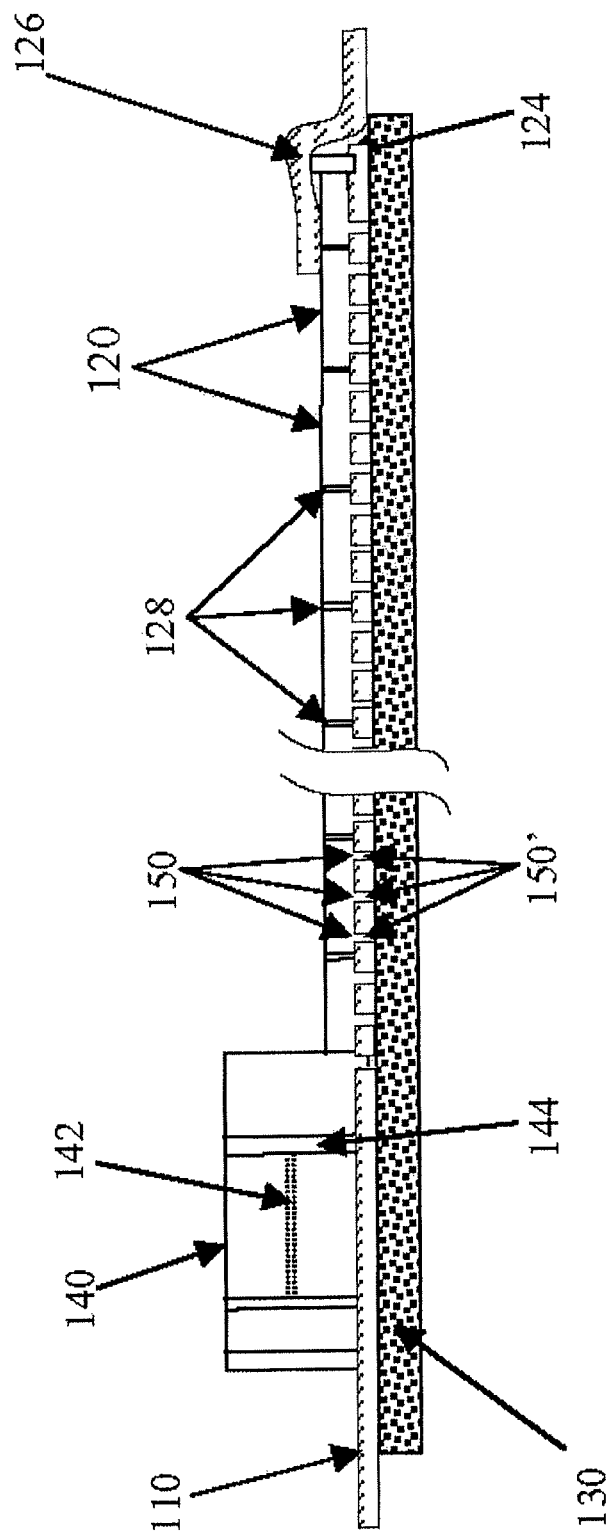

FIGS. 1A and 1B illustrate one embodiment of a static negative pressure device 100. The device 100 comprises a sealant layer 110 (also sometimes referred to herein as a sealant structure) and a collection chamber 120 (also sometimes referred to herein as a collection structure) configured to distribute pressure along a surgical area of tissue trauma, such as the length of a surgical incision. The device is described herein in the context of the tissue being skin, although it should be appreciated that the device can be used with biological tissue other than skin. In some embodiments, the negative pressure therapy device may include a contact layer 130. The contact layer 130 provides fluid communication between the collection chamber 120 and the area of skin trauma. The contact layer 130 may comprise a foam, mesh, gauze, sponge, particulate matter, a stacked mesh matrix, or any other suitable porous biocompatible material, for example. The contact layer 130 may be put into contact with the surface of the surgically closed area of skin trauma. In some instances, the contact layer 130 may be configured to maintain continuity of the air/fluid spaces through the surgical site, which may reduce the occurrence of isolated fluid or air pockets in the enclosed space formed by the surgical area and the sealant layer 110. In some embodiments, the contact layer may be within the borders the skin trauma surface and not contact, overlap or cover the surrounding tissue area adjacent to the skin trauma. In other embodiments, the contact layer may be placed in contact with the adjacent tissue surrounding the skin trauma, in addition to the region of skin trauma itself. As shown in FIG. 1A, the contact layer 130, the sealant layer 110, and the collection chamber 120 may be coupled or integrated together. In some examples, a pre-coupled or integrated design may permit the device 100 to be placed in contact with the skin trauma surface in one step. In some embodiments, the contact layer is placed in contact with the skin trauma surface. Once positioned, the contact layer is then covered by the sealant layer with an integrated collection chamber to form a sealed enclosure or space. In some embodiments, the sealant layer may be affixed to the area of skin surrounding the trauma area by any suitable materials or mechanisms known to one skilled in the art, including but not limited to, tape, glue, or a suitable biocompatible adhesive product.

Further depicted in FIG. 1A is one example of a suction apparatus 140. The suction apparatus 140 may be configured to create a level of reduced pressure inside of the collection chamber 120. In some embodiments, the collection chamber 120 may be in a pre-evacuated state prior to being positioned on the surface of the skin trauma, while in other embodiments, the collection chamber 120 may be evacuated after positioning, or after coupling to the suction apparatus 140. The collection chamber 120 may be pre-evacuated at the point-of-use or at the point-of-manufacture. In some embodiments, the suction apparatus may be coupled to the collection chamber prior to being positioned on the surface of the skin trauma, and in still other embodiments, the suction apparatus and the collection chamber may be integrally formed. In some embodiments the collection chamber may be sized to the length of the surgically closed area of skin trauma by cutting the collection chamber or by detaching or one or more portions of the collection chamber. In some configurations, the collection chamber may have one or more pre-defined separation zones with reduced thickness to facilitate length reductions. A suction apparatus can then be attached or otherwise used to close the cut or separated end of the collection chamber. FIG. 1A shows the device 100 with a collection chamber 120 in which a suction apparatus 140 with a constant force spring mechanism 142 has been integrated with the collection chamber 120. When the constant force spring mechanism 142 of the suction apparatus 140 is engaged, the slideable seal or reciprocating mechanism 144 may be drawn back to create and maintain a constant level of pressure inside the sealed enclosure. In FIG. 1A, the device 100 has been sized to the length of a wound by cutting one end 122 of the collection chamber 120. FIG. 1A further depicts the non-suction apparatus end 122 being occluded by an end plug 124. The device is further sealed in FIG. 1A using an end sealant structure 126. The non-suction apparatus end 122 and/or the end plug 124 may be configured to be detachable or non-detachable. For example, a glue may be used to irreversibly attach the end plug to the apparatus end 122.

In some embodiments, the length of the collection chamber may be adjusted based upon the length of the surgical incision or wound. The length of the surgical incision or wound may be generally linear or may be non-linear. In some examples, the length of the collection chamber is about the length of the surgical wound, while in other examples, the collection chamber length may be about +10%, about +20%, about +30% or more, about −10%, about −20%, or about −30% or less than the length of the surgical wound. Although generally elongate surgical wounds are contemplated, in other examples, surgical wounds with non-elongate configuration may also be treated. In some further examples, branching or stellate surgical wounds may be treated, using one or more devices. In other examples, the surgical wound or incision may be characterized as the affected length of a partially dehisced surgical wound. In examples where the surgical wound comprises a partially dehisced surgical incision, the sealant layer and/or contact layer may be configured to seal or cover the dehisced segment, or the entire wound or incision. Exemplary methods for treating non-elongate wounds are described later below. In some examples, the collection chamber per centimeter length may have a volume in the range of about 100 $mm^3$ to about 10,000 $mm^3$ or more, sometimes about 500 $mm^3$ to about 7,000 $mm^3$, and other times about 1,000 $mm^3$ to about 5,000 $mm^3$.

The collection chamber 120 may be in fluid communication with the skin trauma site through the contact layer 130 of the device 100. In some examples, the collection chamber 120 and the sealant layer 110 are integrally formed. As depicted in FIG. 1B, the collection chamber 120 may comprise a plurality of openings 150 that may align or correspond to a plurality of openings 150' in the sealant layer 110 to provide fluid communication between the skin trauma and collection chamber 120 through the contact layer 130 and the sealant layer 110. The series of openings 150 and 150' may permit distribution of the pressure changes applied to the area of skin trauma across the length or region of the skin trauma. The spacing, size or shape of the openings 150 and 150' along the collection chamber 120 and/or the sealant layer 110 may be uniform or non-uniform. In other embodiments, the collection chamber 120 and the sealant layer 110 may comprise separate structures that are configured for coupling. To facilitate alignment of the collection chamber openings 150 with the openings of the sealant layer 110, the adjacent surface of the collection chamber 150 and/or the sealant layer 110 may comprise an adhesive or slip-resistant surface. In other embodiments, the collection chamber openings 150 and/or openings 150' in the sealant layer 120 may form complementary interfit to facilitate alignment. For example, the collection chamber openings 150 and/or the sealant layer openings 150' may protrude into the opening in the corresponding structure. In still other embodiments, the collection chamber openings 150 and the sealant layer openings 150' may comprise complementary sealable snap-fit.

In some examples, the collection chamber may comprise an elastically or plastically deformable material or a bendable configuration. This may permit the collection chamber to conform to the contours of a surgically closed area of skin trauma, and may permit the collection chamber to exhibit at least some conformational change in response to body movement. In one example depicted in FIGS. 1A and 1B, the collection chamber 120 comprises regions or zones of flexible ribbing 128 along the length of the collection chamber 120. The ribbing 128 allows the collection chamber 120 to be shaped and molded by the user and further maintains the user defined configuration. The portions of the collection chamber 120 between the flexible ribbing 128 may be rigid, semi-rigid or flexible. In some further examples, a collection chamber may also be configured to at least partially rotate in addition to bending. In certain examples, different sizes or configurations of openings may be provided around the circumference of the collection chamber and may be selected for use by rotation. The unused opening may be sealed by applying a sealant layer over the unused openings. Alternatively, the openings may be pre-sealed and the selected seals may be utilized by removing the pre-attached seal(s) from them.

FIG. 2 shows another embodiment of a negative pressure therapy device 200 in which the device 200 is configured to be re-evacuated or recharged. The device 200 comprises an integrated contact layer 230, sealant layer 210 and collection chamber 220. The contact layer 230 may be placed in contact with the surface of the skin trauma and a seal may be formed between the skin surrounding the skin trauma using the sealant layer 210. The collection chamber 220 may be integrated with the sealant layer 210 and is in fluid communication with the contact layer and the enclosed surgical site through a series of openings 250 in the collection chamber 220 and the contact layer 230, but in other examples, the collection chamber and the sealant layer may be separate components that may be attached using adhesive or mechanical mechanisms. With separate collection chambers and sealant layers, the alignment of the collection chamber openings and the sealant layer openings may be facilitated by configuring either the collection chamber openings and/or the sealant layer openings with complementary interfit designs. In one alternative embodiment, the base sealant layer may lack pre-formed openings, but the collection chamber openings may comprise sharpened or penetrating structures to permit formation of sealant layer openings when the two components are coupled together.

The collection chamber 220 may be in a pre-evacuated state wherein a level of reduced pressure is already present inside. Alternatively, the collection chamber 220 can be at atmospheric pressure when placed on the patient, and a reduced level of pressure can be created in the collection chamber using an external evacuator device 270, such as a durable medical equipment evacuator or a constant force syringe. The external evacuator device 270 may be positioned in an opening 276 of an evacuator fitting 278 on the collection chamber 220. The evacuator fitting 276 is in fluid communication with the collection chamber 220. The evacuator fitting 276 may be configured as a one-way flow valve that allows air molecules or other materials to be removed from the collection chamber 220 while resisting entry of air molecules or other materials into the collection chamber. In the particular examples illustrated in FIG. 2, the collection chamber 220 comprises flexion regions 228 with ribbing, but in other examples, a substantial length of the collection chamber comprises a flexible material.

FIG. 2 also depicts a collection chamber 220 with one end 222 occluded with an end plug 224. The other end 222' of the collection chamber may be fitted with a one-way flow valve 260. Thus, the device 200 may comprise a separate one-way flow valve 260 for facilitating the emptying of the collection chamber 220 when the collection chamber 220 is filled with exudate or other matter. Once the collection chamber 220 has been emptied, the collection chamber can then be re-evacuated using an external evacuator 270 introduced through the opening 276 of the evacuator fitting 278. In some embodiments, the one-way flow valve 260 and the means for evacuating the collection chamber 220 are the same structure. In some embodiments, the one-way flow valve and the means for evacuating the collection chamber are two different structures, as shown in FIG. 2. FIG. 2 also shows a device 200 with a moldable collection chamber 220.

Figure 3:
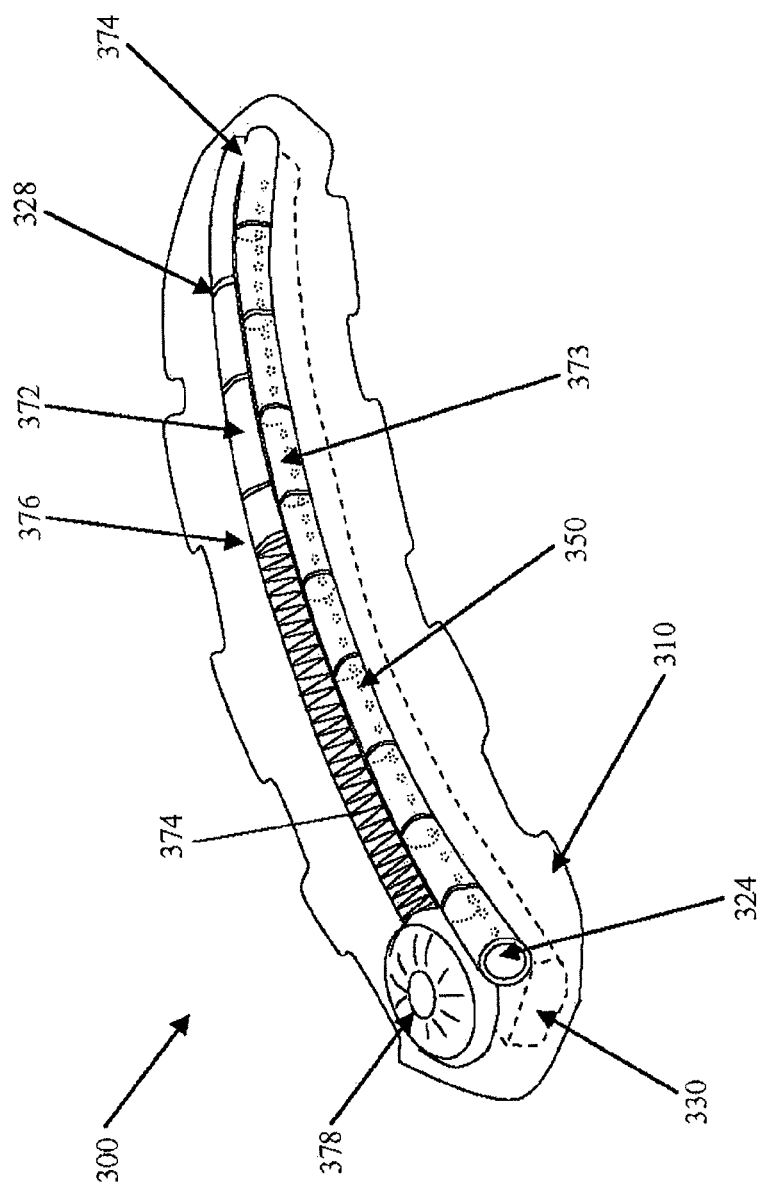
FIG. 3 depicts an embodiment of the negative pressure therapy device as viewed from above in which the collection chamber is a segmented collection chamber.

Another example of a negative pressure therapy device 300 is shown in FIG. 3. The negative pressure therapy device 300 may comprise a multi-chamber collection system 370, comprising a first chamber 372 and a second chamber 373. The multiple chambers may be connected, or may be separate. In FIG. 3, for example the first and second chambers 372 and 373 may be in fluid communication with each other at an interconnecting opening 374. The first chamber 373 of the dual chamber collection chamber 370 has a series of openings 350 that are configured to provide fluid communication with the contact layer 330 of the device 300. The second chamber 372 of the dual chamber collection chamber 370 can be fitted with a reciprocating mechanism for regulating pressure. In FIG. 3, the second chamber the reciprocating mechanism is shown as a spring 374 attached to a spring housing 378 on the end of the dual chamber collection chamber 370 opposite to the sealed end with end plug 324. The spring creates a moving seal 376 through the use of a plunger like apparatus. The moving seal 376 self-regulates changes in pressure in the dual chamber collection chamber 370 and moves in response to these changes.

Figure 4:
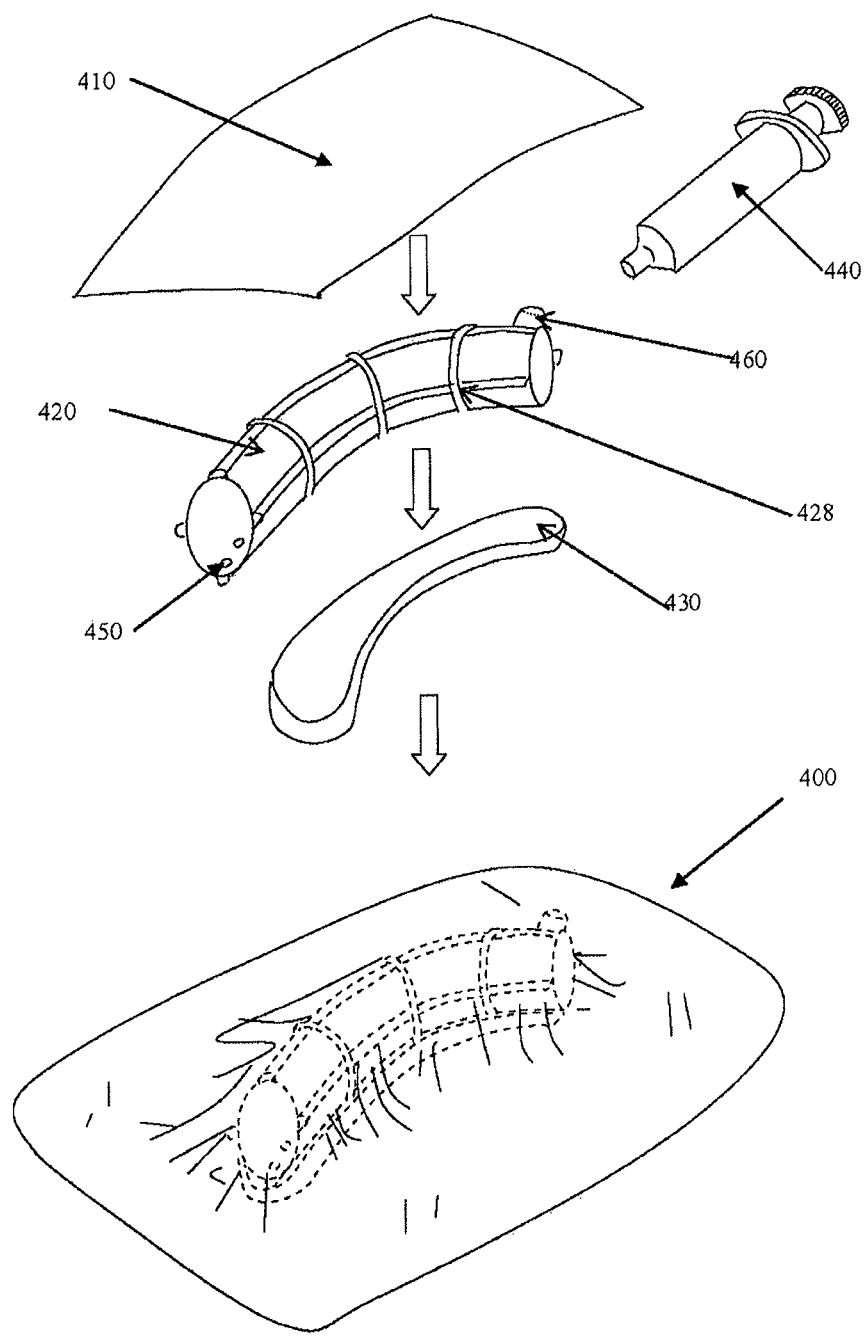
FIG. 4 depicts an embodiment of the negative pressure therapy device in which an occlusive layer is placed over the collection chamber.

FIG. 4 illustrates another embodiment of a negative pressure therapy device 400, in which contact layer 430, the collection chamber 420, and the sealant layer 410 of the device are not integrated and the sealant layer 410 is placed above or over the collection chamber 420 and contact layer 430. In this embodiment, the contact layer 430 is placed in contact with the surgically closed area of skin trauma. A moldable collection chamber 420 with ribbing 428 may be used to manipulate the configuration of the chamber 420 for contact and coverage with the contact layer 430. A series of openings 450 located in the collection chamber 420 provides for fluid communication between the contact layer 430 and the collection chamber 420. The collection chamber 420, once in contact with the contact layer 430, may then be evacuated through the use of suction apparatus 440. The suction apparatus can be a syringe, a powered pump, a Venturi system, a forced expansion device, constant force spring device, or a static negative pressure device, or any suitable active or passive suction source. The suction apparatus 440 is preferably in fluid communication with the collection chamber 420 through a one-way valve 460. After the collection chamber 420 is evacuated, a sealant layer 410 can then be placed over the collection chamber 420 and the contact layer 430 to form a sealed enclosure with the wound.

Figure 5:
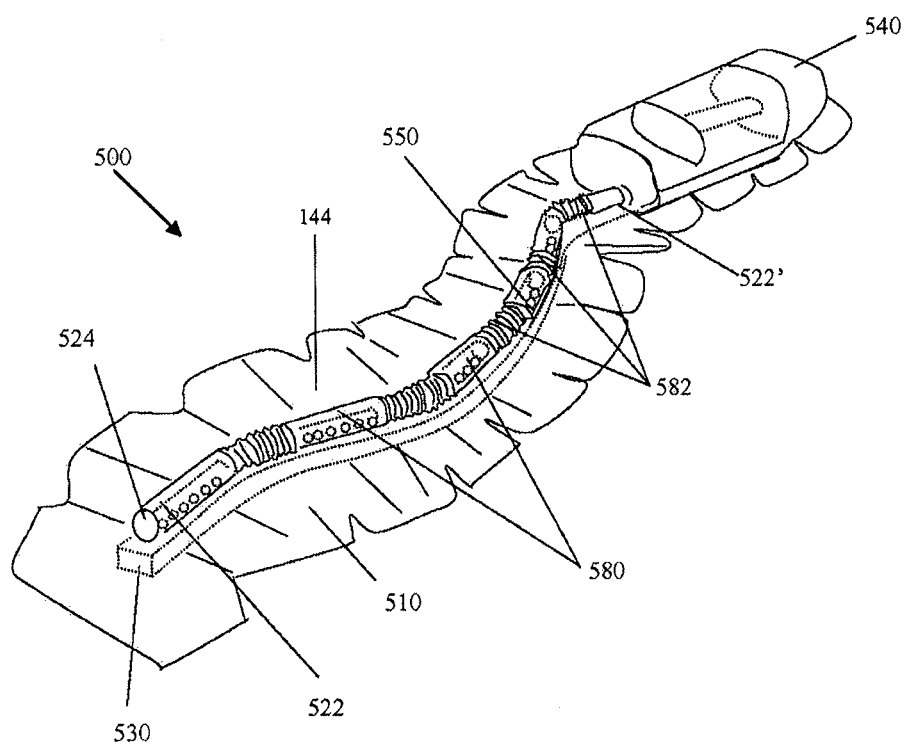
FIG. 5 depicts an embodiment of the negative pressure therapy device in which the collection chamber comprises corrugated tubing segments interspersed with discrete collection members.

FIG. 5 depicts another embodiment of a device 500, in which the collection chamber 520 comprises corrugated tubing segments 582 with discrete collection members 580 interspersed throughout the collection chamber 520. One end 522 of the corrugated tubing is sealed with an end plug 524 or other closed configuration. The other end 522' of the device 500 may be coupled or integral with a suction source 540, such as a syringe, a powered pump, a Venturi system, a forced expansion device, constant force spring device, a static negative pressure device, or a durable medical equipment evacuator, or any suitable active or passive suction source such as for example that described in U.S. Patent Application Publication No. 2010-0042021, which is incorporated by reference herein in its entirety. The contact layer 530 of the device 500 is integrated with the sealant layer 510 and the collection chamber 520 in FIG. 5. Once placed on the patient, the corrugated tubing segments 582 allow the collection chamber to conform to the surface topology of the patient. This embodiment of the device allows the device to move with the patient. The corrugated tubing segments allows for significant expansion and compression of the underlying skin. In an embodiment where the collection chamber is a corrugated tube with discrete collection members, the discrete collection member 580 are in preferably fluid communication with the contact layer 530 and skin trauma surface through a series of discrete openings 550.

In some embodiments, an elongate reduced pressure therapy system may be applied along the length of an elongate wound with wound edges that may be approximated. The elongate reduced pressure therapy system may also be used with incisions already closed by sutures, staples or adhesives, for example. In some instances, the use of a reduced pressure therapy system on a closed incision may provide more uniform force distribution along an incision, by exerting additional closure forces against tissues not immediately contacting a suture or staple, for example. A negative pressure therapy system, in some instances, may also resist separation of the wound edges. In some instances, the negative pressure therapy system may resist stretching of the newly formed connective tissue, which may reduce the extent of scarring. In some examples, by applying a sealant layer and reducing the pressure, the approximation of the wound edges may be further augmented by collapsing the potential space between the edges. In some particular embodiments, the wound treatment system may comprise a negative pressure system that is configured to provide both mechanical tension reduction and reduced pressure effects on the incision or wound. The reduced pressure effects may or may not include the displacement of the wound edges toward each other by reducing the pressure of the space between the wound edges and/or from pushing or pulling by the sealant layer as the sealant layer is contracted around the support. A reduced pressure therapy system may also comprise an elastic sealing layer or a sealing layer configured with one or more elastic members. In use, the sealant layer may be attached or adhered to one side of the incision or wound and then stretched and attached to the other side of the incision or wound. Once in place and with the stretching force relieved, the sealant layer or its elastic member may exert opposing forces on each side of the wound to augment the edge approximation and draw the incision or wound edges together. In some examples, the elastic members may be oriented in a transverse position to the longitudinal orientation of the incision or wound, but in other examples, the elastic member may be oriented in multiple directions. The sealant layer or the elastic member may comprise a material such as silicone rubber, silicone elastomer, polyisoprene or other elastomeric material which possesses a sufficient restoring force to pull tissue together when adhered to opposing incision or wound edges in a stretched configuration. In some examples, one or more elastic members may be applied or attached to the sealant layer after the sealant layer has been applied to the incision site or wound site.

Figure 6A:
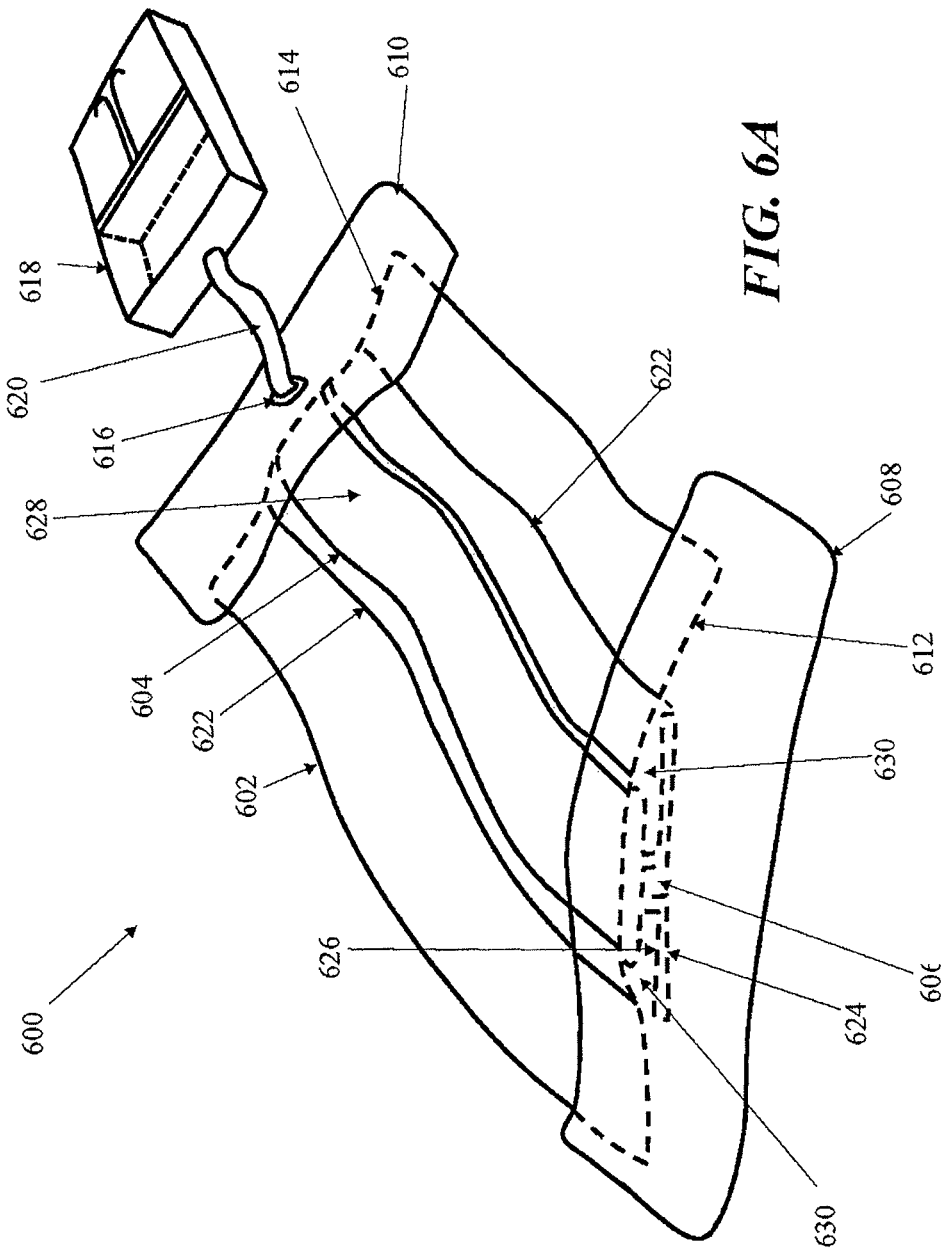
FIG. 6A is a perspective view of another embodiment of a negative pressure therapy device.
Figure 6B:
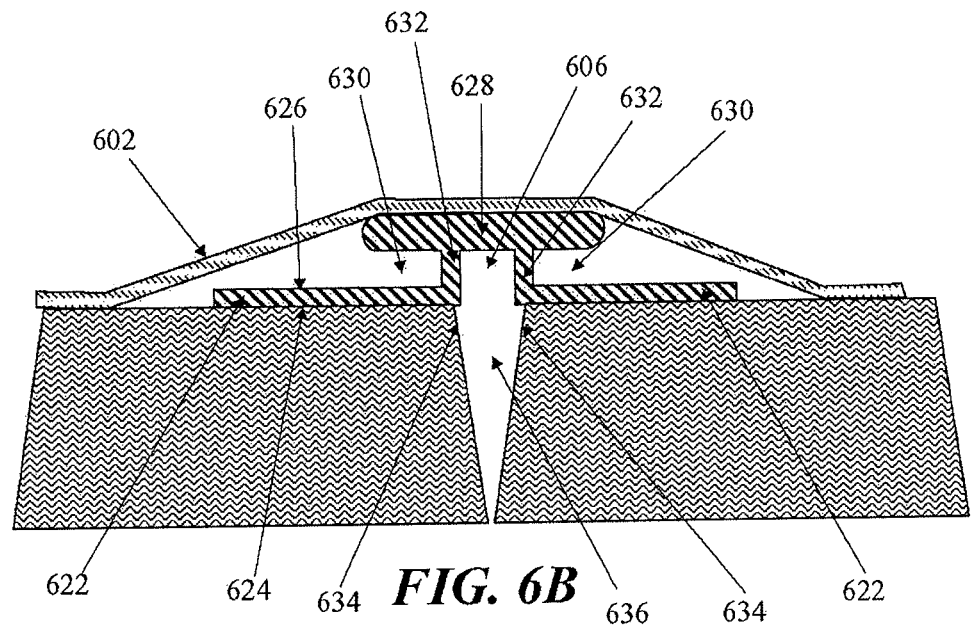
FIGS. 6B and 6C are axial cross-sectional views of the device in FIG. 6A, before and after the application of reduced pressure, respectively.
Figure 6C:
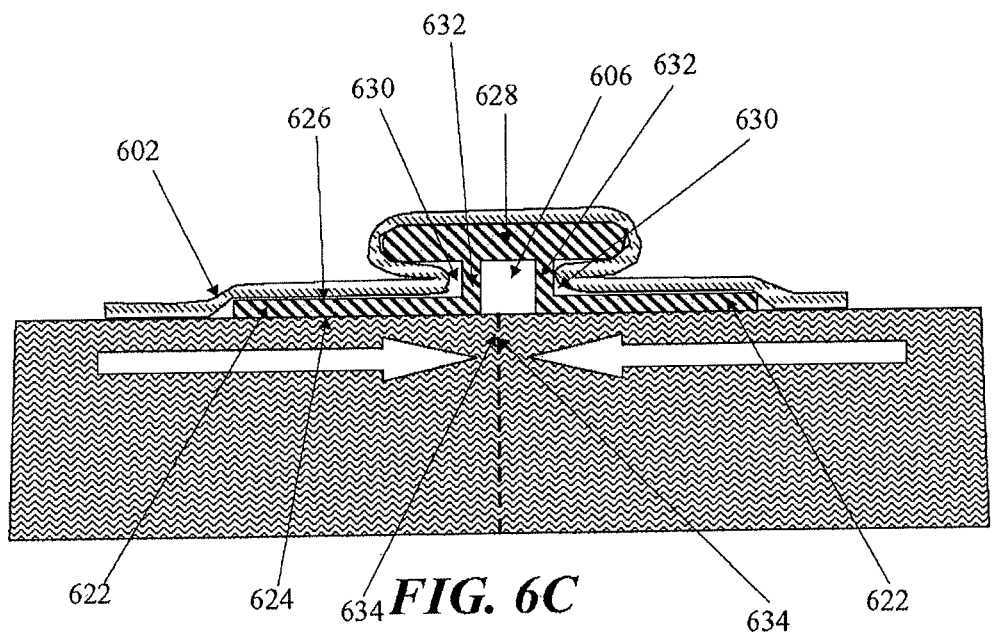

FIGS. 6A to 6C depict another example of a wound treatment device 600 comprising a sealant layer 602 and an elongate support 604. The elongate support 604 may be configured with an elongate central channel 606 that may be placed along or over an incision or elongate wound. In some configurations, the device 600 may comprise multiple channels in direct communication with the elongate wound. In this particular example, the elongate central channel 606 has an open channel configuration that is exposed to the incision or wound along a portion if not all of its longitudinal length, but in other examples, the elongate channel 606 may have a generally closed configuration with a plurality of longitudinally arranged openings along a segment of the channel or the entire channel. An open channel or a plurality of longitudinally arranged openings may permit the application of reduced pressure along a length of the wound while possibly reducing the risk that clogging or transient opposition of tissue surfaces may affect the distribution of pressure reduction and/or fluid suction. In some examples, the channel, or the segment of the channel in communication with the incision or wound, may have a length of at least about 1 cm or more, 3 cm or more, sometimes about 10 cm or more, and other times about 20 or about 50 cm or more. In some examples, the device 600 may comprise a length of about 70 cm, 100 cm or even 150 cm, which may be cut or shortened to a smaller length. In some embodiments comprising a flexible, bendable and/or moldable support 604, the support 604 and/or sealant layer 602 may be provided in the form of a roll or a folded form, which is then dispensed and cut as needed. The device in the rolled configuration provides a more compact configuration for ease in packaging, handling and application of the device. The device 600 (or other devices described herein) may be used to treat any of a variety of incisions or wounds, but in some specific examples may be used to a variety of elongate incisions or wounds, including but not limited to linear or curvilinear incisions or wounds. These wounds may include but are not limited to any of a variety of traumatic lacerations or cuts, sternotomy incisions, laparotomy incisions, perineal prostatectomy incisions, vein harvesting incisions, C-section incisions, and the like. The devices described herein can be used to treat closed incisions.

In use, the elongate central channel 606 may be positioned along an incision or elongate wound and then secured or sealed by placing the sealant layer 602 over the incision and support 604. The sealant layer 602 and the support 604 may be integrally formed or pre-attached to each other, such that the sealant layer 602 and the support 604 may be applied to an incision or wound in a single step. In some examples, the sealant layer 602 may have a size and configuration to permit complete sealing of the entire perimeter of the incision and the support 604, but in other examples, one or more accessory seals 608 and 610 may be used. The sealant layer 602 may comprise an adhesive on one or more surfaces. In FIG. 6A, for example, adhesive may be provided along the lateral regions the undersurface of the sealant layer 602, leaving a strip or middle section of the sealant layer 602 free of adhesives. In this particular example, end seals 608 and 610 may be used to facilitate sealing about the ends 612 and 614 of the sealant layer 602, but in other embodiments, accessory seals may be used anywhere to provide additional sealing.

In some examples, the sealant layer, support, and/or one or more accessory seals may be pre-configured with a connector or port which may be used to couple the device 600 to a reduced pressure source. In the particular example in FIG. 6A, one of the end seals 610 is pre-configured with a connector 616 that may be used to attach a suction device 618 using an optional connector tube 620. In other examples, the suction source or a connector tube may be configured to pierce and form an aperture through the sealant layer or accessory seal. In still other examples, the suction device 618 may be integrally formed with the end seal, sealant layer and/or support 604.

As shown in FIG. 6B, the support 604 may optionally comprise one or more side flanges or flaps 622 to one or both sides of the elongate channel 606. Each of the side flaps 622 may have a width (or dimension transverse to its longest dimension) in the range of about 2 mm to about 50 mm or more, sometimes about 10 mm to about 40 mm, and other times about 20 mm to about 30 mm. The side flaps may have an average thickness in the range of about 0.5 mm to about 5 mm or more, sometimes about 0.75 mm to about 3 mm, and other times about 1 mm to about 2 mm. The thickness of the side flap may or may not be uniform, and in some examples, the thickness may taper or reduce in a central to peripheral direction, or vice versa. The side flaps 622 may comprise the same or different material as the material about the elongate channel 606. In some embodiments, the support 604 and/or the side flaps 622 may be rigid, semi-rigid or flexible, and may comprise silicone, urethane, or the like, and may or may not comprise a coating. For example, one or more sections of the support 604 may comprise an anti-infective coating, including but not limited to a silver alloy or chlorhexidine coating. The side flaps 622 may or may not comprise an adhesive on its tissue contacting surface 624 and/or its sealant layer contacting surface 626. In some examples, the support 604 may further comprise a cap structure 628. The cap structure 628 may be located on the upper surface of the elongate channel 606 and may be configured to project to one or both sides of the elongate channel 606. The cap structure 628 may project anywhere from about 0 mm to about 15 mm or more, sometimes up to about 5 mm, and other times up to about 10 mm. In some examples, one or more elongate side channels 630 may be formed between the cap structure 628 and the side flanges or flaps 622. The cap structure 628 may comprise rounded edges or surfaces, which may or may not reduce the risk of puncturing or damaging the sealant layer when contracted onto the support 604. In some examples, an accessory seal, or a sealant layer configured with regions of greater thickness, puncture resistance, or other reinforcement may be positioned about the support 604. The side flaps 622 and/or the cap structure 628 may or may not have a symmetrical configuration and/or size with respect to the elongate channel 606. In some configurations, one or more openings may be provided in the walls 632 between the central channel 606 and the side channel(s) 630, but in other configurations, communication between the central channel 606 and the side channel(s) 630 may only occur about the ends of the support 604 where the sealant layer 602 may provide a common space or pocket where it may not be adhered to the skin.

As shown in FIG. 6C, when reduced pressure is applied to the device 600, the sealant layer 602 may collapse around or into the support 604. For example, sections of the sealant layer 602 may be pulled or pushed into the elongate side channels 630. In other examples, the support 604 may comprise any of a variety of indentations, openings, grooves, channels which may permit contraction of the sealant layer 602 to the support 604, either with suction or by mechanical structures such as a clamp or pushrod, drawstring or any other complementary structure that may be attached or coupled to tighten the sealant layer 602 to the support 604. In some instances, this contraction of the sealant layer 602 may or may not draw the wound edges 634 closer together. The application of reduced pressure may also reduce the size or eliminate the gap 636 between the wound edges 634. In such a situation, the application of reduced pressure may result in or otherwise facilitate relief of tension on the wound edges 634. In other embodiments described herein, tension relief is independent or at least substantially independent of the application of reduced pressure.

In addition to the support, the wound treatment system may also comprise one or more elastic elements incorporated or attachable to the sealant layer. For example, elastic bands or threads may be provided in the sealant layer in addition to the elastic properties of the support, if any. In some configurations, the elastic bands or threads may have a uniform orientation, but in other configurations, the elastic bands may be oriented in multiple directions. In some instances, the support may also comprise an elastic material or structure (e.g. a spring) which may be configured to further mechanically bias the wound tissue or edges in a particular direction. In some instances, the spring may comprise an attachable clip, which is optionally used with the support to provide additional force with elastic supports, or the contracting force with rigid supports.

Figure 7:
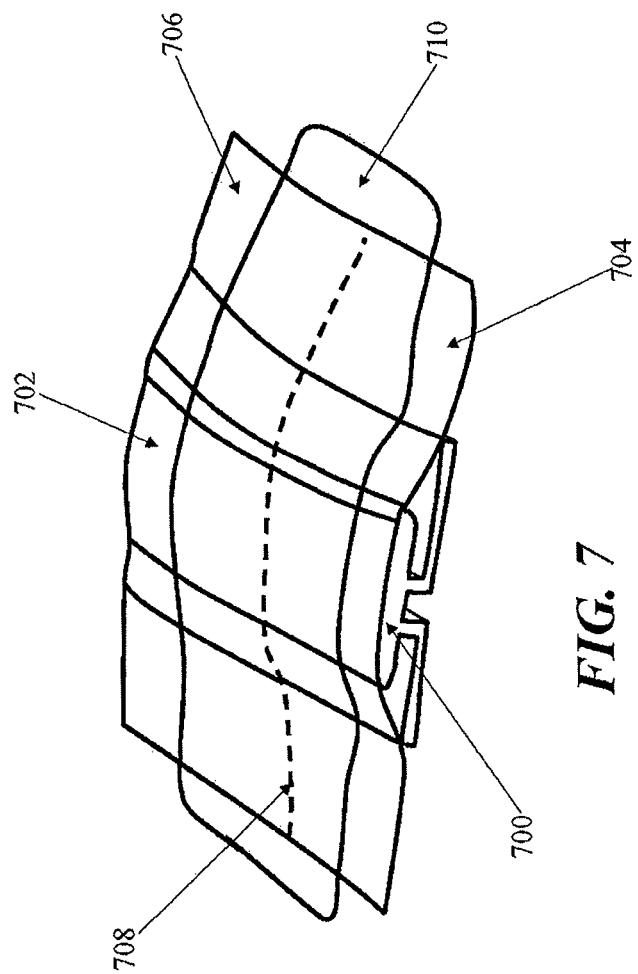
FIG. 7 is a schematic perspective view of two wound coverings joined together.

In some examples, the reduced pressure wound therapy system may be used to treat incisions or elongate wounds that may be longer than the length of the device that is available. In such situations multiple devices, supports and sealant layers may be arranged in an independent or an overlapping configuration to treat larger wounds. In FIG. 7, for example, two separate supports 700 and 702 and sealant layers 704 and 706 are positioned end-to-end and the junction region 708 is covered with a third sealant layer 710. Use of a third sealant layer 710 may be useful, for example, where the support and sealant layer are supplied or manufactured in an integral or pre-attached configuration. Although the ends of the supports 700 and 702 and the sealant layer 704 and 706 are depicted as touching at the junction region 708, in other examples, partial or full gaps may be provided between supports and/or sealant layers. In addition to the serial configuration depicted in FIG. 7, the supports and/or sealant layers may also be arranged in a parallel fashion. In other examples, a third sealant layer need not be used, as one sealant layer may be overlapped over another where the sealant layer extends past the end of it associated support. In other examples, multiple sealant layers or supports may be provided and used with a lesser number of supports or sealant layers, respectively. Also, more than one suction device may be used with longer or larger support or sealant layers.

Figure 8:
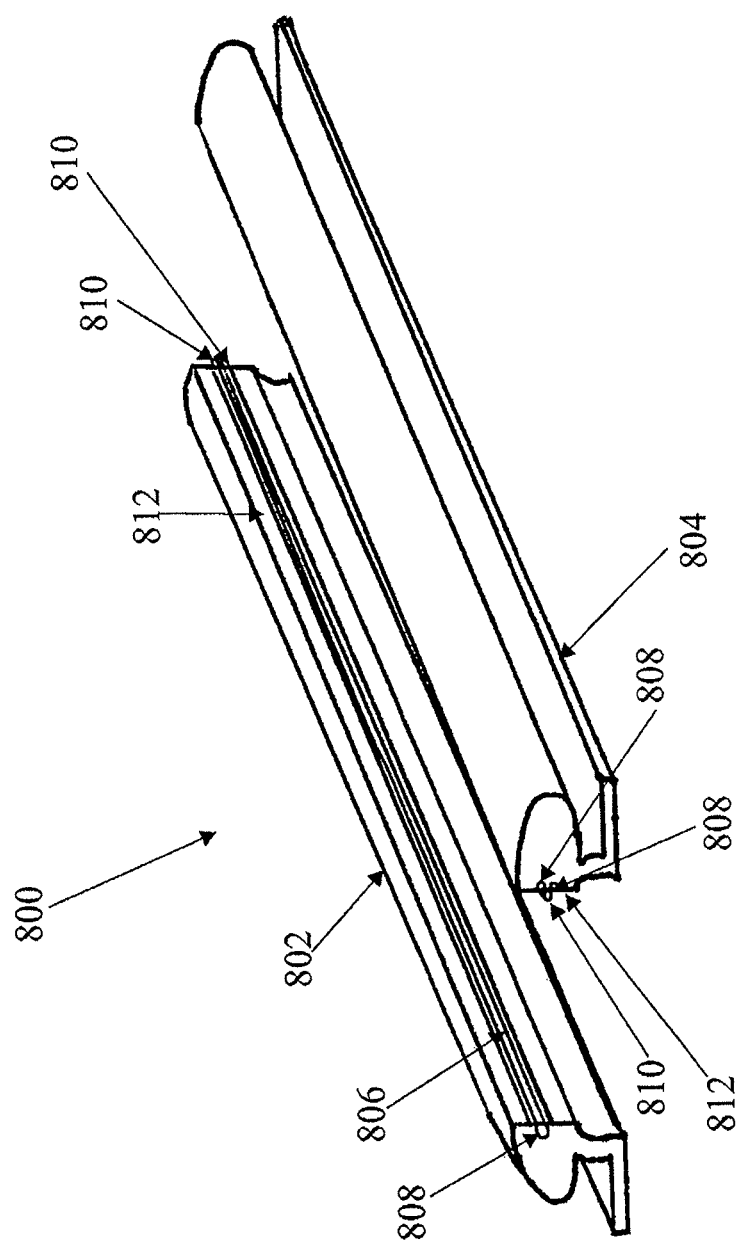
FIG. 8 depicts another embodiment of the negative pressure therapy device, comprising a split support.

In addition to multiple supports that may be arranged in a parallel and/or serial fashion, in some embodiments, the supports themselves may comprise multiple sections that are joined together to form a complete support. In FIG. 8, for example, a support 800 comprise two elongate support segments 802 and 804 which are configured to be generally joined along their longitudinal lengths at a coupling interface 806. A support 800 comprising separate longitudinal segments 802 and 804 may be used to separately attach each segment 802 and 804 to one edge of an incision or wound (e.g. by adhesives or suturing) and are then joined together to approximate the wound edges. In some instances, separate joinable components may be easier to attach to the skin than a unibody support. The longitudinal segments 802 and 804 may be rigid, semi-rigid or flexible, and although the segments 802 and 804 are depicted as each contributing about 50% of the structure, e.g. generally symmetrically split except for possibly the coupling interface. In other examples, however, the longitudinal segments may be asymmetrically split. The coupling interface 806 depicted in FIG. 8 comprises a complementary set of grooves 808 and ridges 810 located along the longitudinal inner surface 812 of each segment 802 and 804, but any of a variety of coupling interfaces 806 may be used, including other snapfits. Other locking interfaces, mechanisms or structures may include but are not limited to resealable adhesive layers, slide locks, hinge clamps, clips, locking pins with lockable lumens, zippers, elastic binding bands, and the like. In some examples, structures that may be used to contract the sealant layer into a unibody support may also be used to contract the sealant layer into a multi-segment support and/or to couple the segments of a multi-segment support together.

Figure 9A:
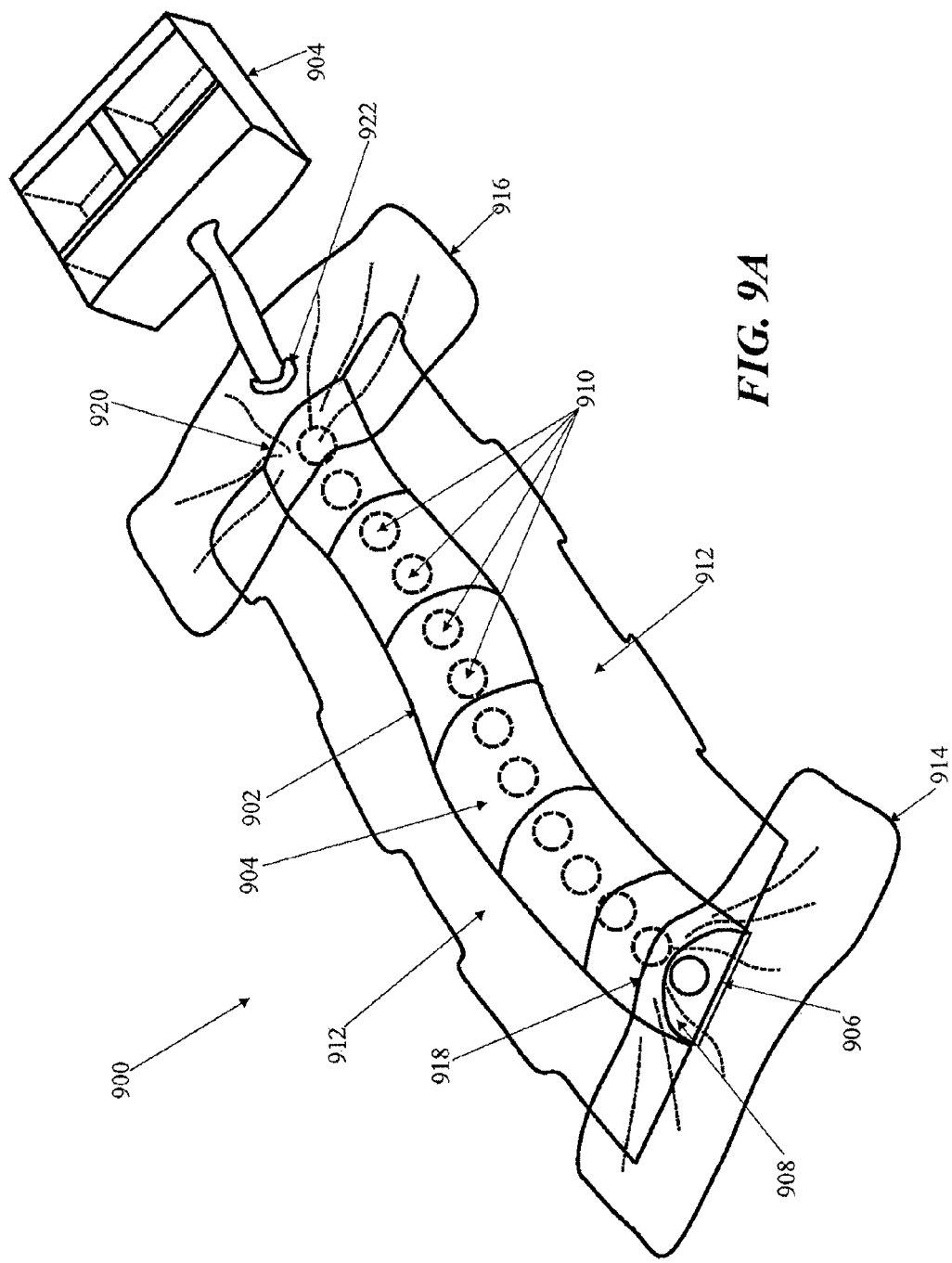
FIG. 9A is a perspective view of another embodiment of a negative pressure therapy device comprising an elastic collection channel.

FIG. 9A depicts one example of a negative pressure therapy system 900 comprising an elastic support 902 and an optional suction system 904. An optional contact layer 906 may be provided under the elastic support 902. The elastic support 902 is configured with one or more longitudinal conduits 908 or channels. The conduit or channel may be fully enclosed or may be at least partially open. The conduit 908 in FIG. 9A has a closed configuration with a plurality of apertures 910 to permit air or fluid communication with the underlying wound or incision. In this particular example, the lateral flaps 912 of the elastic support 904 may comprise an adhesive, which may be used to at least seal a portion of the conduit 908 and the external space, if any, between the incision or wound and the apertures 910. In some other examples, the lateral flaps 912 may extend to one or both ends of the support, but in the example, depicted in FIG. 9A, end seals 914 and/or 916 may be used to facilitate sealing about the ends 918 and 920 of the support 902. As mentioned previously, at least one of the end seals 916 may be provided with a connector 922 for attachment of the suction system 904, but in other embodiments, the connector may be located on the elastic support 902. In still other examples, a large sealant layer may be used to cover a larger portion if not all of the support, and with or without a protective layer. For example, some embodiments of the elastic support may comprise segmented non-sealing lateral flaps which are configured to elastically bring wound edges together. The segmentation may facilitate the application of the elastic support in a sectional manner, but may or may not provide sealing ability, such that a sealant layer applied over the elastic support may be used to provide a sealed space about the support.

Figure 9E:
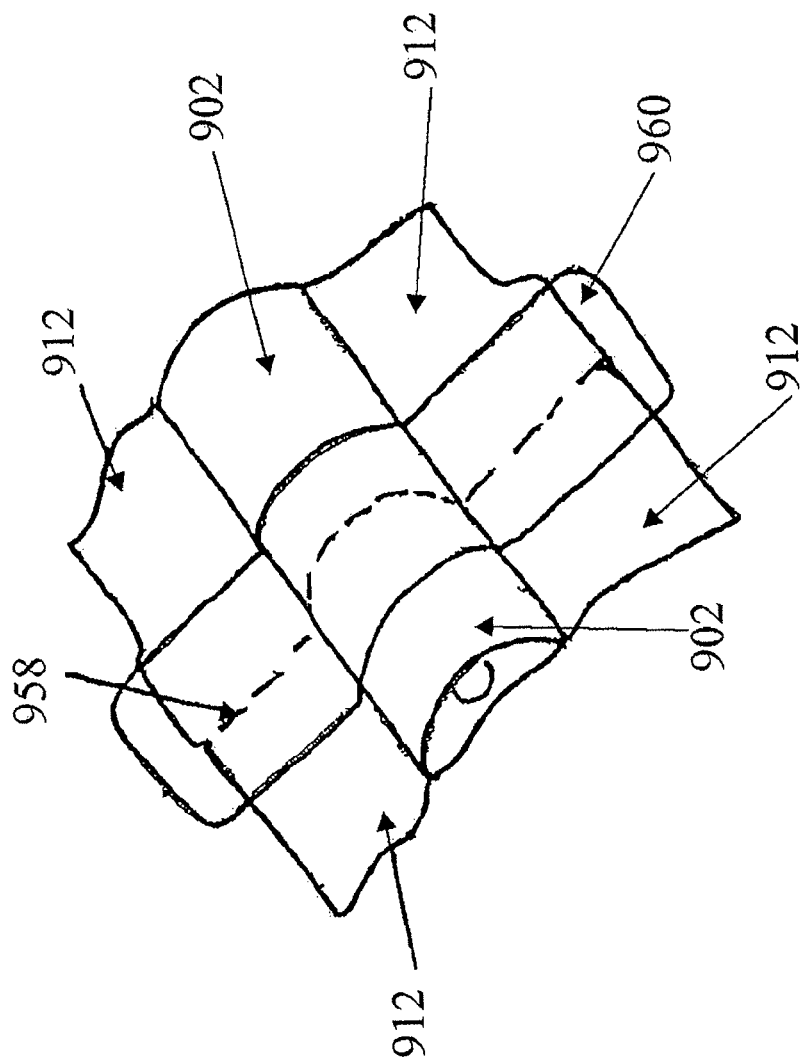
FIG. 9E is a schematic perspective view of two negative pressure therapy devices joined together.

Referring to FIGS. 9B to 9D, in use, the flaps 912 of the elastic support 902 may be elastically stretched or pulled away from each other and applied in its stretched state to the incision or wound such that each flap 912 is adhered to the skin surface 922 to a respective edge of the incision or wound. In some procedures, the support 902 may be sufficiently stiff or rigid such that a substantial longitudinal length of the flaps 912 can be stretched, but in other configurations, a smaller portion of the flaps 912 may be pulled away, which may facilitate the application of the support to non-linear incisions or wound by permitting adherence or attachment of the support section-by-section. Once adhered to the skin surface 920, the stretching or deformation force may be relieved, and the elasticity or bias in the support 904 may push the wound edges 922 toward each other. Once fully sealed, the suction source 904 may be activated to reduce the pressure in the conduit 906 and/or to remove air or fluid from the incision or wound, which may or may not further reduce the gap 924, if any, between the wound edges 922, in addition to providing a reduced pressure to enhance healing and/or to evacuate potential fluid pockets. FIG. 9E depicts how two elastic supports 902 with flaps 912 may be positioned serially or in an end-to-end fashion to treat incisions or wounds having a longer length by covering the junction 958 with an accessory seal 960. As noted previously, although the ends of the supports 902 and their flaps 912 are depicted as touching at the junction region 958, in other examples, partial or full gaps may be provided between supports and/or their flaps.

The elastic support may comprise any of a variety of configurations. As depicted in FIGS. 9B to 9D, the elastic support 902 may comprise an elastomeric member 926 which may augment the elastomeric properties, if any, of the flaps 912 and/or wall 928 of the conduit 908. As further illustrated, the apertures 910 of the elastic support 902 may be provided directly in the elastomeric member 926, and in some configurations the apertures 910 may also deform in shape when force is applied to the flaps 912. FIG. 10A to 10C depicts another embodiment of an elastic support 950 with flaps 952, wherein the apertures 954 are provided in a non-elastic structure 956. Thus, when the elastomeric member 958 is stretched, the apertures 954 maintain the same configuration. The non-elastic structure 956 may have any of a variety of configurations, including rings or frames, and may form either a partial or a complete perimeter of the aperture 954. The non-elastic structures 956 may be separate for each aperture 954 or they may be interconnected. FIG. 11A to 11C depicts still another embodiment of an elastic support 970 with flaps 972 comprising an elastic material such that a specific elastomeric member is not used. In this particular embodiment, the elastic support 970 comprises an open channel 974 that lacks discrete apertures and instead is generally open along the length of the channel 974 to the edges 922 and space 924 of the underlying incision or wound. As shown in FIGS. 11A to 11C, the elastic support 970 may be applied to an incision 976 closed with sutures 978 or other type of incision closure such as staples. The sutures 978 may be any type of suture and may be used with any of a variety of suture techniques, including running sutures and interrupted sutures. In some variations, although the sutures 978 may generally maintain the approximation of the wound edges 980, separation forces acting at the sutures 978 may generate focal regions of tissue tension. Application of the elastic support 970 to the incision may be used to apply additional contiguous force along a substantial length of the incision 976, which may or may not reduce the focal tissue tension and possibly improve incision healing.

Figure 12:
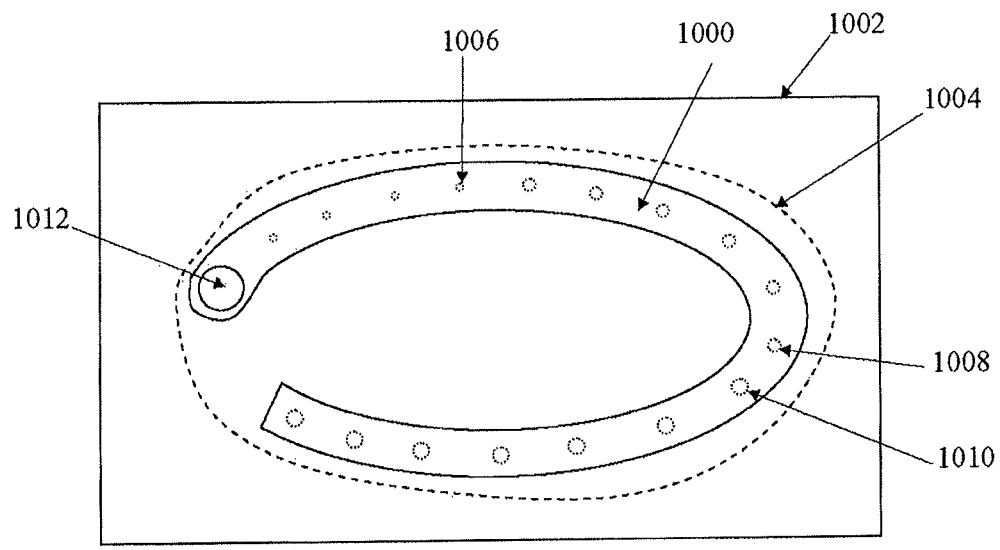
FIG. 12 is a schematic illustration of an elongate negative pressure therapy system arranged around a perimeter of a wound.

In other embodiments, the devices described herein may also be used to treat non-elongate incisions or wounds. FIGS. 12 to 15 depict various examples of using an elongate negative pressure therapy system to treat non-elongate wounds. In FIG. 12, for example, an elongate negative pressure therapy device 1000 and a sealant layer 1002 are positioned around the perimeter of wound 1004. As further illustrated in this example, the device 1000 may comprise apertures 1006, 1008 and 1010 of varying size. In some instances, smaller apertures 1004 may be used at distances closer to the suction source or interface 1012, while larger apertures 1008 may be used at relatively farther distances. In still other examples, the size of the apertures may be uniform, but either the number and/or the spacing of the apertures may vary along the longitudinal length of the device.

Figure 13:
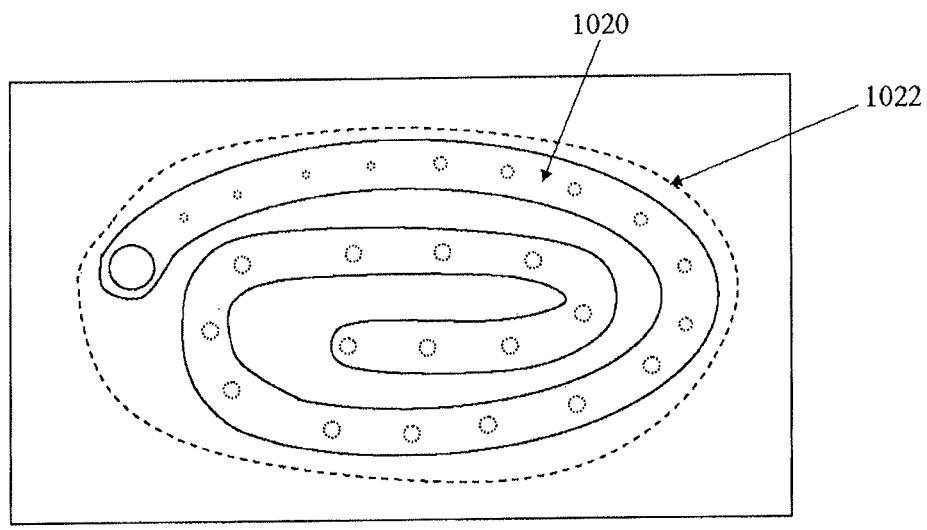
FIG. 13 is schematic illustration of an elongate negative pressure therapy system arranged in a spiral orientation about a wound.
Figure 14:
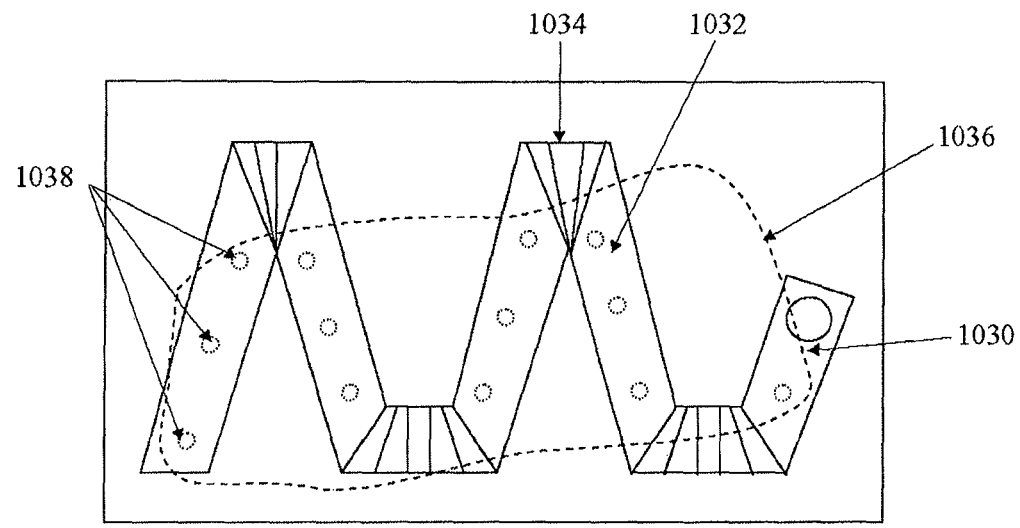
FIG. 14 is schematic illustration of an elongate negative pressure therapy system arranged in a zig-zag orientation about a wound.

FIG. 13 depicts another example of a negative pressure therapy device 1020 arranged in a spiral orientation with respect to a wound 1022. In some instances, the spiral orientation may augment the pressure or suction about the center of the wound 1022, compared to the device arrangement depicted in FIG. 12. FIG. 14 is still another example of a device 1030 comprising alternating rigid sections 1032 and flexion sections 1034 arranged in a back-and-forth or zig-zag orientation along a non-elongate wound 1036. As mentioned previously, in some examples, the rigid sections 1032 may also rotate with respect to the flexion section 1034 or other articulation of the device. As shown in FIG. 13, the device need not be fully located within the borders of the wound 1036, and although all of the device apertures 1038 are located within the wound borders, in other examples one or more apertures may be located outside the border of the wound.

Figure 15:
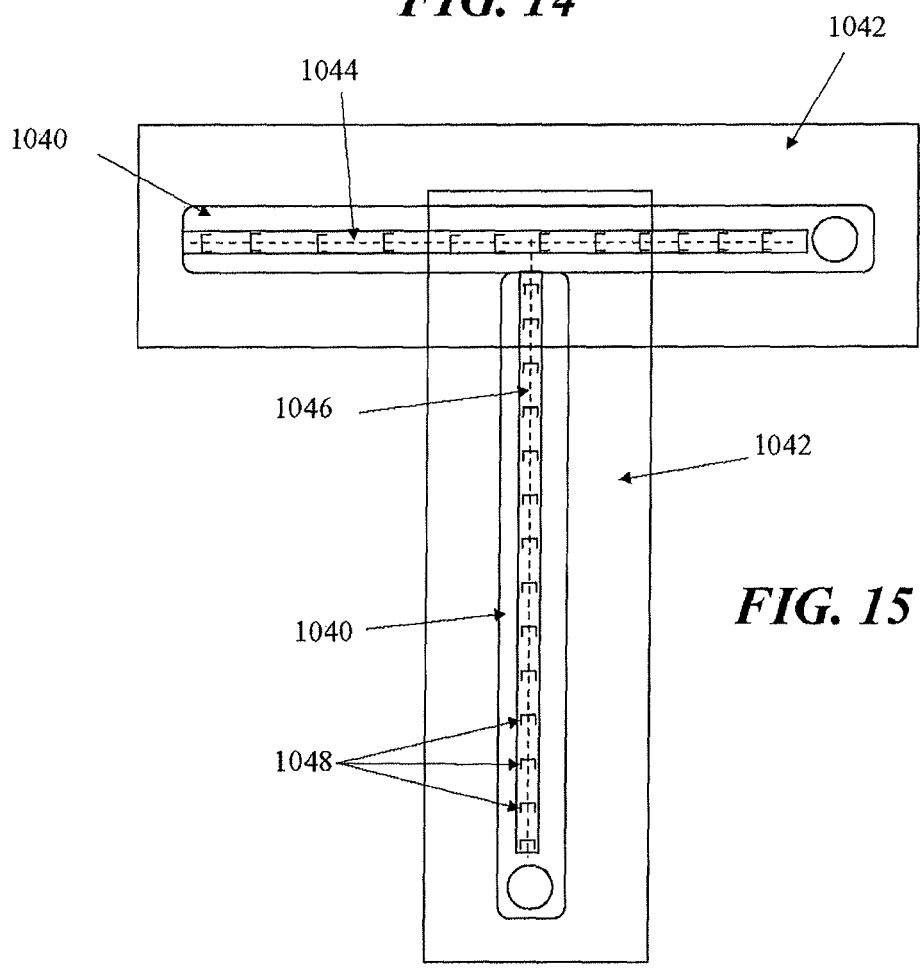
FIG. 15 is schematic illustration of an elongate negative pressure therapy system arranged in a T-orientation about a wound.

FIG. 15 depicts another example where multiple devices 1040 and sealant layers 1042 are used to close a non-linear surgical incision. In this particular embodiment, the surgical incision comprising a T-incision with a transverse incision 1044 and a midline incision 1046, and is treated using two open-channel devices 1040 applied to each incision 1044 and 1046, with overlapping sealant layers 1042. In other examples, more than two devices and two sealant layers may be used, e.g. one longer device may be used along the entire length of the midline incision 1046 and two smaller devices may be used along each remaining segment of the transverse incision 1044. In some instances, open channel devices 1040 may be used when surgical close is performed with staples 1048 or any other protruding closure component.

In some cases, the opposing edges of a surgically closed incision may tend to pull apart because of underlying mechanical load present in the tissue. This tension may be due to naturally occurring skin tension or induced after tissue excisions or due to normal body motion, for example. Mitigation of the tissue tension may improve healing of the closed incision and/or reduce scarring or other undesirable cosmetic effects. The devices described herein are configured to impart a force onto the tissue to relieve tension on the skin and reduce the likelihood of the closed incision moving apart. The devices may include one or more structures that permit the user to control the force imparted on the tissue.

The devices described herein also shield the area of skin trauma from external stresses that may be imparted to the body. The devices can shield the area of skin trauma from endogenous stress originating from the skin itself (e.g., stress transferred to the wound via the stratum corneum, epidermal or dermal tissue), and/or exogenous stress (e.g., stress transferred to the wound via physical body movement or muscle action). In some variations, the devices shield the area of skin trauma from endogenous stress without affecting exogenous stress on the area of skin trauma, e.g., devices that modify the elastic properties of the skin, etc. In other variations, the devices shield the area of skin trauma from exogenous stress without affecting endogenous stress on the area of skin trauma. Such variations can include situations where the musculature and surrounding wound tissue has been paralyzed, e.g., through the use of botulinum toxin or the like. In still other variations, the devices shield the area of skin trauma from both endogenous and exogenous stress.

In some examples, the application of negative pressure to a wound may cause contraction of the sealant layer adhered to the tissue surrounding the wound, which may offset at least a portion of any wound tension that may cause wound edge separation or dehiscence. In further examples, the sealant layer may be configured to provide mechanical tension relief across the closed incision. The sealant layer may be configured to be adhered to the skin in a state wherein there is residual tension in the sealant layer in the direction substantially transverse to the closed incision. Once the sealant layer is adhered to the skin, the residual tension in the sealant layer will be transferred to the skin, and may cause the sealant layer to tend to contract along the direction of the residual tension. This may impart transverse compressive stresses on the closed incision, which may oppose the tendency of the opposing edges of the closed incision to pull apart. These applied stresses may partially reduce the tensile stresses, make the net stresses zero or induce compressive stresses across the wound.

The sealant layer may comprise one or more mechanical elements which increase the residual tension in the sealant layer prior to application. For example, the sealant layer may comprise mechanisms limiting compression applied to the closed incision. The sealant layer may also comprise handling tabs on the edges or other regions of the sealant layer which may be held by the user and stretched apart prior to and during application, imparting tension into the sealant layer. The sealant layer may also be applied whereby compression of tissue occurs in a secondary step that mechanically draws or brings the skin on each side of the closed incision together. In some configurations, the tension in the sealant layer may be applied with a removable element that stretches the sealant layer before and during application. After application, the removable element may be removed to allow the sealant layer to impart stress to the application site.

In these embodiments, the sealant layer may further comprise stretch-limiting elements or structures which would reduce or prevent the user from applying excessive stretch to the sealant layer. In some instances, certain levels of stress may compromise sealant layer integrity, apply excessive shear stress to the skin surface and/or apply excessive compressive stress to the wound. In one example, the stretch-limiting elements of the sealant layer may comprise elongate elements or fibrous strands positioned transversely across the sealant layer. The elongate elements may be in a slack or non-tension state when the sealant layer is unstretched. Once the sealant layer has been stretched to a particular size or to a given limit, the slack on elongate elements will be reduced or eliminated and the fibrous strands will provide a resistance to further stretching. In an alternate example, the stretch-limiting elements may comprise a substantially inelastic film that is initially slack that becomes taut during stretching of the sealant layer, thereby reducing or preventing over-stretching of other structures or materials comprising the sealant layer or structure.

In further embodiments, the sealant layer may comprise visual guides which provide feedback or cues to the user concerning the amount of tension imparted to the sealant layer. For example, the sealant layer may comprise a plurality of substantially parallel longitudinal markings. As the user stretches the sealant layer, the distance between the markings will increase which will be visually apparent to the user. An index or guide may also be provided which depicts spacing of markings at given tension levels which the user may use for a visual comparison. The index or guide may be integrally formed with the sealant layer, or may be provided as a separate device or even on the packaging of the sealant layer. In another embodiment, the visual guide may comprise a region or plurality of regions of pigmentation or coloration in the sealant layer which are substantially transparent or translucent. As tension is applied to the sealant layer, the thickness of the sealant layer will decrease or increase the perceived transparency or translucency of the colored or pigmented regions. In another embodiment, the visual guide may comprise region or plurality of regions of coloration which will shift color with increasing tension.

In some embodiments, the mechanisms limiting compression may comprise displacement limiters. For example, the contraction of the sealant layer may be limited by the presence of at least two structures or sets of structures that produce mechanical interference that may limit the degree of tissue compression or displacement. In some further examples, the structures may mate in an interlocking fashion. For example, one structure may be positioned near the centerline of the sealant layer while another corresponding or complementary structure may be positioned further from the centerline of the sealant layer. Once the device is applied, the residual tension in the sealant layer will cause the sealant layer to contract, which will bring the complementary structures in proximity with one another to the point where they will interlock, mate or otherwise contact. Once contact between said opposing structures has occurred, further contraction of the sealant layer is restricted and thus the degree of compression applied to the closed incision is limited.

In other embodiments, the sealant layer may comprise a carrier structure, such as a carrier film which is removably attached to the sealant layer on the side opposite to the side of the sealant layer bearing the adhesive. The carrier structure, when attached, will maintain the sealant layer in tension and prevent contraction of the sealant layer. In use, the device is applied to the skin with the carrier structure attached to the sealant layer. Once adhered to the skin, the carrier structure is removed, allowing the tension in the sealant layer to be at least partially released and transferred to the skin. In some embodiments, the carrier structure is anisotropically flexible such that it is substantially rigid in the transverse direction to maintain tension in the sealant layer in that direction, but substantially flexible in the longitudinal direction to allow the device to conform to the patient's body. In further embodiments, the carrier structure comprises transverse ribs which provide this anisotropic flexibility. In further embodiments, the carrier structure is configured to be foldable such that the device is stored in a relaxed state until tension is required for application at which time the structure is unfolded and tension is imparted to the sealant layer.

In some embodiments, the device may be configured to deliver one or more therapeutic agents. These agents may include but are not limited, for example, antibiotics and anti-inflammatory agents, which may improve healing of the closed incision. In some embodiments, the device may comprise additional chambers or tubular structures in addition to the primary collection chamber. The additional chambers or tubular structures may be configured to be in fluid communication with a source of therapeutic agents, which may include an external pump or gravity-fed drip source. In some embodiments, the additional chambers or tubular structures are not in direct fluid communication with the primary collection chamber. In some embodiments, the additional chambers or tubular structures further comprise a separate passageway or a plurality of passageways which allow delivery of the agents to the closed incision.

Figure 16A:
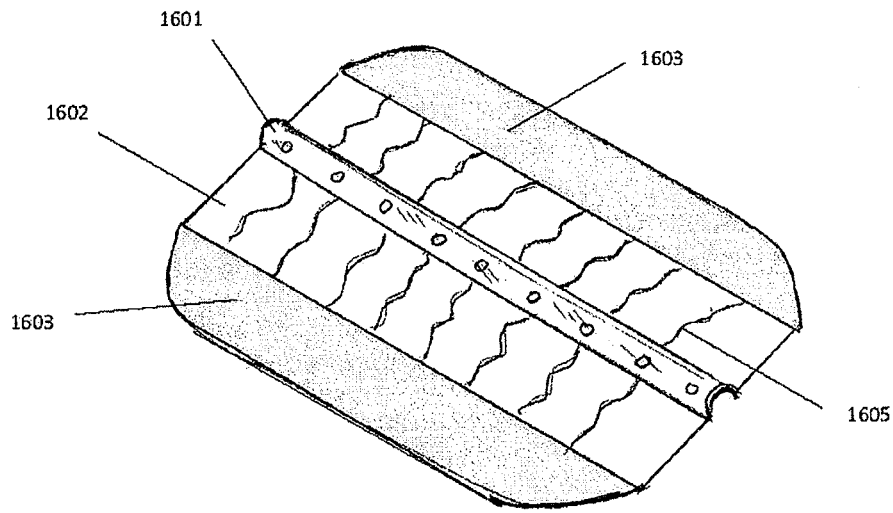
FIGS. 16A and 16B are perspective views of another example of a negative pressure therapy system in a contracted and stretched configuration, respectively.
Figure 16B:
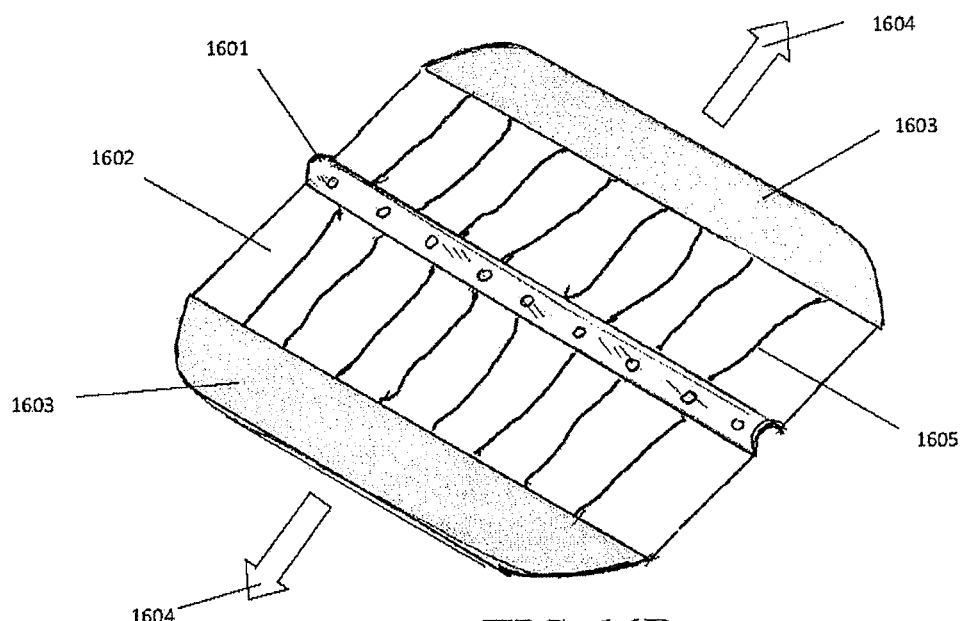

FIGS. 16A and 16B depict one example of a device that is configured to mitigate tension across a closed incision by applying counteractive compressive stress. The device 1600 comprises a collection chamber 1601 and a sealant layer 1602. The device further comprises pull tabs 1603 positioned at transverse peripheral edges of the device. The user may grab or otherwise use the pull tabs 1603 to apply pulling force (represented by arrow 1604) to stretch the device prior to application. The sealant layer 1602 may further comprise one or more stretch-limiting elements 1605 oriented, for example, along one axis of the sealant layer 1602, or in a substantially transverse direction to the incision. The size, shape and structure of the stretch-limiting elements may vary to suit the needs of the user. In an exemplary embodiment, each of the stretch-limiting elements 1605 may comprise one or more elongated elements that can be stretched to a maximum length along the long axis of the elongated element. The elongated element in one example is a fibrous element. In FIG. 16A, the device 1600 is depicted in a non-stretched state prior to application and stretch-limiting elements 1605 are slack. In FIG. 16B, the user has exerted pulling motion 1604 on pull tabs 1603 causing stretch-limiting elements 1605 to become taut and stretched to their maximum lengths. The stretch limiting elements thus can transition between a first state of a first size and/or shape, and a second state of a second size and/or shape, as well as various states there between. In this state, the elongate stretch-limiting elements 1605 substantially resist stretching the device past a distance limit corresponding to the length of the taut elongate stretch-limiting elements 1605.

Figure 17A:
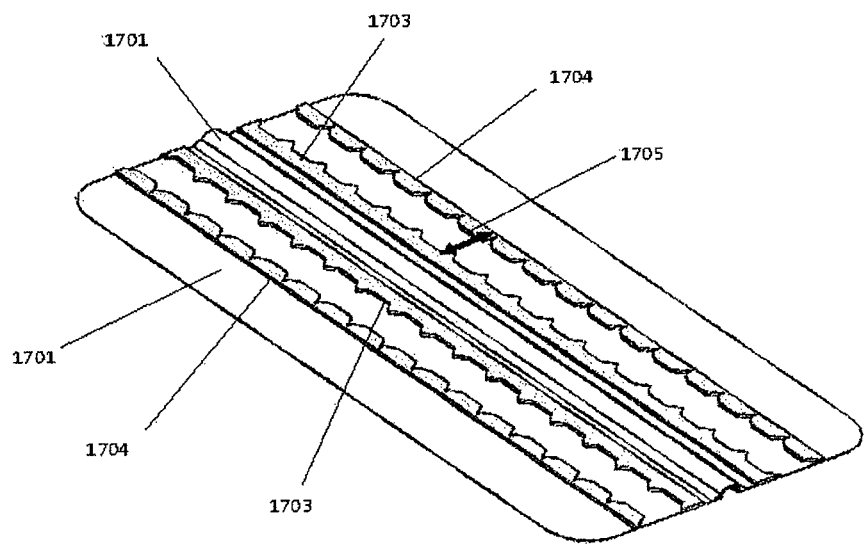
FIGS. 17A and 17B are perspective views of another example of a negative pressure therapy system in a stretched and a contracted configuration, respectively.
Figure 17B:
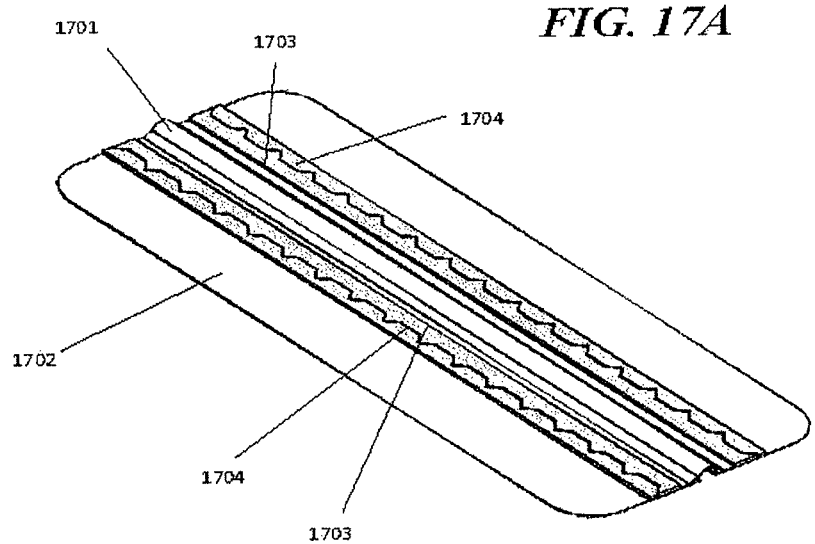

FIGS. 17A and 17B illustrate another device 1700 that is configured to mitigate tension across the closed incision by applying counteractive compressive stress. The device 1700 comprises a collection chamber 1701 and a sealant layer 1702. FIG. 17A depicts a state wherein the sealant layer 1702 is stretched, for example, by the user prior to application or is otherwise maintained in a stretched prior to application. The device comprises two or more sets of a proximal limiting element 1703 and a distal limiting element 1704, which are mounted longitudinally on the sealant layer 1702 on either side of the collection chamber 1701. The limiting elements 1703 and 1704 are elongated structures that are positioned in a spaced relationship. The proximal limiting element 1703 may have a shape that mates with a complementary shape of the distal limiting element 1704 such that the limiting elements may mate with one another when they meet. The proximal limiting element 1703 and the distal limiting element 1704 are configured with a distance 1705 between them in the stretched state. The distance between the limiting elements defines the maximum amount of allowed displacement between the limiting elements, which may correspond to displacement of the of the sealant structure and/or compression applied to the attached skin. Once the device has been applied to the patient, the residual tension in the device from the stretching will cause the device to contract toward a neutral state, such as the state depicted in FIG. 17B. The device may contract to a state wherein the distance 1705 has been reduced to substantially about zero and the limiting elements 1703 and 1704 are in direct physical contact with one another or otherwise restricting further contraction of the sealant layer 1702. However, the device does not necessarily contract to a state wherein the distance 1705 has been reduced to zero. In the state depicted by FIG. 17B, the device 1700 may or may not be configured to have residual tension remaining in sealant layer 1702. In some examples, which in the absence of the limiting elements 1703 and 1704, further contraction may occur, but the interaction of the proximal limiting element 1703 and the distal limiting element 1704 may be configured to resist or prevent further contraction of sealant layer 1702, thereby limiting the compressive stress that the device applies on the closed incision.

Figure 18A:
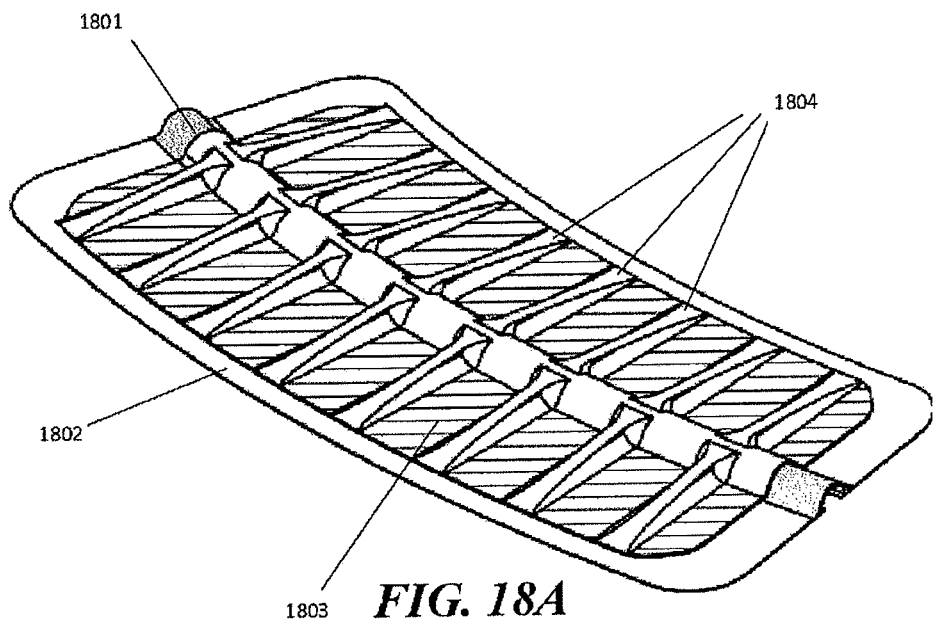
FIG. 18A is a perspective view of another example of a negative pressure therapy system.
Figure 18B:
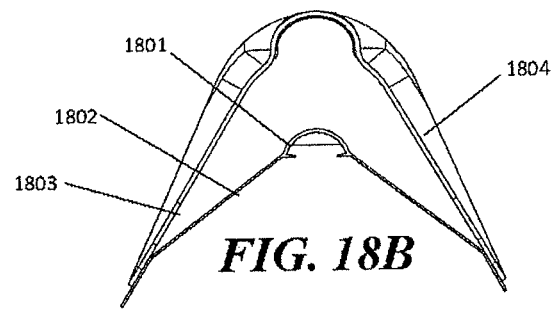
FIGS. 18B and 18C are end elevational views of the negative pressure therapy system in FIG. 18A in bent and straightened configurations, respectively.
Figure 18C:
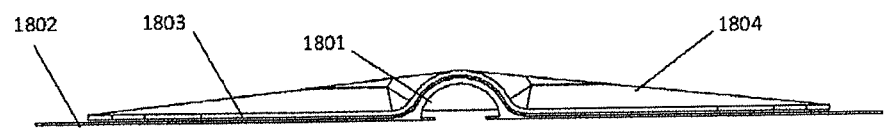

FIG. 18A depicts another example of a device 1800, comprising a collection chamber 1801 and sealant layer 1802, and further comprising a carrier structure 1803 that can also serve as a delivery tool. The sealant layer 1802 may be maintained in a stretched state with residual tension by presence of the carrier structure 1803. The carrier structure 1803 may comprise a series of transverse elements or ribs 1804 which provide the carrier structure 1803 with transverse rigidity, which may allow the carrier structure 1803 to maintain the sealant layer 1802 in a stretched state. The transverse ribs 1804 are separated by spaces between successive transverse ribs 1804. The spaces permit the transverse ribs 1804 to move relative to one another, which allows the carrier structure 1803 to be flexible longitudinally and to conform to a curvilinear incision, as depicted in FIG. 18A, which shows the device in a state of longitudinal flexure. Once the device is applied or adhered to the patient, the carrier structure 1803 may be removed, which allows residual tension in sealant layer 1802 to act upon and apply compressive stress to the closed incision. The device may also be configured as depicted in FIG. 18B to be positioned in a relaxed state in which the sealant layer 1802 remains unstretched or minimally stretched while connected to the carrier structure 1803. With deformation of the carrier structure 1803 as shown in FIG. 18C, the sealant layer 1802 then attains a substantially stretched state prior to application of the closed incision site.

Figure 19:
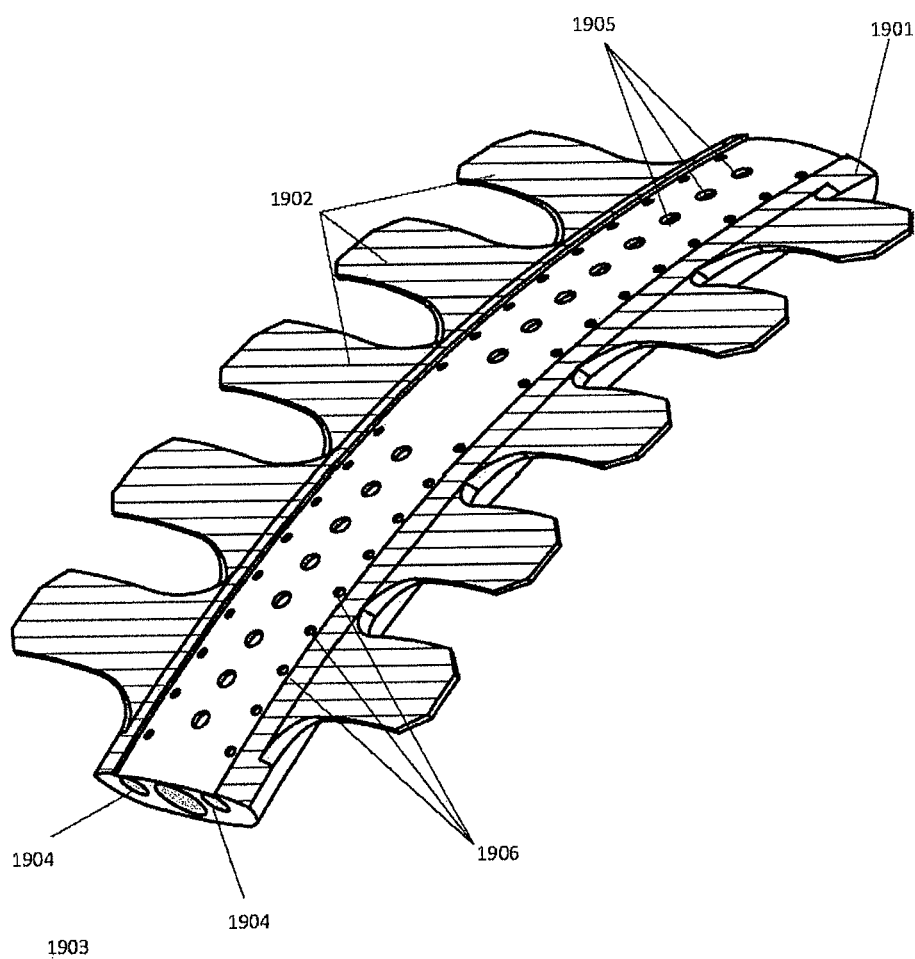
FIG. 19 is an inferior perspective view of another example of a negative pressure therapy system.

FIG. 19 is a perspective inferior view of an embodiment wherein the device 1900 is configured to serve as a vehicle for delivery of agents. The device comprises a sealing surface 1901 which in turn comprises adhesive tabs 1902 that extend outwardly from the sealing surface 1901 with spaces between the tabs 1902 for increased flexibility. The device 1900 also comprises a collection chamber 1903 as well as delivery chambers 1904. The collection chamber 1903 comprises a plurality of collection passageways 1905 and delivery chambers 1904, which comprise a plurality of delivery passageways 1906. The collection chamber 1903 may be connected to a reduced pressure source to apply reduced pressure to the closed incision. The delivery chambers 1904 are connected to a source of agents to be delivered and are not in direct fluid communication with collection chamber 1905. In use, agents to be delivered may be directed into delivery chambers 1904 and through delivery passageways 1906 to the closed incision area. Reduced pressure may be applied through the collection chamber 1903 and communicated to the closed incision area through collection passageways 1905. In some examples, agents to be delivered are introduced into the closed incision without being immediately removed by the reduced pressure source. This may be due to the distance between delivery passageways and collection passageways.

There is now described a pre-stretching element that may be applied to the device before application of the device to the skin. The pre-stretching element enables pre-stretching of the device and maintains the device in a pre-stretched state prior to application of the device to the skin. The pre-stretching element may be removed from the device after application to the skin. Upon removal of the pre-stretching element, residual tension in the sealant layer is released. The residual tension in the sealant layer is transferred to the skin, and may cause the sealant layer to tend to contract along the direction of the residual tension. This may impart transverse compressive stresses on the closed incision, which may oppose the tendency of the opposing edges of the closed incision to pull apart.

Figure 20C:
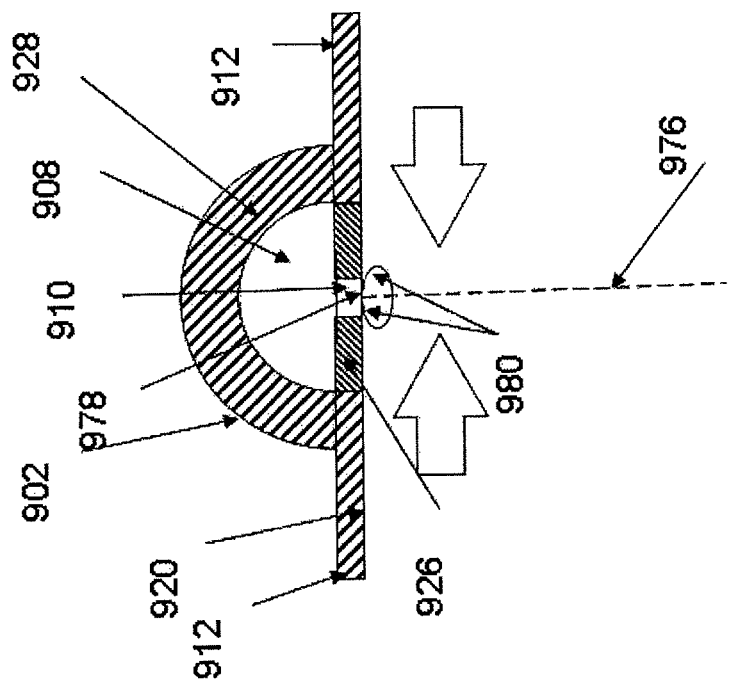

Referring to FIGS. 20A to 20G, in use, a central pre-stretching element 990 may be used to increase the space between the flaps 912 of the elastic support 902 of a reduced pressure therapy system (such as for the embodiment of the elastic support 902 shown in FIG. 9). The pre-stretching element 990 can also be used as a delivery tool. The presence of the pre-stretching element 990 permits the elastic support 902 to be applied in a stretched state to an incision or wound such that each flap 912 is adhered to the skin surface 920 of a respective edge of the incision or wound. In FIG. 20A, the elastic support is shown in a pre-stretched state where the pre-stretching element 990 is in an expanded state and maintains the elastomeric members 926 in a stretched configuration. The conduit walls 928 are also depicted in a stretched configuration in FIG. 20A.

Figure 20D:
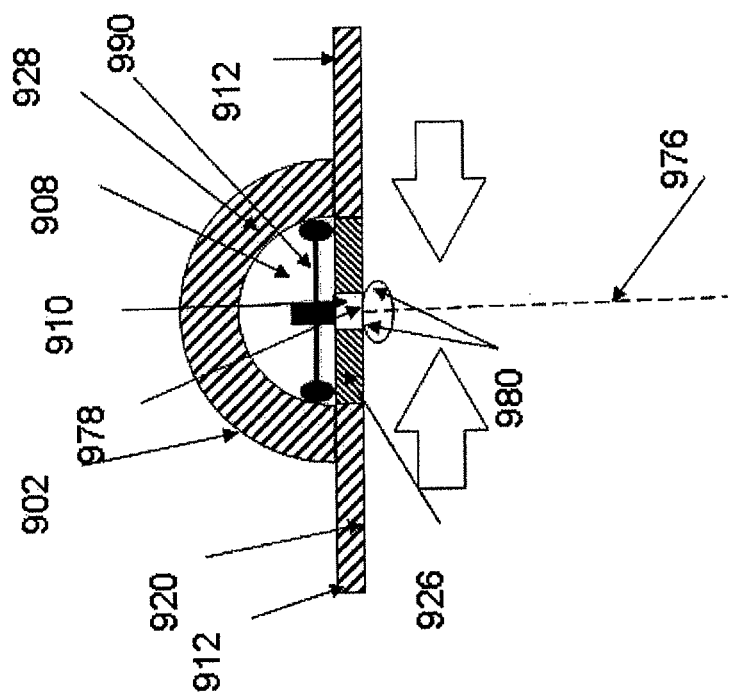
Figure 20E:
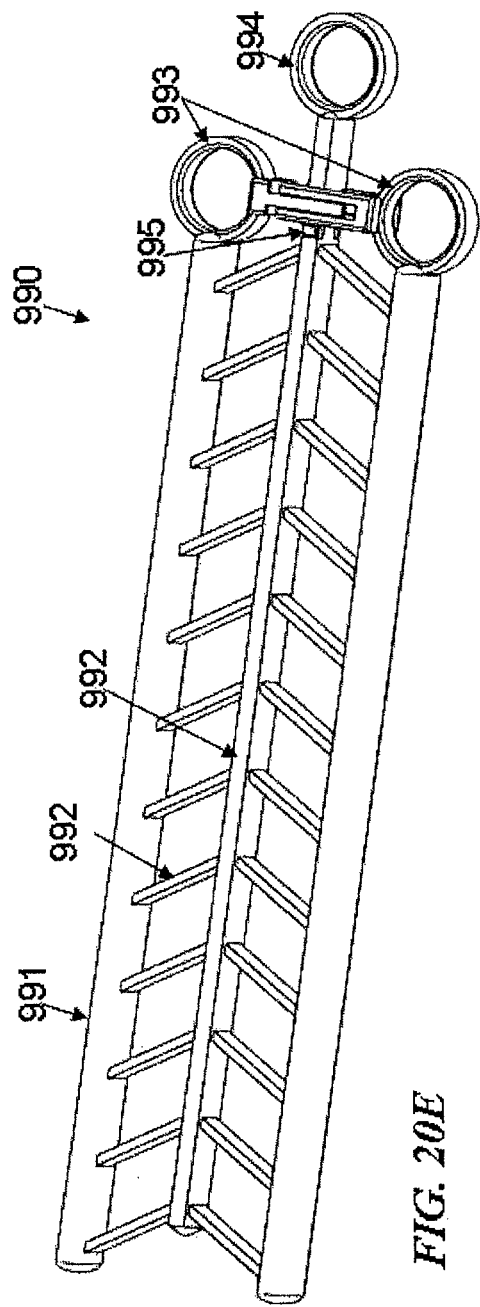
FIGS. 20E and 20G are perspective views of the negative pressure therapy system of FIGS. 20A to 20D in an expanded and retracted configuration, respectively.
Figure 20G:
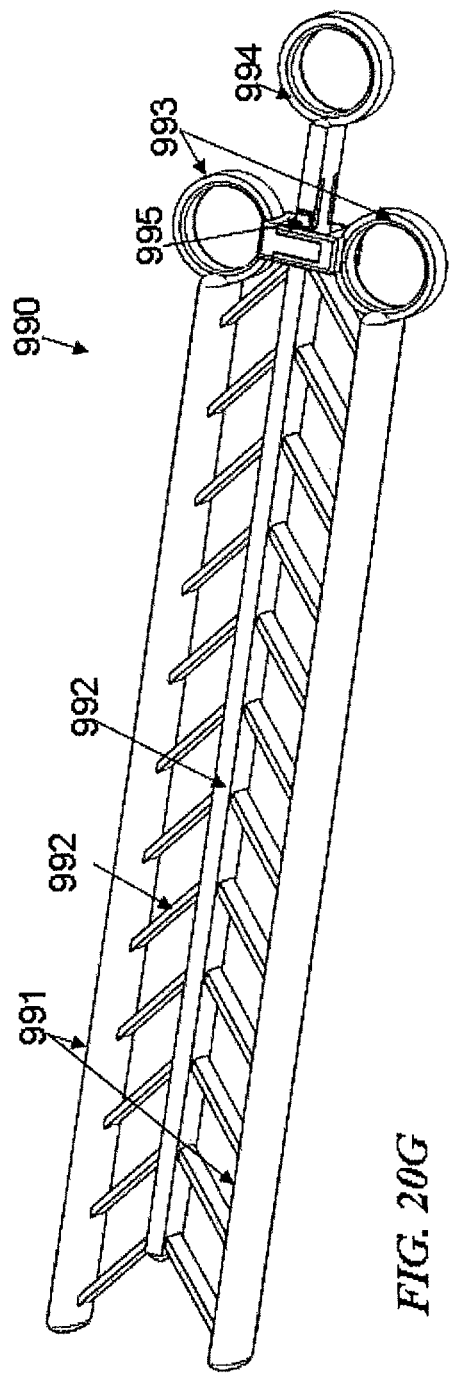
Figure 20F:
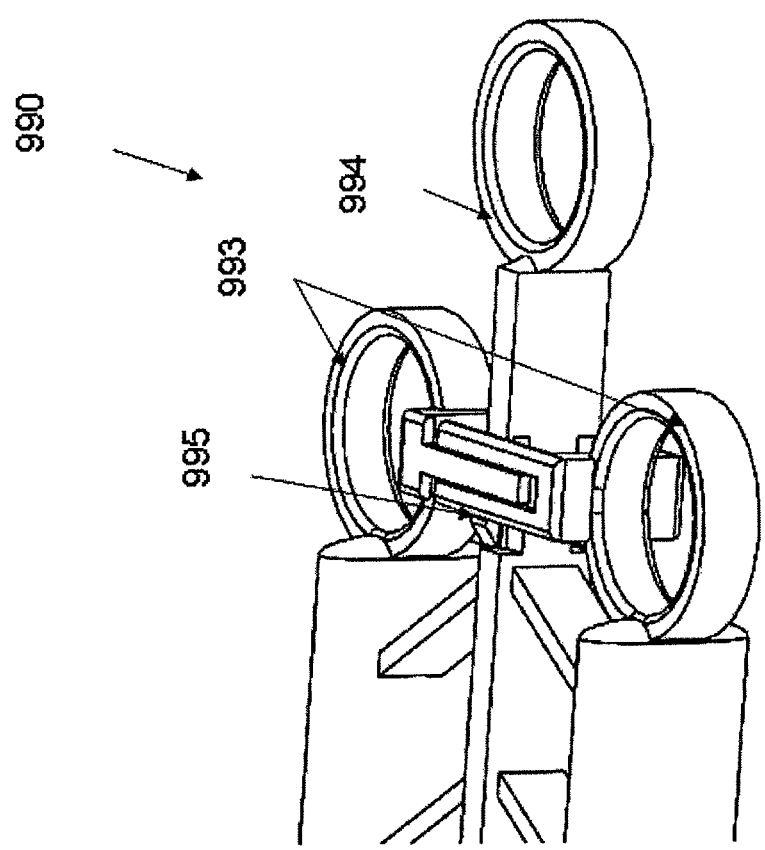
FIG. 20F is a detailed perspective view of the proximal end of the negative pressure therapy system in FIGS. 20E and 20G.

FIGS. 20E-20F show an enlarged view of an exemplary embodiment of the pre-stretching element 990 in an expanded state. The pre-stretching element 990 in an unexpanded state is shown in FIG. 20G. The pre-stretching element includes a set of expansion rails 991 connected to a central bar 992 via hinging struts 992. In an embodiment, the expansion rails 991 extend along a long axis of the pre-stretching element 992 with the hinging struts positioned transversely relative to the expansion rails 991 and in a hinged relationship with the expansion rails 991. The central bar 992 is coupled to a set of finger holes 993, 994. A user can achieve relative motion of the expansion rails and the central bar to transition the pre-stretching element 990 between the unexpanded and expanded states. Relative motion of the rails 991 to the central bar 992 occurs with motion of the finger holes 993 and 994 relative to one another. A latch tab 995 may be used to secure or lock the finger holes 993, 994 in a proximal position that causes the hinging struts 992 to separate the distance between the rails 991 as seen in FIGS. 20E and 20F. The latch tab 995 may also be released to allow the pre-stretching element to return to the unexpanded state shown in FIG. 20G.

With reference again to FIG. 20B, the pre-stretched elastic support 902 of the therapy system can then be applied to the skin surface 920 surrounding the closed incision site. The elastic support 902 may be applied to an incision 976 closed with sutures 978 or other type of incision closure, such as staples or glue. The sutures 978 may any type of suture and may be used with any of a variety of suture techniques, including running sutures and interrupted sutures. In some variations, although the sutures 978 may generally maintain the approximation of the closed incision edges 980, separation forces acting along the wound closure may generate focal regions of tissue tension. Application of the elastic support 902 to the incision may be used to apply additional contiguous force along a substantial length of the incision 976, which can reduce the focal tissue tension and possibly improve incision healing. In FIG. 20C, the pre-stretching element 990 has been changed to the unexpanded state to allow the device to impart forces to the skin tissue 920. The pre-stretching element 990 can then also be removed as shown in FIG. 20D, once the dressing has been applied to now allow connection to a reduced pressure source. The negative pressure therapy system 900 may be configured in a pre-stretched state with the pre-stretching element 990 in an expanded or unexpanded configuration or without the pre-stretching element initially inserted in the conduit 908.

Figure 21C:
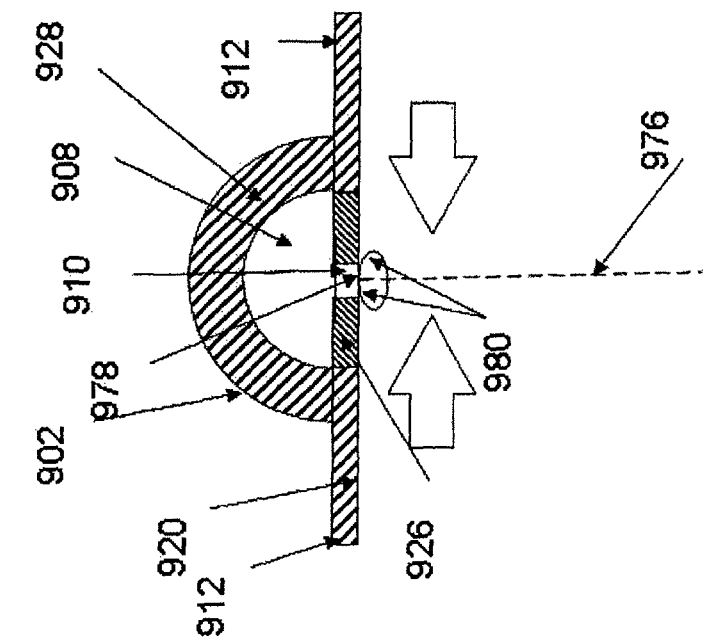

Referring to FIGS. 21A to 21D, in use, the flaps 912 of the elastic support 902 of FIG. 9 may be elastically stretched or pulled away from each other and applied in its stretched state to the incision or wound such that each flap 912 is adhered to the skin surface 920 to a respective edge of the incision or wound. Stretching of the flaps 912 and their elastomeric members 926 may be limited in extent by an inelastic member 996, as seen in FIG. 21B. The inelastic member 996 has a first end attached to one of the flaps 912 and a second end attached to another of the flaps 912 on an opposite side of the wound. The inelastic member 996 is positioned over the elastic support 902. That is, the inelastic member 996 is at least partially positioned on top of, but not necessarily in contact with, the elastic support 902 with respect to the orientation shown in FIGS. 21A-21D.

Figure 21D:
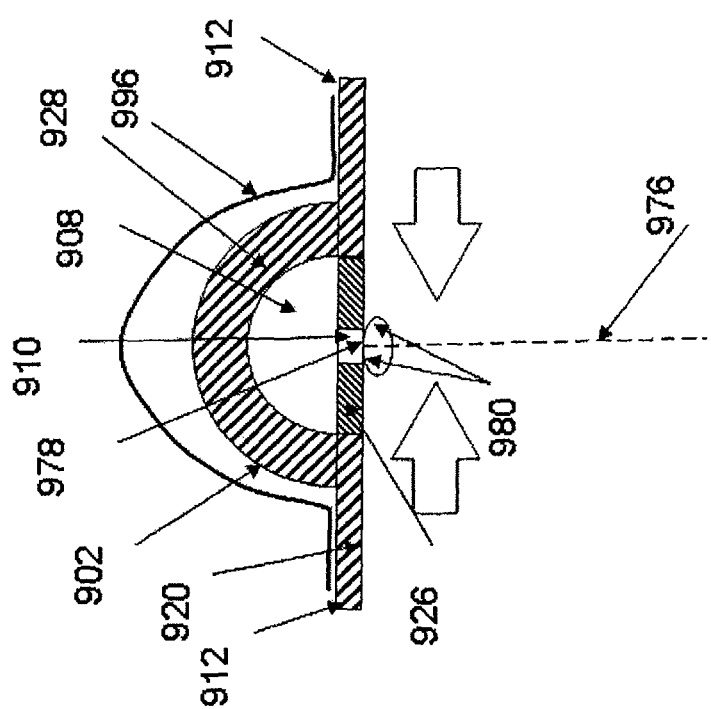

Once adhered to the skin surface 920, the stretching or deformation force may be relieved, and the elasticity or bias in the support 902 and elastomeric members 926 may push the closed incision edges 980 toward each other. The elastic support 902 may be applied to an incision 976 closed with sutures 978 or other type of incision closure such as staples. The sutures 978 may be any type of suture and may be used with any of a variety of suture techniques, including running sutures and interrupted sutures. In some variations, although the sutures 978 may generally maintain the approximation of the closed incision edges 980, separation forces acting along the wound closure may generate focal regions of tissue tension. Application of the elastic support 902 to the incision may be used to apply additional contiguous force along a substantial length of the incision 976, which can reduce the focal tissue tension and possibly improve incision healing. Once applied to the skin surface 920 as shown in FIG. 21C, the inelastic member may then be removed as shown in FIG. 21D if desired.

As described above, healing when the edges of a wound or incision are aligned and in close approximation is faster, cleaner and the scarring that results may be lessened. The proliferative stages of healing are characterized by angiogenesis, collagen deposition, granulation tissue formation, re-epithelialization and wound contraction. Epithelial cells migrate from the wound edges across the wound bed and proliferate providing cover for the new tissue being generated. The time-frame during which re-epithelialization occurs varies. Generally, cell growth and migration toward the wound center can occur between day 2 and 5 after a wound or an incision has been surgically closed. As such, the alignment and re-approximation of the wound edges is a key part in promoting wound healing and minimizing scarring. Normal body motion as well as underlying mechanical load and a state of tension exists naturally in the skin can result in tension perpendicular or transverse to the wound edges can cause the wound to separate during the healing process. Separation of wound edges can result in impaired wound healing as well as widened or hypertrophic scars. The risk of abnormal scarring is increased in the areas of the body where tension across the skin is greater, for example the anterior chest, abdomen, shoulders, upper back and extremities.

The devices described herein are configured to impart a force to relieve tension across incisions, and particularly closed incisions and reduce the likelihood that the wound edges will move apart. Further, the devices described herein can provide tension relief independent of applying negative pressure to the wound region. FIGS. 22A-22B show cross-sectional views of incision edges being pushed together such as by the devices described herein. FIG. 22A is the wound prior to approximation in which the wound edges are pulled apart and/or under tensile loading. FIG. 22B illustrates the drawing together of the wound such that the wound edges are approximated and aligned such that cell growth can occur and tension across the wound interface is lessened. The devices described herein also may provide a slight eversion of the wound edges. As such, the ridge of the healed incision may be more flush with the surrounding skin surface once the wound heals. The devices described herein can provide both active tension relief by creating compressive forces to counteract tensile forces across an incision as well as passive tension relief by resisting further tension from being imparted across an incision.

The relief of tension across the wound edges can prevent the wound from separating during the healing process, separation that leads to increased scarring and inhibition of wound healing. Further and as described above, the negative pressure applied by the device described herein can remove small pockets of fluid collections that can form within the cutaneous and/or subcutaneous tissues. Fluid collection in these areas can inhibit blood flow, immune function and penetration of antibiotics and therein contribute to bacterial growth and infections. Removal of exudate from the wound area provides for a cleaner wound environment.

Figure 23:
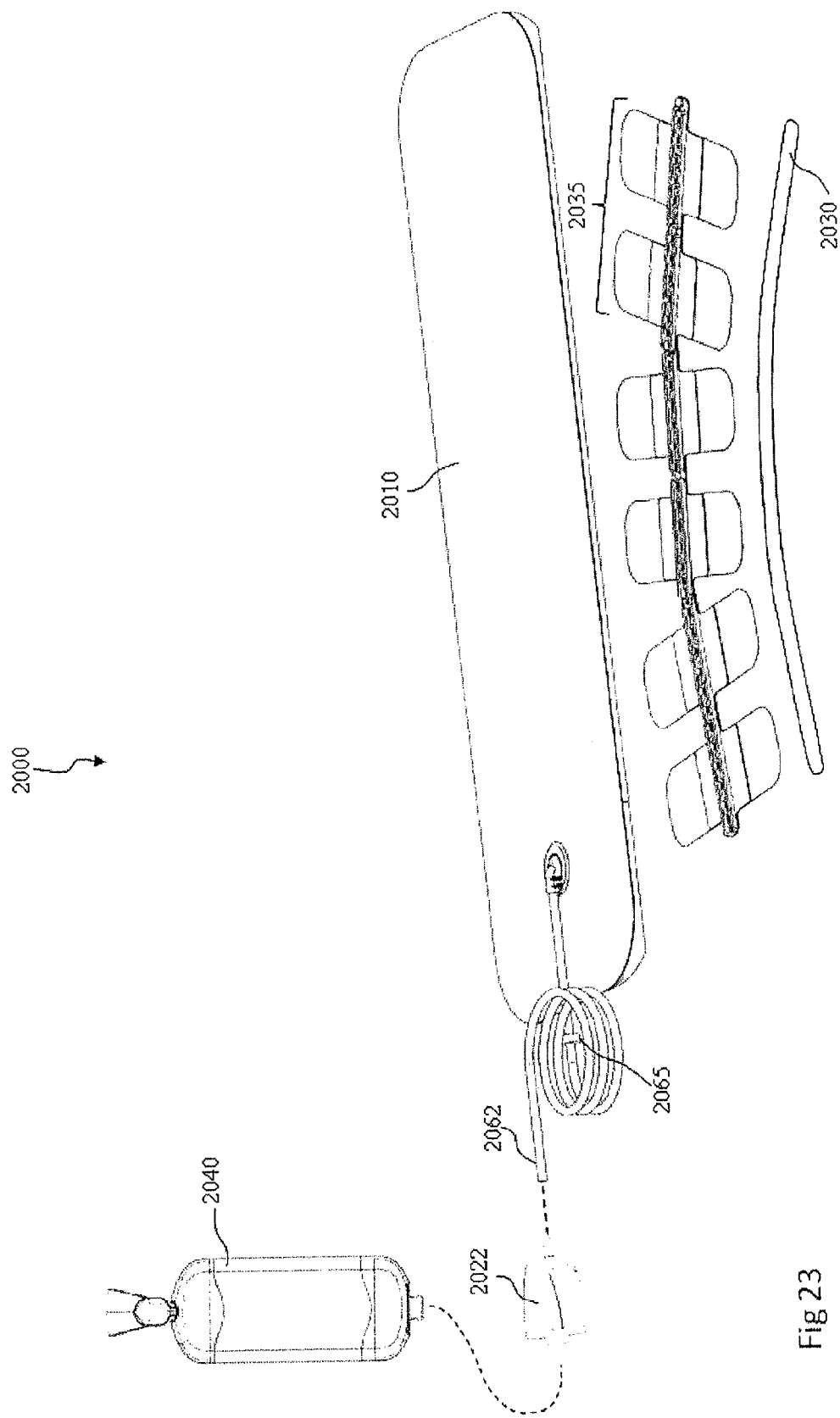
FIG. 23 is an exploded, perspective view of another embodiment of a negative pressure therapy device.

FIG. 23 illustrates a further embodiment of a negative pressure therapy device 2000 that provides tension relief in a modular and convenient manner and independently of the negative pressure delivery. The negative pressure therapy device 2000 can include a contact layer 2030 underlying one or more tension relief conduit modules 2035, and a sealant layer 2010 sized to cover the modules 2035. The sealant layer 2010 can be coupled to a connector tube 2062, which couples to a negative pressure source such as suction apparatus 2040 via connector 2022. The negative pressure therapy device 2000 can be configured to create and maintain a constant level of reduced pressure inside the sealed enclosure covering the wound area and provides both mechanical tension reduction and reduced pressure effects on the incision or wound. In this embodiment, the elements of the device are not integrated, providing the device with highly modular and customizable convenience. The devices disclosed herein have a high degree of modularity and can be used over wounds already closed by sutures, staples, adhesives and the like. It should be appreciated that the devices can be used to impart tension relief to the wound or incision edges without suction or negative pressure being applied. It should also be appreciated that the devices can be used to impart tension relief to a closed incision or an incision that has not been previously closed. The devices can be used to accommodate incisions and wounds of variable sizes and shapes, such as curvilinear wounds as well as generally straight wounds. The devices can be adapted to bridge between a wound or incision site to a remote location on the body.

The contact layer 2030 can be placed in direct contact with the surgically closed area of skin trauma. The contact layer 2030 can be a foam, mesh, gauze, sponge, particulate matter, a stacked mesh matrix, or any other suitable porous biocompatible material, for example, known in the art. The contact layer 2030 can be moist or dry. The contact layer 2030 can have antimicrobial properties or be impregnated with antimicrobial compounds and agents including by not limited to silver nanoparticles, polyhexamethylene biguanide (PHMB), and other antimicrobial agents.

Figure 24:
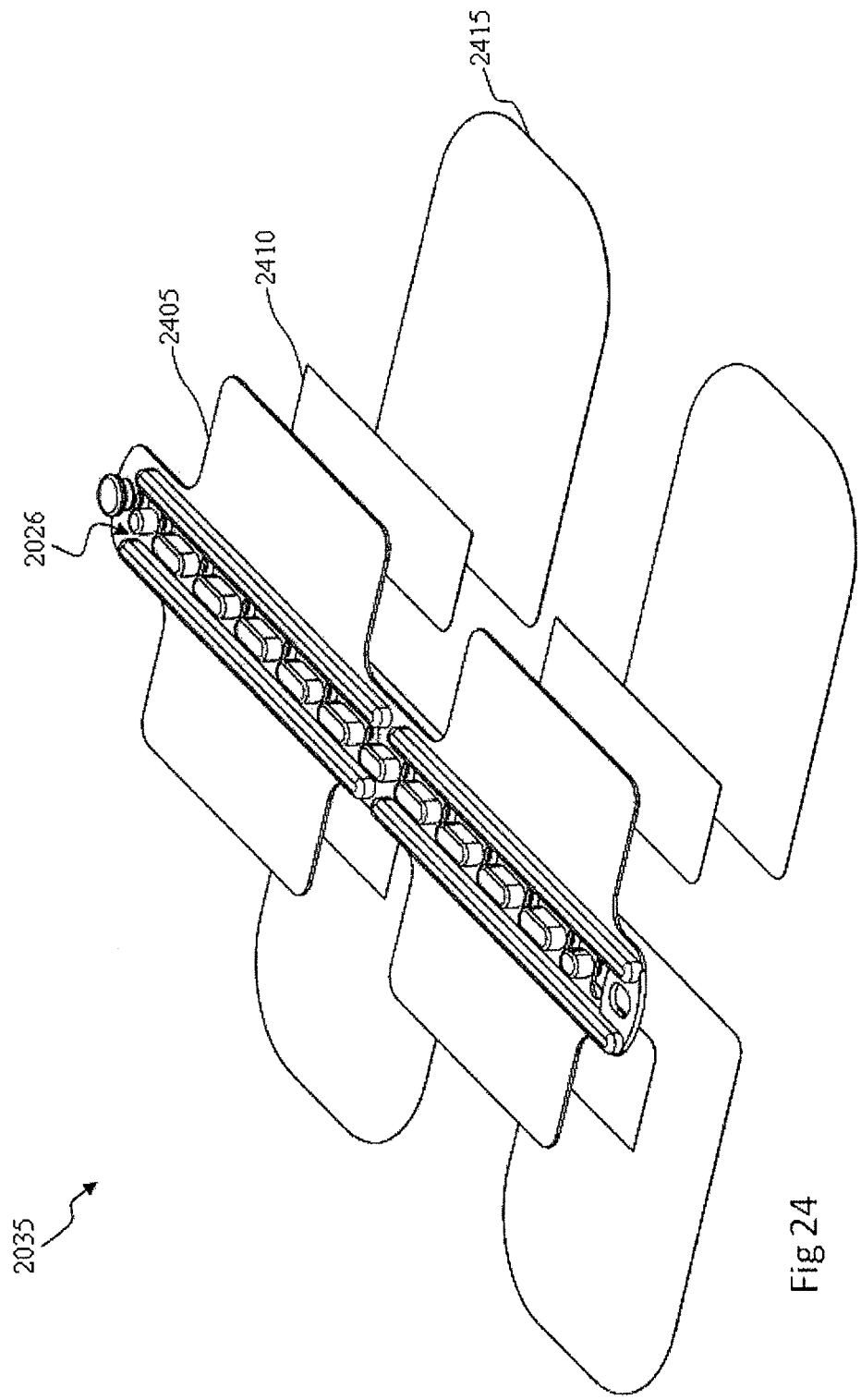
FIG. 24 is an exploded view of a tension relief conduit module.

As best shown in FIG. 24, the tension relief module 2035 can include an upper conduit layer 2405 coupled by a transfer adhesive 2410 to a lower adherent layer 2415. It should be appreciated that the tension relief module 2035 need not be multi-layered. The conduit layer 2405 is generally manufactured of a highly elastic material that is highly recoverable, such as a silicone elastomer, polyurethane, polyisoprene, other elastomers or other mechanically suitable material. This allows the conduit layer 2405 applied over the top of the contact layer 2030 and aligned at least in part along the longitudinal axis of the closed wound or incision to conform to the contours of the area of skin trauma and to stretch, flex, bend and/or conform in response to body movement. The adherent layer 2415 can be manufactured of a material that is highly elastic, has memory and further includes an adhesive on an underneath side, such as polyurethane coated with an acrylic, rubber or silicone adhesive. The adherent layer 2415 can include opposing structures that extend outward from the upper conduit layer 2405 forming at least a pair of wings that can be applied to a portion of the skin a distance away from the wound or incision, such as a healthy skin surface. The device can be applied to follow along the incision line such that peri-wound skin exposure is generally limited. Each pair of wings can have a symmetrical or asymmetrical shape. The adherent layer 2415 allows for low shear to maintain tension relief over time. The materials selected for the conduit layer 2405 and adherent layer 2415 can also be biocompatible and permeable materials that prevent the trapping of fluid under the tension relief conduit module 2035. The transfer adhesive can be any suitable material that binds the conduit layer 2405 to the adherent layer 2415 such as a silicone construction tape or transfer adhesive that is preferentially elastically comparable to the other layers. The conduit layer 2405 and the adherent layer 2415 also can be clear to translucent such that the underlying tissue can be visualized including the wound and underlying skin surrounding the wound. The planar tension relief conduit modules 2035 can further be configured such that removal of the sealant layer 2010 does not disturb or detach the conduit modules from the skin surface such that they remain and continue to maintain tension relief across the incision line. Such properties can be accommodated by constructing the tension relief conduit modules 2035 from silicone or by coating the top surfaces with a non-adherent material such as polytetrafluoroethylene (PTFE) or silicone.

Figure 25A:
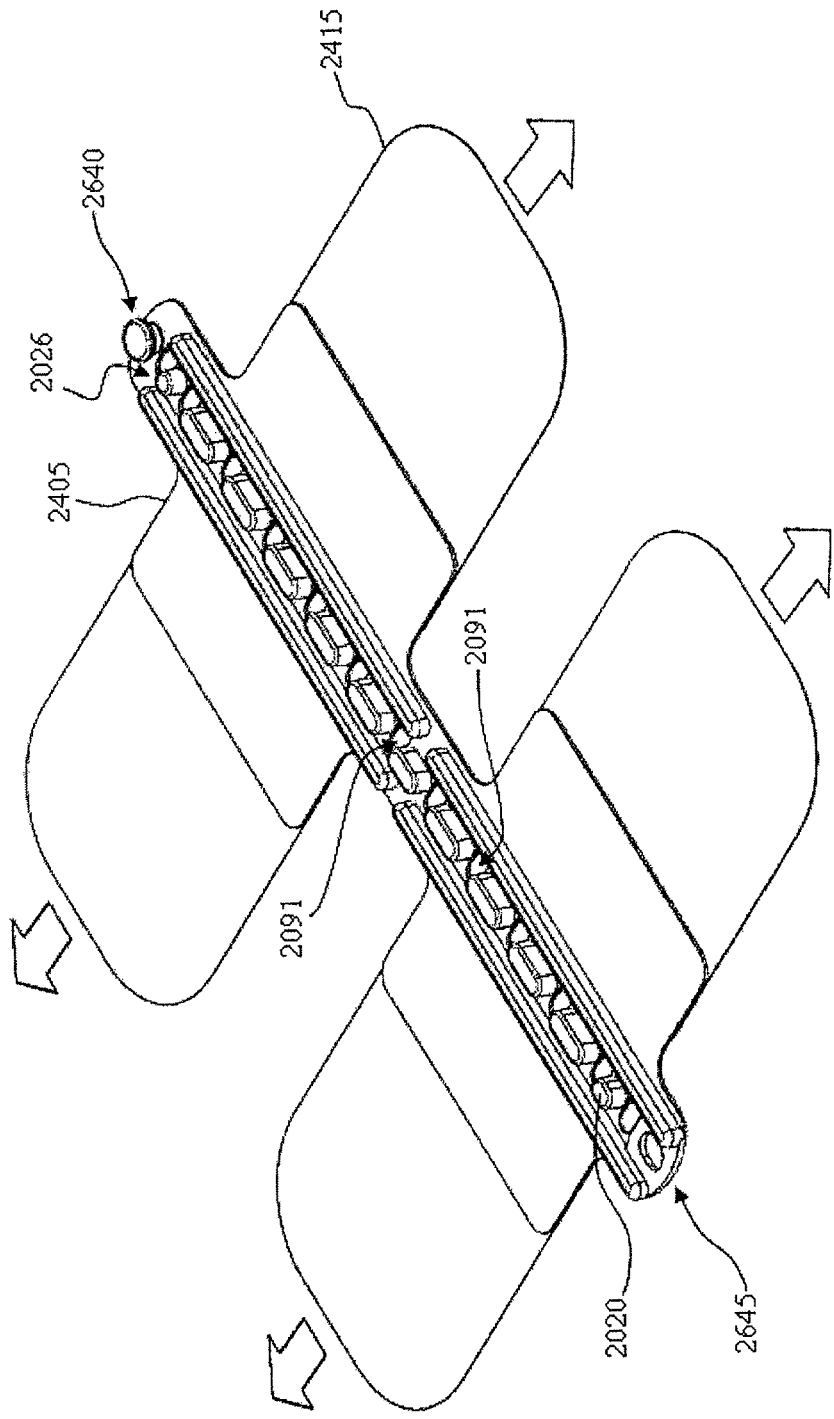
FIGS. 25A-25B are perspective views of the tension relief conduit module of FIG. 24.
Figure 25B:
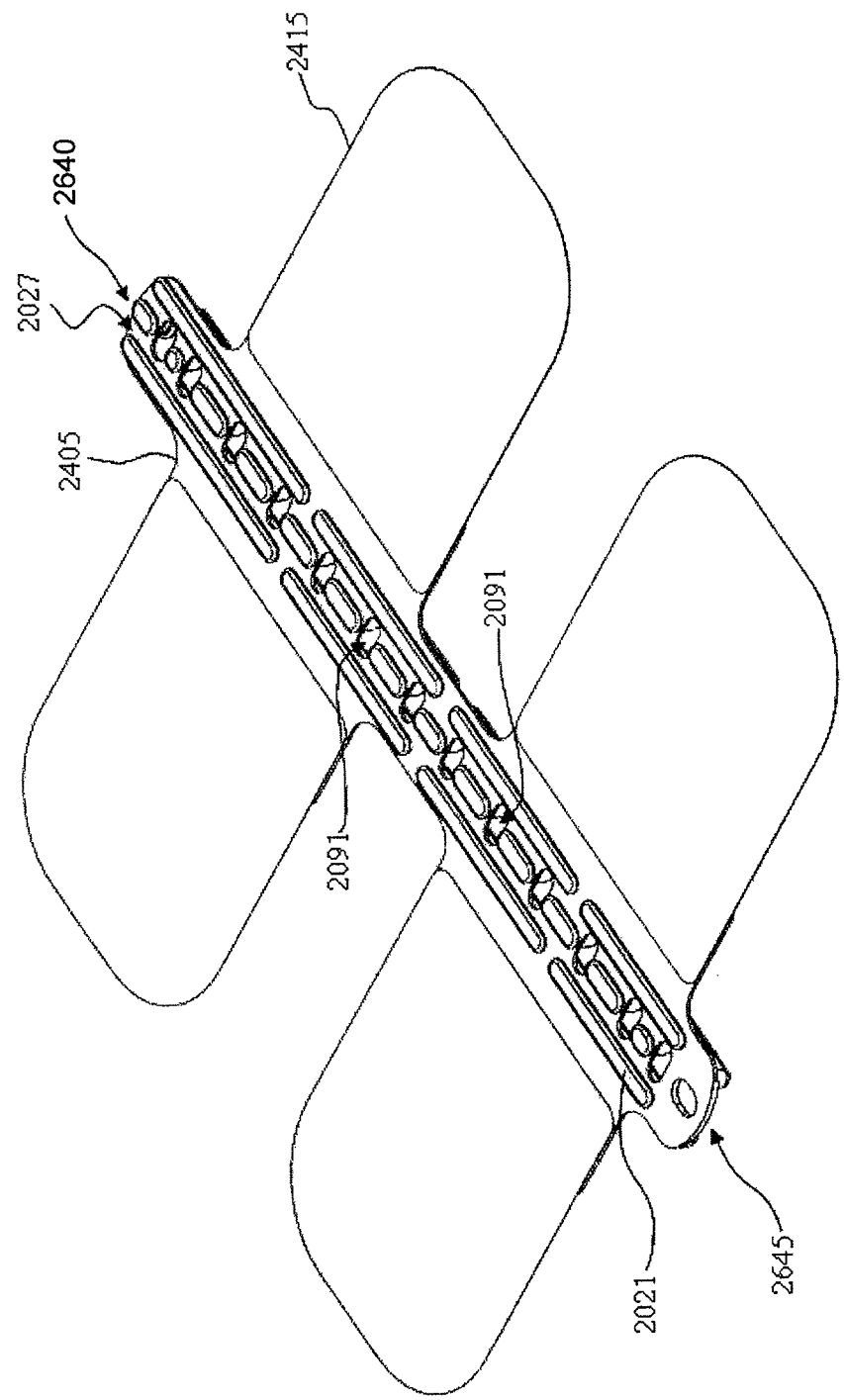

Still with respect to FIG. 24, the conduit layer 2405 can include a central conduit passage 2026. It should be appreciated that each tension relief module 2035 can be positioned on a patient such that the central conduit passage 2026 of the conduit layer 2405 is aligned with the longitudinal axis of the incision. As shown in FIG. 25A, an upper surface of the central conduit passage 2026 can include a plurality of support structures 2020, such as opposed side beams and a series of central posts. The support structures 2020 prop up and support the sealant layer 2010 upon positioning of the sealant layer 2010 over the one or more tension relief modules 2035. As shown in FIG. 25B, the underneath side of the tension relief conduit module 2035 can also include another bottom central conduit passage 2027 and a plurality of bottom support structures 2021 that allow collateral flow and egress of fluid from other areas below the conduit modules 2035. The support structures 2020 prevent the sealant layer 2010 from blocking the flow pathway or the transmission of reduced pressure along the created device passageway. The central conduit passage 2026 also can include one or more openings 2091 extending therethrough and interspersed between the central posts of the support structures 2020 (see for example, FIG. 25A-B). The openings 2091 can be arranged along a segment of or the entire conduit passage 2026. The spacing, size or shape of the openings 2091 can be uniform or non-uniform. The openings 2091 provide for fluid communication between the contact layer 2030 covering the wound and the upper surface of the central conduit passage 2026 such that exudate from the wound area can flow through the contact layer 2030 and onto the upper surface of the central conduit passage 2026. The support structures 2020 in combination with the sealant layer 2010 create an enclosed flow pathway or plurality of enclosed flow pathways of the central conduit passage 2026 through which aspirated exudate can flow and be evacuated with a suction apparatus 2040, as will be described in more detail below.

When vacuum therapy is no longer needed, the sealing layer can be removed and the openings 2091 can further provide a means to access and remove incision closure devices such as sutures or staples for example without disturbing the tension relief conduit module 2035. This can allow the module to continue to provide tension relief and mechanical support to the healing incision. Leaving the tension relief conduit modules in place after an incision has re-epithelialized can further shield the incision from potentially compromising mechanical forces that may cause the newly-healed wound to dehisce or separate.

Figure 26A:
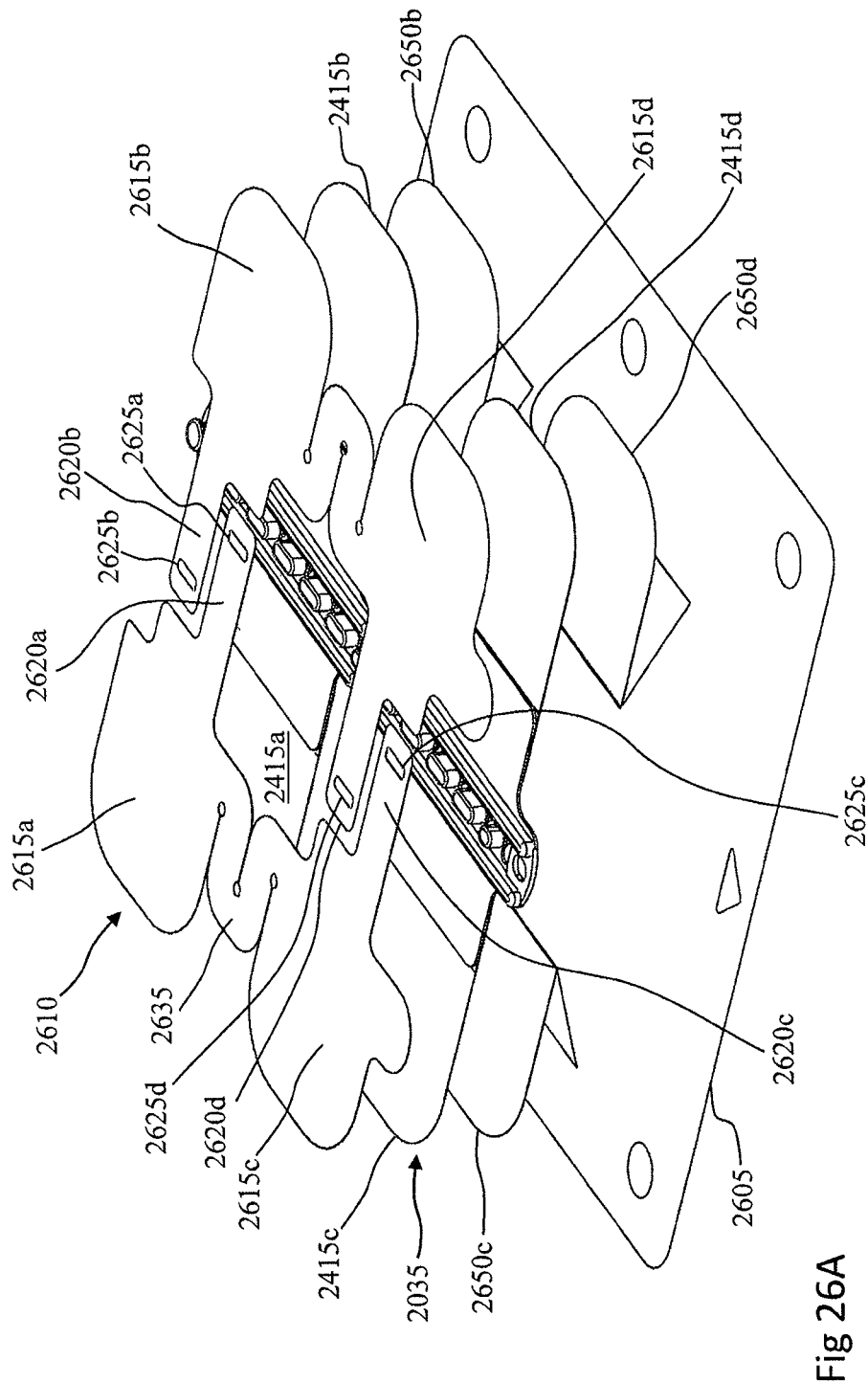
FIG. 26A is perspective exploded view and FIG. 26B is a top plane view of the tension relief conduit module of FIG. 24 positioned in a backing and having indicator.
Figure 26B:
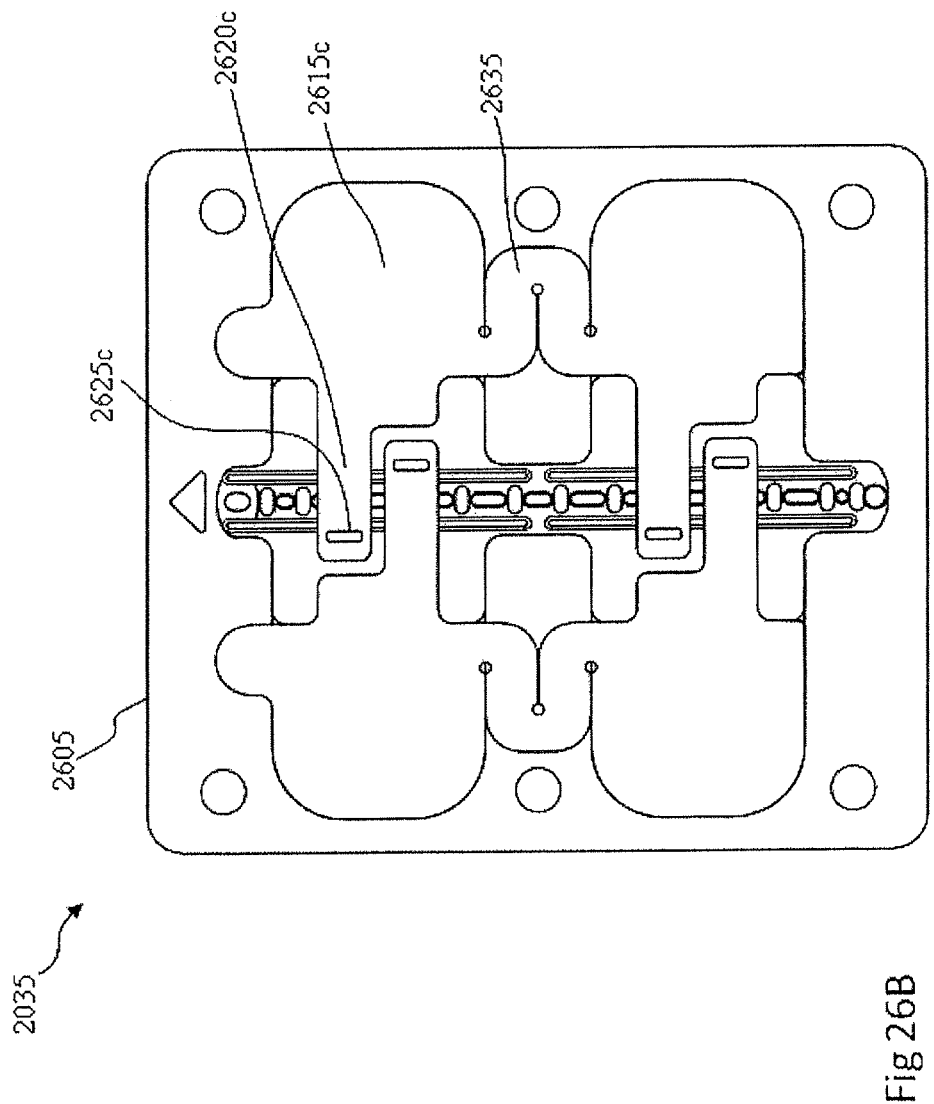

As shown in FIG. 26A-26B, the adherent layer 2415 of the tension relief conduit module 2035 can be positioned on a support backing 2605 prior to use. An indicator 2610 can also be adhered to a region of the upper side of the module 2035 for ease of handling during application of the generally floppy and highly flexible module. The indicator 2610 and backing 2605 are both removable. The backing 2605 can be removed to expose a central portion of the adherent layer 2415 prior to applying the module 2035 to the patient. The device can be stretched and the central portion of the adherent layer 2415 adhered to the patient. Folded release liners 2650 adhered to the underneath side of the adhesive layer 2415 can then be removed to expose the remaining portion of the wing(s) of the adherent layer 2415. The indicator 2610 is generally removed after applying the module 2035 to the patient and is adhered with an adhesive that releases from the upper side of the adhesive layer 2415 without removing the device from the skin.

The indicator 2610 can include two pairs of opposing pull tabs 2615 each coupled to a respective tensioning alignment tab 2620. A portion of each pull tab 2615 can be adhered to an upper surface of the adherent layer 2415 and another portion of each pull tab 2615, such as an outer region of the pull tab 2615, is not adhered. The tensioning alignment tabs 2620 can be freely movable with respect to the adherent layer 2415 and to one another. As such a user can grip the outer portion of the opposing pull tabs 2615 and apply tension to the underlying wings of the adherent layer 2415 (see arrows of FIG. 25A) such that the tensioning alignment tabs 2620 slide past one another. The wings of the adherent layer 2415 can be manually stretched from a relaxed configuration to a first tensile configuration in preparation for application to an incision. The wings of the adherent layer 2415 upon adhering to a patient skin surface can return towards the relaxed configuration from the first tensile configuration into a second tensile configuration after adherence to the skin surface and release by the user. The return toward the relaxed configuration of the adherent layer 2415 wings can impart a contracting force in a direction that is perpendicular or transverse to the longitudinal axis of the closed wound or incision or in a direction that is towards the center of the incision. It should be appreciated that the wings of the adherent layer 2415 once adhered to the skin surface generally do not completely return back to the relaxed configuration and instead will take on a second tensile configuration. The second tensile configuration can be under less stress than the first tensile configuration but higher stress than the relaxed configuration. As such that the adherent layer 2415 wings shield that closed wound or incision from endogenous or exogenous stress by imposing a strain on a surface of the skin surrounding the closed wound or incision. The adherent layer 2415 wings provide tensile support to the closed wound or incision such that mechanical tension on the edges of the closed wound or incision is alleviated. The adherent layer 2415 wings can also move the skin such that the wound edges are approximated and drawn toward the center of the wound or incision. In an embodiment, this surface of skin to which the adherent layer 2415 wings are adhered is healthy skin.

Each of the opposed tensioning alignment tabs 2620 can have alignment markers 2625 that provide the user with information as to the degree of stretching achieved in the wings of the adherent layer 2415. As the opposing pull tabs 2615 are pulled apart and the underlying adherent layer 2415 is stretched, the tensioning alignment tabs 2620 slide past one another until the opposing alignment markers 2625 approach and align with each other. Once desired tensioning of the module 2035 is achieved, the adherent layer 2415 wings can be pressed against the patient's skin. It should be appreciated that the adherent layer 2415 wings can be tensioned more than when the opposing alignment markers 2625 are aligned with each other. The alignment markers 2625 can be pulled past one another. Conversely, it should be appreciated that the adherent layer 2415 wings can be tensioned less than when the opposing alignment markers 2625 are aligned with each other. It should also be appreciated that other tensioning alignment mechanisms are considered herein. For example, stretch-limiting elements as described with reference to FIGS. 16A-16B or FIGS. 21A-21D can be included on the module 2035 that provide a mechanical interference and limit the degree of stretching of the adherent layer 2415 wings.

In an embodiment, the indicator 2610 includes two pairs of opposing pull tabs 2615a, 2615b, 2615c, 2615d coupled respectively to two pairs of opposing adherent layer wings 2415a, 2415b, 2415c, 2415d. Each pull tab 2615a, 2615b, 2615c, 2615d has a tensioning alignment tab 2620a, 2620b, 2620c, 2620d each having an alignment marker 2625a, 2625b, 2625c, 2625d. In this embodiment, once the backing 2605 is removed an outer region of the pull tabs 2615a, 2615b, 2615c, 2615d can be gripped by a user and the opposing adherent layer wings 2415a, 2415b, 2415c, 2415d stretched and pulled apart. As the adherent layer wings 2415a, 2415b, 2415c, 2415d are stretched the alignment markers 2625a, 2625b, 2625c, 2625d approach each other. When pull tabs 2615a, 2615b, 2615c, 2615d are pulled to a certain distance, the alignment markers 2625a, 2625b, 2625c, 2625d align with each other and optimal tensioning of the device has been achieved.

Each half of the module 2035 can be stretched and adhered to a patient's skin individually as can each module 2035 providing adjustable and customizable tension relief along the incision. The adjacent pull tabs 2615 can be connected by the indicator 2610, for example by a c-shaped portion 2635. The portion 2635 can have other shapes that provide some level of structural rigidity. This arrangement provides some structural rigidity to the otherwise highly flexible tension relief conduit module 2035. The indicator 2610 can maintain the half of the module 2035 not being actively adhered to the patient in a position that does not interfere with the positioning of the other half of the module 2035. These structures help facilitate ease of handling and application of module 2035 and when removed after application allow the flexible conduit module 2035 to conform to the skin surface more optimally.

Each of the opposing wings of the adherent layer 2415 can be adhered to opposite sides of the incision such that the adherent layer 2415 can adhere to the skin surrounding the incision or wound and the central conduit passage 2026 located between the opposing wings of the adherent layer 2415 aligns with the longitudinal axis of the incision. The opposing wings of the adherent layer 2415 can impart a contracting force perpendicular or transverse to the incision or in a direction that is towards the wound center (opposite of the direction of the arrows in FIG. 25). These opposing forces on each side of the wound can augment the edge approximation and drawn the incision or wound edges together. It should be appreciated that the orientation of the adherent layer 2415 wings can be customized such that the orientation of the tension relief forces applied are in other directions besides transverse to the longitudinal axis of the incision or wound.

Figure 27A:
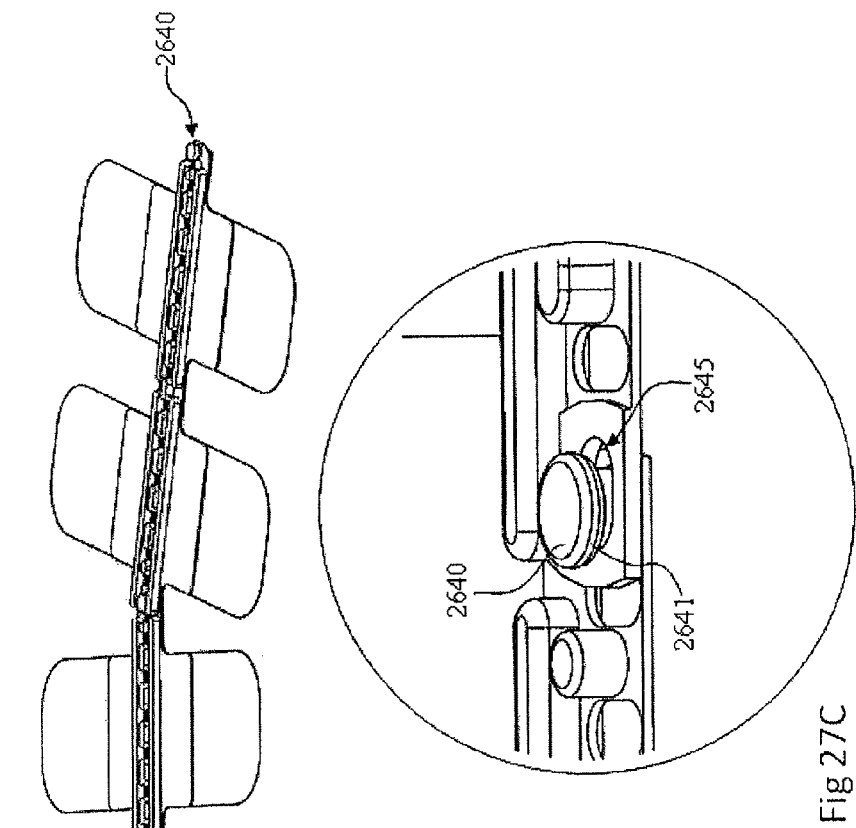
FIGS. 27A-27C are perspective views of a plurality of tension relief conduit modules coupled together.
Figure 27B:
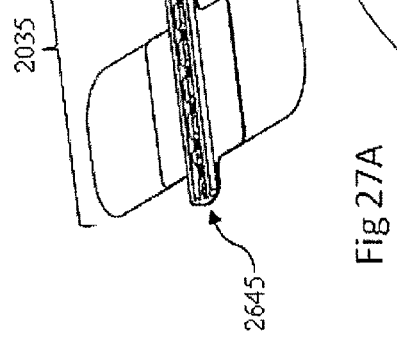
Figure 27C:
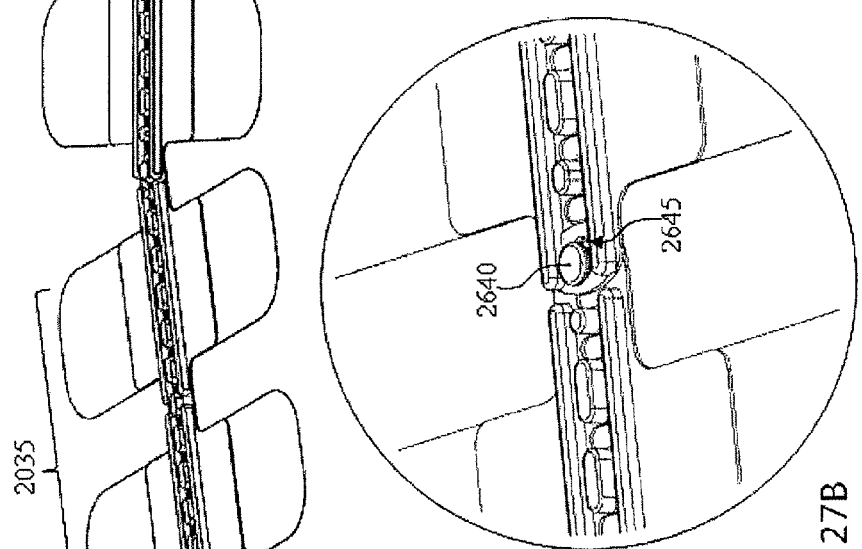

In some examples, the device 2000 can be used to treat incisions or elongate wounds that are longer than the length of a single tension relief conduit module 2035 or can be used to bridge from a wound or incision site to a site remote from the treatment site. The remote site can include a non-incision or non-wound location. The remote site can also include another incision or wound site. In these situations multiple tension relief conduit modules 2035 can be used in serial and/or parallel fashion. In an embodiment, the central conduit passage 2026 of each tension relief conduit module 2035 aligned in series can include a male mating end 2640 and a female mating end 2645 (see FIGS. 25 and 27). The mating ends 2640, 2645 can allow multiple tension relief conduit modules 2035 to be coupled together and applied along a length of the incision to provide a continuous conduit along the length of the wound. In FIGS. 27B and 27C, the mating ends are shown secured together with female mating end 2645 placed over the male mating end 2640. The female mating end 2645 may slip over the male mating end 2640 due to the elastically deformable behavior of the material which creates a button-like mechanical fixturing as shown more clearly in the cut-away image in FIG. 27C where the lip of the male mating end 2640 overlaps with the border of the female opening 2645. This modularity accommodates longer incisions or incisions having an irregular or jagged shape. The tension relief conduit module 2035 is shown in the figures as having two pairs of opposing wings of the adherent layer 2415. It should be appreciated that the adherent layer 2415 can have a single pair of opposed wings. Alternatively, the module 2035 can be cut down the center such that a single pair of opposed wings of the adherent layer 2415 can be used, for example to treat an incision shorter than the length of a single module 2035.

Once the backing 2605 is removed from module 2035, an adhesive region of the adherent layer 2415 wings is exposed allowing adhesion to the patient. The folded release liners 2650 are removed to secure the module to the patient then, the indicator 2610 can be removed from the upper surface of the module 2035. After the appropriate number of modules are connected and secured to the patient, the sealant layer 2010 may be applied. The sealant layer 2010 may be removed at some later time after negative pressure therapy is complete. Advantageously, one or more tension relief conduit modules 2035 can remain on the skin after removal of the sealant layer 2010 and continue to provide tension relief to the incision.

FIGS. 28A-28B illustrate an embodiment of the sealant layer 2010. The sealant layer 2010 can be placed above or over the one or more tension relief conduit modules 2035 forming a sealed enclosure with the wound such that suction can be applied to the wound area through a port 2705 and port opening 2706 in the sealant layer 2010. The sealant layer 2010 is sized such that it is large enough to entirely cover the one or more modules 2035 as well as a portion of the skin surrounding the one or modules 2035. It should be appreciated that the sealant layer 2010 can form a seal whether or not the sealant layer 2010 covers the entire tension relief module and a portion of the skin surrounding the incision and not covered by the tension relief module. The sealant layer 2010 can also form and maintain a good seal with the conduit module when a portion of the tension relief module is left uncovered by the sealant layer 2010. The sealant layer 2010 and/or conduit can be provided in the form of a roll or a folded form, which is then dispensed and cut as needed. The rolled form provides a more compact configuration for ease in packaging, handling and application of the device. Placement of the port opening 2706 over the support structure 2020 of the central conduit passage 2026 facilitates fluid egress and transmission of the negative pressure generated by the suction apparatus 2040 via the connector tube 2062. The sealant layer 2010 can contact and be propped up by the support structures 2020 of the central conduit passage 2026. It should be appreciated that where the sealant layer 2010 is propped up by and makes contact with the support structures 2020 adhesion or a seal need not occur. Rather, a seal between the sealant layer 2010 and the skin can prevent leaks in the system upon application of a negative pressure.

The sealant layer 2010 can be a polyurethane sheet having an adherent layer on its underneath side or any other suitable material that will provide a seal against the skin for reduced shear or creep. The adherent layer can be a hydrocolloid adhesive. The adherent layer can also be an acrylic, silicone, or rubber adhesive. The material of the sealant layer 2010 does not generally adhere to the material of the support structures 2020 so the patency of the central conduit passage 2026 is maintained despite negative pressures being applied by the suction apparatus 2040 as will be described. The sealant layer 2010 can be configured so as not to collapse and occlude the central conduit passage 2026. In an embodiment, the sealant layer 2010 is resistant to deforming and conforming to the central conduit passage 2026. In another embodiment, a screen mechanism or another enclosure or alternate sealing layer can be incorporated along the central conduit passage 2026 that prevents collapse of the sealant layer 2010 under negative pressure. The use of silicone or another nonadherent material can further aid in maintaining patency of the central conduit passage 2026. The hydrocolloid can also be manufactured to be thin and/or less malleable so as not to deform and fill the passage.

Because hydrocolloids can absorb moisture, the sealant layer 2010 keeps the underlying skin to which it is adhered drier than other occlusive dressings and limits maceration to maintain skin health. Both polyurethane and hydrocolloid are permeable materials that reduce the trapping of moisture and fluid under the device. The sealant layer 2010, like the tension relief conduit modules 2035, can be manufactured of a translucent material that enables viewing of the underlying tissue.

The sealant layer 2010 can include a release liner 2720 adhered to the adhesive underneath surface. The adhesive can also be adhered to a flexible and conformable backing 2730 that supports the adhesive and has mechanical properties that support stretching and contouring to the body surface. A release liner break line 2715 allows the release liner 2720 below the port 2705 to be removed and that portion of the sealant layer 2010 to be adhered first. The sealant layer 2010 below the port 2705 can be gradually unrolled or unfolded out onto the skin and adhered to the patient as the release liner 2720 is pulled away from the underneath side of the sealant layer 2010. The release liner 2720 above the port 2705 can be removed and that portion of the sealant layer 2010 above the port 2705 (and the release liner break line 2715) adhered last. Side release liners 2710 further allow simple initial application.

As mentioned, the sealant layer 2010 can be generally larger than the tension relief conduit modules 2035, but can be cut-to-size prior to or after removal of the release liners 2710, 2720. The sealing layer upper surface 2730 and/or release liners 2710, 2720 can have a grid or other pattern that provides convenience for cutting the layer 2010 to size. Alternatively, the sealant layer 2010 can be modular (see FIG. 29). For example, the sealant layer 2010 can be a plurality of smaller segments 2725 of sealant layers. The sealing layer segments 2725 can be stacked on each other in order to seal wounds of a variety of shapes and sizes. The port 2705 can be placed anywhere along the conduit and potentially in different orientations to accommodate the desired placement of the suction apparatus.

The port 2705 of the sealant layer 2010 can be coupled to a connector tube 2062. The connector tube 2062 and port 2705 can come pre-attached to the sealant layer 2010 or can be applied after the sealant layer 2010 is applied to the patient. Generally, the port 2705 is near an end of the sealant layer 2010, but can also be positioned near an inner region of the sealant layer 2010. Because the length of the connector tube 2062 can be customized, the position and orientation of the port 2705 can be variable. One end of the connector tube 2062 can be coupled to the port 2705 and the opposite end of the connector tube 2062 can be coupled via the connector 2022 to the suction apparatus 2040 (see FIG. 23). Upon connection with the connector 2022, the connector tube 2062 and connector 2022 are prevented from inadvertent uncoupling such as via a barb or other attachment mechanism.

The suction apparatus 2040 can then be connected to the connector 2022 which is in fluid communication with the central conduit passage 2026 via the connector tube 2062. With the sealant layer 2010 in place over the conduit passage 2026 and upon activation of negative pressure therapy, exudate can be evacuated such that it flows through the conduit passage 2026 and collects within a chamber of the suction apparatus 2040. The exudate can be evacuated continually until therapy is discontinued or until the fluid capacity of the suction apparatus 2040 is exhausted. The suction apparatus 2040 and collected exudate can be disposed and a new suction apparatus 2040 coupled to the connector 2022 as needed such as when the suction apparatus 2040 chamber capacity is reached but the therapy is not yet completed. A one-way flow valve 2065 (see FIG. 23) can be positioned within the port 2705, a region of the connector tube 2062 (as shown) or connector 2022. The one-way flow valve 2065 can allow air molecules or other materials to be removed while resisting entry of air molecules or other materials in a direction towards the central conduit passage 2026. The port 2705 can also include a negative pressure indicator that is visual and/or tactile. For example, the port 2705 can include collapsible bubble the user can view to determine whether negative pressure is being successfully delivered upon activation of the suction apparatus 2040. The port 2705 can also include a flexible convex component that when negative pressure is successfully delivered will invert to a concave shape that can be felt by a user.

The suction apparatus 2040 can be a syringe, a powered pump, a Venturi system, a forced expansion device, constant force spring, or a static negative pressure device, a powered suction pump, a durable medical equipment evacuator, or any suitable active or passive suction source. In an embodiment, the suction apparatus 2040 is a constant force spring such as described in U.S. Patent Application Publication No. 2010-0042021, which is incorporated by reference herein in its entirety.

Furthermore, the negative pressure therapy device 2000 may also be configured to treat multiple incisions with a single sealant layer. As before, a contact layer 2030 may be placed down over the incisions to be treated. Over the intact skin between the incisions, a protective layer or layers can be placed to limit the exposure of that skin to suction and moisture from exudates. Examples of protective layers include occlusive barriers such as acrylic adhesive polyurethane dressings or hydrocolloid dressings. The tension relief conduit modules 2035 may then be placed over the incisions to be treated as well as over the intact skin to create a bridge between the different incisions. The conduit modules 2035 need not be placed in a tension-reducing mode to effectively create a bridge between the treatment sites.

The negative pressure therapy device 2000 may further be used as a bridge to deliver negative pressure to a limited-access location such as the bottom sole of a patient's foot or other anatomical location that is difficult to service with the device from a remote site such as the side of the leg or other location where a manifold or pressure port is more manageable from a patient comfort stand-point. In an embodiment, the negative pressure therapy device 2000 can be used to deliver negative pressure from the proximal end of the device where the port 2705 is located to the distal end of the device where the wound or incision is located. The modularity of the device 2000 allows for variation and tailoring of the distance between the port 2705 and the wound or incision site. A region of intact skin between the proximal end of the dressing up to the distal end to which negative pressure is to be delivered may be covered with a protective layer to facilitate delivery of negative pressure primarily to the distal end of the device. The distal end may be connected to a treatment site for a chronic wound such as a diabetic ulcer or a wound located in a location where otherwise putting a port might lead to an undesirable pressure point such as on the heel of the foot. The bridging provides a low profile source of reduced pressure supplied to the limited-access tissue site thereby increasing patient comfort and enhancing the reliability of the negative pressure supply.

The thinness of the sealing layer 2010 dressing and tension relief conduit modules 2035 allow the device to be discrete and unobtrusive for patient comfort. The low profile of the device can allow it to remain substantially flush with the skin surface and be easily worn discretely under clothing without creating bulges or other irregular protrusions. The low profile and smooth contours can further prevent the device from being mechanically disrupted such as by catching on surfaces, which might compromise the seal and/or tension relief properties of the device. The device can have a maximum dimension of approximately 12 mm or less in thickness, 11 mm or less, 10 mm or less or 9 mm or less. At the port, the device can have a maximum dimension of approximately 9 mm or less than 10 mm thick. The tension relief conduit module portion of the device can have a thickness that is approximately less than 2.5 mm. Where the sealing layer dressing covers the tension relief conduit modules, the device can have a maximum thickness that is less than 12 mm. The majority of the device can be less than 3.0 mm in thickness. The sealing layer (hydrocolloid) dressing by itself can be between about 0.2 mm to about 1.0 mm thick, but it should be appreciated that the sealing layer dressing can be outside this range. In an embodiment, the sealing layer dressing is between about 0.25 mm to about 0.75 mm thick. In another embodiment, the sealing layer dressing is between about 0.5 mm to about 0.75 mm thick.

While a number of embodiments have been shown and described herein, one of skill in the art will understand that these embodiments are provided by way of example only. Numerous variations, changes, and substitutions may be made those skilled in the art without departing from the invention. It should be understood that various alternatives to the embodiments described herein may also be employed. It is intended that the following claims define the scope of the invention and that methods and structures within the scope of these claims and their equivalents be covered thereby. For all of the embodiments described herein, the steps of the methods need not be performed sequentially.

What is claimed is:

1. A device for treating an incision, the device comprising:
    a tension relief module, comprising:
        a conduit structure comprising an upper surface, a lower surface, and at least one opening extending from the lower surface to the upper surface, wherein the at least one opening is configured to provide fluid communication between the upper surface of the conduit structure and the incision;
        a first mating end positioned at a first end of the conduit structure;
        a second mating end positioned at a second end of the conduit structure, wherein the second end of the conduit structure is opposite the first end of the conduit structure, and wherein each of the first mating end and the second mating end is configured to mate with another conduit structure; and
        opposing adhesive structures coupled to the conduit structure.

2. The device of claim 1, further comprising a flexible sealant structure sized to cover the tension relief module, wherein the flexible sealant structure comprises a lower adhesive surface.

3. The device of claim 2, wherein the lower adhesive surface of the flexible sealant structure and the upper surface of the conduit structure form a flow pathway.

4. The device of claim 3, wherein the flexible sealant structure further comprises a vacuum port in fluid communication with the flow pathway and configured to be coupled to a negative pressure source.

5. The device of claim 4, further comprising a one-way flow valve positioned between the negative pressure source and the flow pathway, the one-way flow valve configured to prevent backflow of fluid within the flow pathway.

6. The device of claim 4, wherein the flexible sealant structure further comprises a release liner adhered to the lower adhesive surface.

7. The device of claim 6, wherein the release liner further comprises a break line positioned near the vacuum port.

8. The device of claim 2, wherein the flexible sealant structure comprises a polyurethane sheet.

9. The device of claim 1, wherein at least a portion of the conduit structure is adapted to be aligned with a longitudinal axis of the incision.

10. The device of claim 1, wherein the conduit structure comprises a plurality of support structures on the upper surface.

11. The device of claim 10, wherein the plurality of support structures supports a sealant structure and prevents the sealant structure from blocking a flow pathway.

12. The device of claim 10, wherein the plurality of support structures comprises opposed side beams and a plurality of central posts.

13. The device of claim 12, wherein the plurality of central posts is interspersed with longitudinally arranged openings.

14. The device of claim 1, wherein the first mating end is configured to mate with a second mating end of another conduit structure, and wherein the second mating end is configured to mate with a first mating end of another conduit structure.

15. The device of claim 14, further comprising at least one of a first tension relief module configured to mate with the tension relief module at the first mating end or a second tension relief module configured to mate with the tension relief module at the second mating end.

16. The device of claim 1, wherein the conduit structure comprises a material that is highly elastic and highly recoverable.

17. The device of claim 16, wherein the material comprises at least one of a silicone elastomer, a polyurethane, a polyisoprene, or an elastomer.

18. The device of claim 1, wherein the opposing adhesive structures are configured to be manually stretched from a relaxed configuration to a first tensile configuration to adhere to tissue substantially perpendicular to a length of the incision.

19. The device of claim 18, wherein the opposing adhesive structures are adapted to return towards the relaxed configuration from the first tensile configuration into a second tensile configuration such that the opposing adhesive structures impart a contracting force towards a center of the incision.

20. The device of claim 19, further comprising an indicator reversibly coupled to an upper surface of the opposing adhesive structures, the indicator comprising opposing pull tabs each having an alignment marker.

21. The device of claim 20, wherein application of outward tension to the opposing pull tabs stretches the opposing adhesive structures towards the first tensile configuration.

22. The device of claim 21, wherein the alignment markers approach alignment with one another when the opposing adhesive structures are stretched towards the first tensile configuration.

23. The device of claim 21, wherein the indicator further comprises a mechanical interference feature that limits an outward tension that can be applied to the opposing adhesive structures.

24. The device of claim 1, wherein the opposing adhesive structures shield the incision from endogenous or exogenous stress by imposing a strain on a surface of healthy skin surrounding the incision.

25. The device of claim 1, wherein the opposing adhesive structures comprise at least one pair of wings extending outward from the conduit structure.

26. The device of claim 25, wherein the at least one pair of wings applies a force transverse to a longitudinal axis of the incision.

27. A system for treating an incision, the system comprising:
a device comprising:
a generally planar tension relief module, comprising:
a conduit structure comprising an upper surface, a lower surface, and at least one opening extending from the lower surface to the upper surface, wherein the at least one opening is configured to provide fluid communication between the upper surface of the conduit structure and an incision;
a first mating end positioned at a first end of the conduit structure;
a second mating end positioned at a second end of the conduit structure, wherein the second end of the conduit structure is opposite the first end of the conduit structure, and wherein each of the first mating end and the second mating end is configured to mate with another conduit structure; and
opposing adhesive structures coupled to the conduit structure; and
a negative pressure source configured to provide to negative pressure to the incision through upper surface, the at least one opening, and the lower surface.

28. The device of claim 27, further comprising a flexible sealant structure sized to cover the tension relief module, wherein the flexible sealant structure comprises a lower adhesive surface.

29. The device of claim 28, wherein the lower adhesive surface of the flexible sealant structure and the upper surface of the conduit structure form a flow pathway.

30. The device of claim 29, wherein the flexible sealant structure further comprises a vacuum port in fluid communication with the flow pathway and configured to be coupled to a negative pressure source.

31. The device of claim 30, further comprising a one-way flow valve positioned between the negative pressure source and the flow pathway, the one-way flow valve configured to prevent backflow of fluid within the flow pathway.

32. The device of claim 30, wherein the flexible sealant structure further comprises a release liner adhered to the lower adhesive surface.

33. The device of claim 32, wherein the release liner further comprises a break line positioned near the vacuum port.

34. The device of claim 28, wherein the first mating end is configured to mate with a second mating end of another conduit structure, and wherein the second mating end is configured to mate with a first mating end of another conduit structure.

35. The device of claim 34, further comprising at least one of a first tension relief module configured to mate with the tension relief module at the first mating end or a second tension relief module configured to mate with the tension relief module at the second mating end.

36. The device of claim 28, wherein the opposing adhesive structures are configured to be manually stretched from a relaxed configuration to a first tensile configuration to adhere to tissue substantially perpendicular to a length of the incision.

37. The device of claim 36, wherein the opposing adhesive structures are adapted to return towards the relaxed configuration from the first tensile configuration into a second tensile configuration such that the opposing adhesive structures impart a contracting force towards a center of the incision.

38. A device for treating an incision, the device comprising:
a tension relief module, comprising:
a conduit structure comprising an upper surface, a lower surface, and at least one opening extending from the lower surface to the upper surface, wherein the at least one opening is configured to provide fluid communication between the upper surface of the conduit structure and the incision, and
opposing adhesive structures coupled to the conduit structure, wherein the opposing adhesive structures are configured to be manually stretched from a relaxed configuration to a first tensile configuration to adhere to tissue substantially perpendicular to a length of the incision; and
a flexible sealant structure sized to cover the tension relief module, wherein the flexible sealant structure comprises a lower adhesive surface, and wherein the lower adhesive surface of the flexible sealant structure and the upper surface of the conduit structure form a flow pathway.

39. The device of claim 38, wherein the flexible sealant structure further comprises a vacuum port in fluid communication with the flow pathway and configured to be coupled to a negative pressure source.

40. The device of claim 39, further comprising a one-way flow valve positioned between the negative pressure source and the flow pathway, the one-way flow valve configured to prevent backflow of fluid within the flow pathway.

41. The device of claim 39, wherein the flexible sealant structure further comprises a release liner adhered to the lower adhesive surface.

42. The device of claim 41, wherein the release liner further comprises a break line positioned near the vacuum port.

43. The device of claim 38, further comprising a first mating end is configured to mate with a second mating end of another conduit structure, and wherein the second mating end is configured to mate with a first mating end of another conduit structure.

44. The device of claim 43, further comprising at least one of a first tension relief module configured to mate with the tension relief module at the first mating end or a second tension relief module configured to mate with the tension relief module at the second mating end.

45. The device of claim 38, wherein the opposing adhesive structures are configured to be manually stretched from a relaxed configuration to a first tensile configuration to adhere to tissue substantially perpendicular to a length of the incision.

46. The device of claim 45, wherein the opposing adhesive structures are adapted to return towards the relaxed configuration from the first tensile configuration into a second tensile configuration such that the opposing adhesive structures impart a contracting force towards a center of the incision.

* * * * *